(12) United States Patent
Herrera et al.

(10) Patent No.: US 8,828,390 B2
(45) Date of Patent: Sep. 9, 2014

(54) USES OF NOGO-A INHIBITORS AND RELATED METHODS

(75) Inventors: Pedro L. Herrera, Chene-Bourg (CH); Martin E. Schwab, Zurich (CH); Claire Bonal, Cambridge, MA (US); Patrice Lalive D'epinay, Chene-Bougeries (CH); Caroline Pot Kreis, Geneva (CH)

(73) Assignees: Universitat Zurich, Zurich (CH); Universite de Geneve, Geneva (CH)

( * ) Notice: Subject to any disclaimer, the term of this patent is extended or adjusted under 35 U.S.C. 154(b) by 0 days.

(21) Appl. No.: 13/809,224

(22) PCT Filed: Jul. 8, 2011

(86) PCT No.: PCT/IB2011/053056
§ 371 (c)(1),
(2), (4) Date: Feb. 8, 2013

(87) PCT Pub. No.: WO2012/004773
PCT Pub. Date: Jan. 12, 2012

(65) Prior Publication Data
US 2013/0136737 A1 May 30, 2013

Related U.S. Application Data

(60) Provisional application No. 61/362,876, filed on Jul. 9, 2010.

(51) Int. Cl.
- *A61K 39/395* (2006.01)
- *A61K 39/00* (2006.01)
- *C07K 16/00* (2006.01)
- *A61K 45/06* (2006.01)

(52) U.S. Cl.
CPC ......... *A61K 39/3955* (2013.01); *A61K 39/0005* (2013.01); *A61K 45/06* (2013.01)
USPC .................. 424/141.1; 424/142.1; 424/133.1; 424/145.1; 530/388.1; 530/388.15; 530/388.23

(58) Field of Classification Search
CPC ..................... A61K 2039/505; A61K 39/3955; A61K 38/17; A61K 39/39533; A61K 2039/6056; A61K 31/00; A61K 38/1709; C07K 16/18; C07K 14/4713; C07K 2317/76; C07K 2316/96
See application file for complete search history.

(56) References Cited

U.S. PATENT DOCUMENTS

| 2005/0260616 A1 | 11/2005 | Schwab et al. |
| 2011/0305751 A1* | 12/2011 | Gaillard ........................ 424/450 |

FOREIGN PATENT DOCUMENTS

| EP | 1711530 | 8/2009 |
| WO | WO 2004/052932 | 6/2004 |
| WO | WO 2005/028508 | 3/2005 |
| WO | WO 2005/061544 | 7/2005 |
| WO | WO 2007/057395 | 5/2007 |
| WO | WO 2007/068750 | 6/2007 |
| WO | WO 2009/056509 | 5/2009 |
| WO | WO 2010/004031 | 1/2010 |

OTHER PUBLICATIONS

Prinjha, et al. 2004, Drug Discovery Today. I:21-27.*
Cafferty, W. B. J. et al. "The Nogo-Nogo Receptor Pathway Limits a Spectrum of Adult CNS Axonal Growth" *The Journal of Neuroscience*, Nov. 22, 2006, pp. 12242-12250, vol. 26, No. 47.
Chen, M. S. et al. "Nogo-A is a myelin-associated neurite outgrowth inhibitor and an antigen for monoclonal antibody IN-1" *Nature*, Jan. 27, 2000, pp. 434-439, vol. 403.
De Fougerolles, A. R. "Delivery Vehicles for Small Interfering RNA in Vivo" *Human Gene Therapy*, Feb. 2008, pp. 125-132, vol. 19.
Fenske, D. B. et al. "Liposomal nanomedicines" *Expert Opin. Drug Deliv.*, 2008, pp. 25-44, vol. 5, No. 1.
Jokic, N. et al. "Nogo Expression in Muscle Correlates with Amyotrophic Lateral Sclerosis Severity" *Ann Neurol*, 2005, pp. 553-556, vol. 57.
Knudsen, L. B. et al. "Small-molecule agonists for the glucagon-like peptide 1 receptor" *PNAS*, Jan. 16, 2007, pp. 937-942, vol. 104, No. 3.
Koyama, H. et al. "5-Aryl Thiazolidine-2,4-diones as Selective PPARγ Agonists" *Bioorganic & Medicinal Chemistry Letters*, 2003, pp. 1801-1804, vol. 13.
Montani, L. et al. "Neuronal Nogo-A Modulates Growth Cone Motility via Rho-GTP/LIMK1/Cofilin in the Unlesioned Adult Nervous System" *The Journal of Biological Chemistry*, Apr. 17, 2009, pp. 10793-10807, vol. 284, No. 16.
Oertle, T. et al. "Nogo-A Inhibits Neurite Outgrowth and Cell Spreading with Three Discrete Regions" *The Journal of Neuroscience*, Jul. 2, 2003, pp. 5393-5406, vol. 23, No. 13.
Rossi, J. et al. "Parasympathetic Innervation and Function of Endocrine Pancreas Requires the Glial Cell Line-Derived Factor Family Receptor α2 (GFRα2)" *Diabetes*, May 2005, pp. 1324-1330, vol. 54.
Schwab, M. E. "Nogo and axon regeneration" *Current Opinion in Neurobiology*, 2004, pp. 118-124, vol. 14.
Simonen, M. et al. "Systemic Deletion of the Myelin-Associated Outgrowth Inhibitor Nogo-A Improves Regenerative and Plastic Responses after Spinal Cord Injury" *Neuron*, Apr. 24, 2003, pp. 201-211, vol. 38.
Walmsley, A. R. "Targeting the Nogo-A Signalling Pathway to Promote Recovery Following Acute CNS Injury" *Current Pharmaceutical Design*, 2007, pp. 2470-2484, vol. 13.
Yang, Y. et al. "Silencing Nogo-A Promotes Functional Recovery in Demyelinating Disease" *Ann Neurol*, 2010, pp. 498-507, vol. 67.

(Continued)

*Primary Examiner* — Shulamith H Shafer
(74) *Attorney, Agent, or Firm* — Saliwanchik, Lloyd & Eisenschenk

(57) ABSTRACT

The present invention is directed to Nogo-A antagonists useful for the control of blood glucose or blood insulin levels in a subject and related use and formulation thereof. In particular, the invention is directed to Nogo-A antagonists useful for the prevention, repression or treatment insulin secretion deficiency and related methods and pharmaceutical formulations. In particular, the invention relates to Nogo-A antagonists useful in the treatment of diabetes mellitus.

12 Claims, 14 Drawing Sheets

(56) References Cited

OTHER PUBLICATIONS

Written Opinion in International Application No. PCT/US2004/10832, Mar. 3, 2005, pp. 1-3.
Aloy, E. M. et al. "Synaptic destabilization by neuronal Nogo-A" *Brain Cell Biology*, 2006, pp. 137-157, vol. 35.
Campbell, I. W. et al. "Sulfonylureas and hypoglycemia" *Diabetic Hypoglycemia*, May 2009, pp. 3-10, vol. 2, Issue 1.
Bonal, C. B. et al. "Nogo-A Downregulation Improves Insulin Secretion in Mice" *Diabetes*, 2013, pp. 1-11, vol. 62.
Davidson, M. et al. "Metabolic and Clinical Effects of Glibenclamide" *The Lancet*, Jan. 10, 1970, pp. 57-61, vol. 1, No. 7637.
Dimou, L. et al. "Nogo-A-Deficient Mice Reveal Strain-Dependent Differences in Axonal Regeneration" *The Journal of Neurobiology*, May 24, 2006, pp. 5591-5603, vol. 26, No. 21.

\* cited by examiner

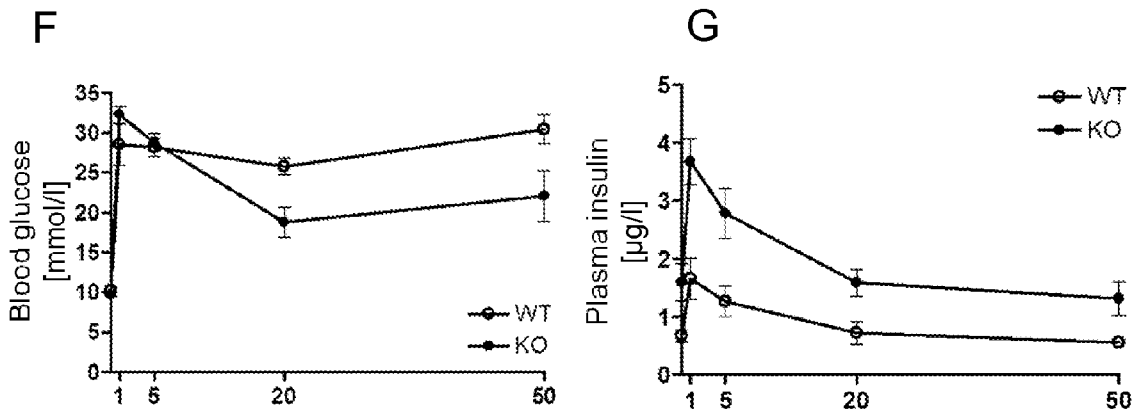
Figure 3 (continued)
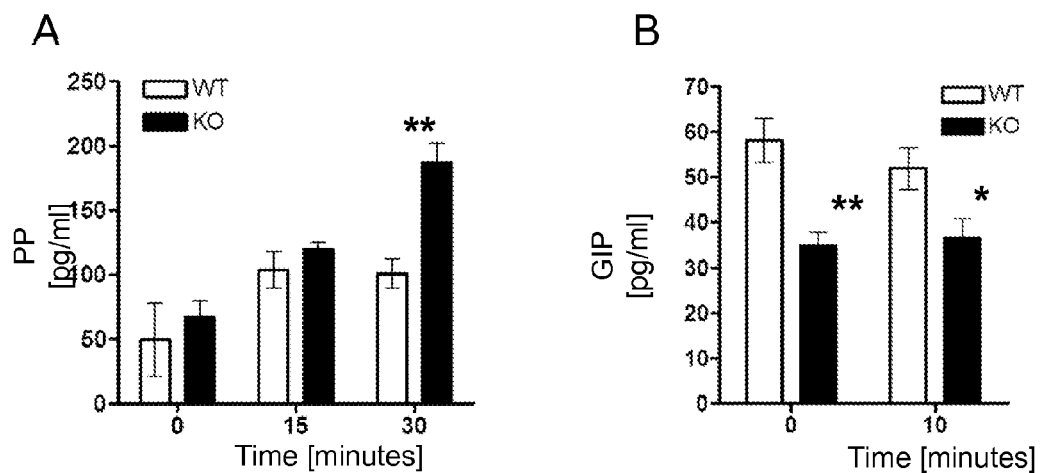
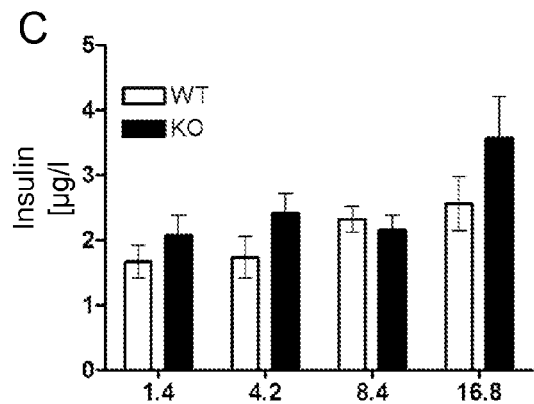
Figure 4

SEQ ID NO: 1
Human Nogo-A amino acid sequence

Accession: UNIPROT:Q9NQC3

>Q9NQC3 Reticulon-4 (Neurite outgrowth inhibitor) (Nogo protein)

MEDLDQSPLVSSSDSPPRPQPAFKYQFVREPEDEEEEEEEEEDEDEDLE
ELEVLERKPAAGLSAAPVPTAPAAGAPLMDFGNDFVPPAPRGPLPAAPPV
APERQPSWDPSPVSSTVPAPSPLSAAAVSPSKLPEDDEPPARPPPPPPAS
VSPQAEPVWTPPAPAPAAPPSTPAAPKRRGSSGSVDETLFALPAASEPVI
RSSAENMDLKEQPGNTISAGQEDFPSVLLETAASLPSLSPLSAASFKEHE
YLGNLSTVLPTEGTLQENVSEASKEVSEKAKTLLIDRDLTEFSELEYSEM
GSSFSVSPKAESAVIVANPREEIIVKNKDEEEKLVSNNILHNQQELPTAL
TKLVKEDEVVSSEKAKDSFNEKRVAVEAPMREEYADFKPFERVWEVKDSK
EDSDMLAAGGKIESNLESKVDKKCFADSLEQTNHEKDSESSNDDTSFPST
PEGIKDRSGAYITCAPFNPAATESIATNIFPLLGDPTSENKTDEKKIEEK
KAQIVTEKNTSTKTSNPFLVAAQDSETDYVTTDNLTKVTEEVVANMPEGL
TPDLVQEACESELNEVTGTKIAYETKMDLVQTSEVMQESLYPAAQLCPSF
EESEATPSPVLPDIVMEAPLNSAVPSAGASVIQPSSSPLEASSVNYESIK
HEPENPPPYEEAMSVSLKKVSGIKEEIKEPENINAALQETEAPYISIACD
LIKETKLSAEPAPDFSDYSEMAKVEQPVPDHSELVEDSSPDSEPVDLFSD
DSIPDVPQKQDETVMLVKESLTETSFESMIEYENKEKLSALPPEGGKPYL
ESFKLSLDNTKDTLLPDEVSTLSKKEKIPLQMEELSTAVYSNDDLFISKE
AQIRETETFSDSSPIEIIDEFPTLISSKTDSFSKLAREYTDLEVSHKSEI
ANAPDGAGSLPCTELPHDLSLKNIQPKVEEKISFSDDFSKNGSATSKVLL
LPPDVSALATQAEIESIVKPKVLVKEAEKKLPSDTEKEDRSPSAIFSAEL
SKTSVVDLLYWRDIKKTGVVFGASLFLLLSLTVFSIVSVTAYIALALLSV
TISFRIYKGVIQAIQKSDEGHPFRAYLESEVAISEELVQKYSNSALGHVN
CTIKELRRLFLVDDLVDSLKFAVLMWVFTYVGALFNGLTLLILALISLFS
VPVIYERHQAQIDHYLGLANKNVKDAMAKIQAKIPGLKRKAE

Figure 6A

SEQ ID NO: 2
Human Nogo-A nucleic acid coding sequence

Accession:GENBANK:AJ251383

>AJ251383 Homo sapiens mRNA for Nogo-A protein (Nogo gene)

atggaagacctggaccagtctcctctggtctcgtcctcggacagcccaccccggccgcagcccgcgttcaagtaccagttcgtgagggagcc
cgaggacgaggaggaagaagaggaggaggaagaggaggacgaggacgaagacctggaggagctggaggtgctggagaggaagcc
cgccgccgggctgtccgcggcccccagtgcccaccgcccctgccgccggcgcgcccctgatggacttcggaaatgacttcgtgccgccggcg
ccccggggaccccctgccggccgctcccccgtcgccccggagcggcagccgtcttgggacccgagcccggtgtcgtcgaccgtgcccgcg
ccatccccgctgtctgctgccgcagtctcgccctccaagctccctgaggacgacgagcctccggcccggcctcccccctcctccccggccagc
gtgagcccccaggcagagcccgtgtggaccccgccagcccggctcccgccgcgccccctccaccccggccgcgcccaagcgcaggg
gctcctcgggctcagtggatgagaccttttgctcttcctgctgcatctgagcctgtgatacgctcctctgcagaaaatatggacttgaaggagca
gccaggtaacactatttcggctggtcaagaggatttcccatctgtcctgcttgaaactgctgcttctcttccttctctgtctcctctctcagccgcttcttc
aaagaacatgaataccttggtaatttgtcaacagtattacccactgaaggaacacttcaagaaaatgtcagtgaagcttctaaagaggtctcag
agaaggcaaaaactctactcatagatagagatttaacagagttttcagaattagaatactcagaaatggatcatcgttcagtgtctctccaaaa
gcagaatctgccgtaatagtagcaaatcctaggggaagaaataatcgtgaaaaataaagatgaagaagagaagttagttagtaataacatcctt
cataatcaacaagagttacctacagctcttactaaattggtaaagaggatgaagttgtgtcttcagaaaaagcaaaagacagttttaatgaaaa
gagagttgcagtggaagctccatgagggaggaatatgcagacttcaaaccatttgagcgagtatgggaagtgaaagatagtaaggaagata
gtgatatgttggctgctggaggtaaaatcgagagcaacttggaaagtaaagtggataaaaaatgttttgcagatagccttgagcaaactaatca
cgaaaaagatagtgagagtagtaatgatgacttcttccccagtacgccagaaggtataaaggatcgtccaggagcatatatcacatgtgct
cccttaacccagcagcaactgagagcattgcaacaaacattttccttgttaggagatcctacttcagaaaataagaccgatgaaaaaaaat
agaagaaaagaaggcccaaatagtaacagagaagaatactagcaccaaaacatcaaaccctttcttgtagcagcacaggattctgagac
agattatgtcacaacagataatttaacaaaggtgactgaggaagtcgtggcaaacatgcctgaaggcctgactccagatttagtacaggaagc
atgtgaaagtgaattgaatgaagttactggtacaaagattgcttatgaaacaaaaatggacttggttcaaacatcagaagttatgcaagagtcac
tctatcctgcagcacagctttgcccatcatttgaagagtcagaagctactccttcaccagttttgcctgacattgttatggaagcaccattgaattctg
cagttcctagtgctggtgcttccgtgatacagcccagctcatcaccattagaagcttcttcagttaattatgaaagcataaaacatgagcctgaaa
accccccaccatatgaagaggccatgagtgtatcactaaaaaagtatcaggaataaaggaagaaattaaagagcctgaaaatattaatgc
agctcttcaagaaacagaagctccttatatatctattgcatgtgatttaattaaagaaacaaagctttctgctgaaccagctccggatttctctgattat
tcagaaatggcaaaagttgaacagccagtgcctgatcattctgagctagttgaagattcctcacctgattctgaaccagttgacttatttagtgatg
attcaatacctgacgttccacaaaaacaagatgaaactgtgatgcttgtgaaagaaagtctcactgagacttcatttgagtcaatgatagaatatg
aaaaataaggaaaaactcagtgctttgccacctgagggaggaaagccatatttggaatcttttaagctcagtttagataacacaaaagatcccct
gttacctgatgaagtttcaacattgagcaaaaggagaaaattcctttgcagatggaggagctcagtactgcagtttattcaaatgatgacttattt
atttctaaggaagcacagataagagaaactgaaacgttttcagattcatctccaattgaaattatagatgagttccctacattgatcagttctaaaa
ctgattcattttctaaattagccagggaatatactgacctagaagtatcccacaaaagtgaaattgctaatgccccggatggagctgggtcattgc
cttgcacagaattgcccccatgacctttctttgaagaacatacaacccaaagttgaagagaaaatcagtttctcagatgacttttctaaaaatgggtc
tgctacatcaaaggtgctcttattgcctccagatgtttctgtttggccactcaagcagagatagagagcatagttaaacccaaagttcttgtgaaa
gaagctgagaaaaaacttccttccgatacagaaaaagaggacagatcaccatctgctatattttcagcagagctgagtaaaacttcagttgttg
acctcctgtactggagagacattaagaagactggagtggtgtttggtgccagcctattcctgctgctttcattgacagtattcagcattgtgagcgta
acagcctacattgccttggccctgctctctgtgaccatcagctttaggatatacaagggtgtgatccaagctatccagaaatcagatgaaggcca
cccattcagggcatatctggaatctgaagttgctatatctgaggagttggttcagaagtacagtaattctgctcttggtcatgtgaactgcacgataa
aggaactcaggcgcctcttcttagttgatgatttagttgattctctgaagtttgcagtgttgatgtgggtatttacctatgttggtccttgtttaatggtctg
acactactgatttggctctcatttcactcttcagtgttcctgttatttatgaacggcatcaggcgcagatagatcattatctaggacttgcaaataaga
atgttaaagatgctatggctaaaatccaagcaaaaatccctggattgaagcgcaaagctgaatga

Figure 6B

SEQ ID NO: 8
rat Nogo-A amino acid sequence

Accession:UNIPROT:Q9JK11
>Q9JK11 Reticulon-4 (Neurite outgrowth inhibitor) (Nogo protein)

MEDIDQSSLVSSSTDSPPRPPPAFKYQFVTEPEDEEDEEEEEDEEEDDEDLEELEVLERKPA
AGLSAAAVPPAAAAPLLDFSSDSVPPAPRGPLPAAPPAAPERQPSWERSPAAPAPSLPPAAA
VLPSKLPEDDEPPARPPPPPPAGASPLAEPAAPPSTPAAPKRRGSGSVDETLFALPAASEPVI
PSSAEKIMDLMEQPGNTVSSGQEDFPSVLLETAASLPSLSPLSTVSFKEHGYLGNLSAVSSSE
GTIEETLNEASKELPERATNPFVNRDLAEFSELEYSEMGSSFKGSPKGESAILVENTKEEVIVR
SKDKEDLVCSAALHSPQESPVGKEDRVVSPEKTMDIFNEMQMSVVAPVREEYADFKPFEQA
WEVKDTYEGSRDVLAARANVESKVDRKCLEDSLEQKSLGKDSEGRNEDASFPSTPEPVKDS
SRAYITCASFTSATESTTANTFPLLEDHTSENKTDEKKIEERKAQIITEKTSPKTSNPFLVAVQD
SEADYVTTDTLSKVTEAAVSNMPEGLTPDLVQEACESELNEATGTKIAYETKVDLVQTSEAIQ
ESLYPTAQLCPSFEEAEATPSPVLPDIVMEAPLNSLLPSAGASVVQPSVSPLEAPPPVSYDSIK
LEPENPPPYEEAMNVALKALGTKEGIKEPESFNAAVQETEAPYISIACDLIKETKLSTEPSPDFS
NYSEIAKFEKSVPEHAELVEDSSPESEPVDLFSDDSIPEVPQTQEEAVMLMKESLTEVSETVA
QHKEERLSASPQELGKPYLESFQPNLHSTKDAASNDIPTLTKKEKISLQMEEFNTAIYSNDDLL
SSKEDKIKESETFSDSSPIEIIDEFPTFVSAKDDSPKLAKEYTDLEVSDKSEIANIQSGADSLPCL
ELPCDLSFKNIYPKDEVHVSDEFSENRSSVSKASISPSNVSALEPQTEMGSIVKSKSLTKEAEK
KLPSDTEKEDRSLSAVLSAELSKTSVVDLLYWRDIKKTGVVFGASLFLLLSLTVFSIVSVTAYIAL
ALLSVTISFRIYKGVIQAIQKSDEGHPFRAYLESEVAISEELVQKYSNSALGHVNSTIKELRRLFL
VDDLVDSLKFAVLMWVFTYVGALFNGLTLLILALISLFSIPVIYERHQVQIDHYLGLANKSVKDA
MAKIQAKIPGLKRKAD

Figure 6C

SEQ ID NO: 9
Bovine Nogo-A amino acid sequence

Accession: UNIPROT:A7YVI6
>A7YVI6 RTN4 protein

MPEGLTPDLVQEACESELNEATGTKIAFETKMDLVQTSEAVQESLYPVTQLCPSFEESEA
TPSPVLPDIVMEAPLNSVVPSAGASAVQLSSSPLETPPSVNYESIKFEPENPPPYEEAMNV
SLKKESGMNEEITEPEGISVAVQETEAPYISIACDLIKETKISTEPTPDFSSYSEIAEVAQPVP
EHSELVEDSSPDSEPVDLFSDDSIPEVPQKQDEAVILVKENLTEISSESMTGHDNKGKLSA
SPSPEGGKPYLESFQPSLGITKDTLAPDEVSALTQKEKIPLQMEELNTAVYSSDGLFIAQEA
NLRESETFSDSSPIEIIDEFPTFVSSKADSSPTLAREYTDLEVAHKSEIADIQDGAGSLACAG
LPHDLSFKSIQPKEEVHVPDEFSKDRGDVSKVPILPPDVSALDAQAEIGSIEKPKVLVKEAE
RKLPSDTEKERRSPSAIFSAELSKTSVVDLLYWRDIKKTGVVFGASLFLLLSLTVFSIVSVTA
YIALALLSVTISFRIYKGVIQAIQKSDEGHPFRAYLESEVAISEELVQKYSNSALGHVNCTIKE
LRRLFLVDDLVDSLKFAVLMWVFTYVGALFNGLTLLILALISLFSVPVIYERHQAQIDHYLGL
ANKNVKDAMAKIQAKIPGLKRKAE

Figure 6D

SEQ ID No: 10
Mouse Nogo-A amino acid sequence

Accession: UNIPROT:Q99P72
>Q99P72 Reticulon-4 (Neurite outgrowth inhibitor) (Nogo protein)

MEDIDQSSLVSSSADSPPRPPPAFKYQFVTEPEDEEDEEDEEEEDDEDLEELEVLERKP
AAGLSAAPVPPAAAPLLDFSSDSVPPAPRGPLPAAPPTAPERQPSWERSPAASAPSLPPA
AAVLPSKLPEDDEPPARPPAPAGASPLAEPAAPPSTPAAPKRRGSGSVDETLFALPAASE
PVIPSSAEKIMDLKEQPGNTVSSGQEDFPSVLFETAASLPSLSPLSTVSFKEHGYLGNLS
AVASTEGTIEETLNEASRELPERATNPFVNRESAEFSVLEYSEMGSSFNGSPKGESAMLV
ENTKEEVIVRSKDKEDLVCSAALHNPQESPATLTKVVKEDGVMSPEKTMDIFNEMKMSVV
APVREEYADFKPFEQAWEVKDTYEGSRDVLAARANMESKVDKKCFEDSLEQKGHGKDSES
RNENASFPRTPELVKDGSRAYITCDSFSSATESTAANIFPVLEDHTSENKTDEKKIEERK
AQIITEKTSPKTSNPFLVAIHDSEADYVTTDNLSKVTEAVVATMPEGLTPDLVQEACESE
LNEATGTKIAYETKVDLVQTSEAIQESIYPTAQLCPSFEEAEATPSPVLPDIVMEAPLNS
LLPSTGASVAQPSASPLEVPSPVSYDGIKLEPENPPPYEEAMSVALKTSDSKEEIKEPES
FNAAAQEAEAPYISIACDLIKETKLSTEPSPEFSNYSEIAKFEKSVPDHCELVDDSSPES
EPVDLFSDDSIPEVPQTQEEAVMLMKESLTEVSETVTQHKHKERLSASPQEVGKPYLESF
QPNLHITKDAASNEIPTLTKKETISLQMEEFNTAIYSNDDLLSSKEDKMKESETFSDSSP
IEIIDEFPTFVSAKDDSPKEYTDLEVSNKSEIANVQSGANSLPCSELPCDLSFKNTYPKD
EAHVSDEFSKSRSSVSKVPLLLPNVSALESQIEMGNIVKPKVLTKEAEEKLPSDTEKEDR
SLTAVLSAELNKTSVVDLLYWRDIKKTGVVFGASLFLLLSLTVFSIVSVTAYIALALLSV
TISFRIYKGVIQAIQKSDEGHPFRAYLESEVAISEELVQKYSNSALGHVNSTIKELRRLF
LVDDLVDSLKFAVLMWVFTYVGALFNGLTLLILALISLFSIPVIYERHQAQIDHYLGLAN
KSVKDAMAKIQAKIPGLKRKAE

Figure 6E

SEQ ID NO 20 : 2A10 Heavy chain humanised construct H20
MGWSCIILFLVATATGVHSQVQLVQSGAEVKKPGASVKVSCKASGYTFTSYWMHWVRQAPGQGL
EWIGNINPSNGGTNYNEKFKSKATMTRDTSTSTAYMELSSLRSEDTAVYYCELGQGYWGQGTLVT
VSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELAGAPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHYTQKSLSL
SPGK SEQ ID No 21: 2A10 Heavy chain humanised construct H26
MGWSCIILFLVATATGVHSQVQLVQSGAEVKKPGASVKVSCKASGYTFTSYWMHWVRQAPGQGL
EWIGNINPSNGGTNYNEKFKSRATMTRDTSTSTAYMELSSLRSEDTAVYYCELMQGYWGQGTLVT
VSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELAGAPSVFLFPPK
PKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLS
LSPGK SEQ ID No 22: 2A10 Heavy chain humanised construct H27
MGWSCIILFLVATATGVHSQVQLVQSGAEVKKPGASVKVSCKASGYTFTSYWMHWVKQRPGQGL
EWIGNINPSNGGTNYNEKFKSKATLTVDKSTSTAYMELSSLRSEDTAVYYCELMQGYWGQGTLVT
VSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELAGAPSVFLFPPK
PKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLS
LSPGK SEQ ID No 23: 2A10 Heavy chain humanised construct H28
MGWSCIILFLVATATGVHSQVQLVQSGAEVKKPGASVKVSCKASGYTFTSYWMHWVRQAPGQGL
EWIGNINPSNGGTNYNEKFKSKATMTRDTSTSTAYMELSSLRSEDTAVYYCELMQGYWGQGTLVT
VSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELAGAPSVFLFPPK
PKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLS
LSPGK SEQ ID NO. 24: 2A10 Light chain humanised construct L16
MGWSCIILFLVATATGVHSDIVMTQSPLSNPVTLGQPVSISCRSSKSLLYKDGKTYLNWFLQRPGQS
PQLLIYLMSTRASGVPDRFSGGGSGTDFTLKISRVEAEDVGVYYCQQLVEYPLTFGQGTKLEIKRTV
AAPSVFIFPPSDEQLKSGTASWCLLNNFYPREAKVQWKVDNALQSGNSQESVTEQDSKDSTYSLS
STLTLSKADYEKHKVY ACEVTHQGLSSPVTKSFNRGEC SEQ ID NO. 25: 2A10 Light chain humanised construct L13
MGWSCIILFLVATATGVHSDIVMTQSPLSLPVTLGQPASISCRSSKSLLYKDGKTYLNWFQQRPGQS
PQLLIYLMSTRASGVPDRFSGGGSGTDFTLKISRVEAEDVGVYYCQQLVEYPLTFGQGTKLEIKRTV
AAPSVFIFPPSDEQLKSGTASWCLLNNFYPREAKVQWKVDNALQSGNSQESVTEQDSKDSTYSLS
STLTLSKADYEKHKVY ACEVTHQGLSSPVTKSFNRGEC

Figure 6F

SEQ ID 26: 2A10 VH humanised construct H20
QVQLVQSGAEVKKPGASVKVSCKASGYTFTSYWMHWVRQAPGQGLEWIGNINPSNGGTN
YNEKFKSKATMTRDTSTSTAYMELSSLRSEDTAVYYCELGQGYWGQGTLVTVSS SEQ ID 27: 2A10 VH humanised construct H27
QVQLVQSGAEVKKPGASVKVSCKASGYTFTSYWMHWVKQRPGQGLEWIGNINPSNGGTN
YNEKFKSKATLTVDKSTSTAYMELSSLRSEDTAVYYCELMQGYWGQGTLVTVSS SEQ ID 28: 2A10 VH humanised construct H28
QVQLVQSGAEVKKPGASVKVSCKASGYTFTSYWMHWVRQAPGQGLEWIGNINPSNGGTN
YNEKFKSKATMTRDTSTSTAYMELSSLRSEDTAVYYCELMQGYWGQGTLVTVSS SEQ ID 29: 2A10 VL humanised construct L13
DIVMTQSPLSLPVTLGQPASISCRSSKSLLYKDGKTYLNWFQQRPGQSPQLLIYLMSTRASG
VPDRFSGGGSGTDFTLKISRVEAEDVGVYYCQQLVEYPLTFGQGTKLEIK SEQ ID 30: 2A10 VL humanised construct L16
DIVMTQSPLSNPVTLGQPVSISCRSSKSLLYKDGKTYLNWFLQRPGQSPQLLIYLMSTRASG
VPDRFSGGGSGTDFTLKISRVEAEDVGVYYCQQLVEYPLTFGQGTKLEIK

Figure 6G

SEQ ID NO:31: Variable part of heavy chain of 11C7 with leader sequence
MDFGLIFFIVGLLKGVQCEVKLLESGGLVQPGGSLKLSCVVSGFDFRRNWMSWVRQAPGKG
LEWIGEINPDSSKINYTPSLKDKFIISRDNAKNTLYLQVSTVRSEDTALYTCVRPVWMYAMDY
WGQGTSVTVSSAKTTPPSVYPLAPGSAAQTNSMVTLGCLVKGYFPEPVTVTWNSGSLSSG
VHTFPAVLQSDLYTLSSSVTVPS STWPSETVTCNVA SEQ ID NO:32: Light chain of 11C7 with leader sequence
MSPAQFLFLLVLWIRETSGDVLLTQTPLTLSITIGQPASISCKSSQSLLHSDGKTYLNWLLQRP
GQSPKRLIYLVSKLDSGVPDEFTGSGSGTDFTLKISRVEAGDLGLYYCWQGTHFPQTFGGG
TKLEIKRADAAPTVSIFPPSSGQLTSGGASVVCFLNNFYPKDINVKWKIDGSERQNGVLNSW
DQDSKDSTYSMSSTLTLTKD EYERHNSYTCEATHKTSTSPIVKSFNRGEC SEQ ID NO:33: Variable part of heavy chain of 6A3 with leader sequence
MEFGLSWVFLVAILEGVQCEVQLVESGGGLVQPGGSLRLSCAASGFTFSNYWMSWVRQAP
GKGLEWVATIKQDGSQKNYVDSVKGRFTISRDNAKNSLYLRLNSLRAEDTAVYYCATELFDL
WGRGSLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCP SEQ ID NO:34: Variable part of light chain of 6A3 with leader sequence
MEAPAQLLFLLLLWLPDTTGEIVLTQSPATLSLSPGERATLSCRASQSVSSYLAWYQQKPGQ
APRLLIYDASNRATGIPARFSGSGSGTDFTLTISSLEPEDFAVYYCQQRSNWPITFGQGTRLEI
KRTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

Figure 6H

SEQ ID NO: 4 HUMAN NOGO-A FRAGMENT 132-939
KLPEDDEPPARPPPPPPASVSPQAEPVVWTPPAPAPAAPPSTPAAPKRRGSSGSVDETLFALPAASEP
VIRSSAENMDLKEQPGNTISAGQEDFPSVLLETAASLPSLSPLSAASFKEHEYLGNLSTVLPTEGTLQE
NVSEASKEVSEKAKTLLIDRDLTEFSELEYSEMGSSFSVSPKAESAVIVANPREEIIVKNKDEEEKLVSN
NILHNQQELPTALTKLVKEDEVVSSEKAKDSFNEKRVAVEAPMREEYADFKPFERVWEVKDSKEDSD
MLAAGGKIESNLESKVDKKCFADSLEQTNHEKDSESSNDDTSFPSTPEGIKDRSGAYITCAPFNPAAT
ESIATNIFPLLGDPTSENKTDEKKIEEKKAQIVTEKNTSTKTSNPFLVAAQDSETDYVTTDNLTKVTEEV
VANMPEGLTPDLVQEACESELNEVTGTKIAYETKMDLVQTSEVMQESLYPAAQLCPSFEESEATPSP
VLPDIVMEAPLNSAVPSAGASVIQPSSSPLEASSVNYESIKHEPENPPPYEEAMSVSLKKVSGIKEEIKE
PENINAALQETEAPYISIACDLIKETKLSAEPAPDFSDYSEMAKVEQPVPDHSELVEDSSPDSEPVDLF
SDDSIPDVPQKQDETVMLVKESLTETSFESMIEYENKEKLSALPPEGGKPYLESFKLSLDNTKDTLLPD
EVSTLSKKEKIPLQMEELSTAVYSNDDLFISKEAQIRETETFSDSSPIEIIDEFPTLISSKTDSFSKLAREY
TDLEVSHKSEIANAPDGAGSLPCTELPHDLSLKNIQPKVEEKISFSDDFS

SEQ ID NO: 5 HUMAN NOGO-A FRAGMENT 205-501
NMDLKEQPGNTISAGQEDFPSVLLETAASLPSLSPLSAASFKEHEYLGNLSTVLPTEGTLQENVSEAS
KEVSEKAKTLLIDRDLTEFSELEYSEMGSSFSVSPKAESAVIVANPREEIIVKNKDEEEKLVSNNILHNQ
QELPTALTKLVKEDEVVSSEKAKDSFNEKRVAVEAPMREEYADFKPFERVWEVKDSKEDSDMLAAG
GKIESNLESKVDKKCFADSLEQTNHEKDSESSNDDTSFPSTPEGIKDRSGAYITCAPFNPAATESIATN
IFPLLGDPTSENKTDEKKIEEKK

SEQ ID NO: 6 HUMAN NOGO-A FRAGMENT 501-680
KAQIVTEKNTSTKTSNPFLVAAQDSETDYVTTDNLTKVTEEVVANMPEGLTPDLVQEACESELNEVTG
TKIAYETKMDLVQTSEVMQESLYPAAQLCPSFEESEATPSPVLPDIVMEAPLNSAVPSAGASVIQPSSS
PLEASSVNYESIKHEPENPPPYEEAMSVSLKKVSGIKEEIKEP

SEQ ID NO: 7 HUMAN NOGO-A FRAGMENT 132-206
KLPEDDEPPARPPPPPPASVSPQAEPVVWTPPAPAPAAPPSTPAAPKRRGSSGSVDETLFALPAASEP
VIRSSAEN

SEQ ID NO: 34 HUMAN NOGO-A FRAGMENT 680-939
PENINAALQETEAPYISIACDLIKETKLSAEPAPDFSDYSEMAKVEQPVPDHSELVEDSSPDSEPVDLF
SDDSIPDVPQKQDETVMLVKESLTETSFESMIEYENKEKLSALPPEGGKPYLESFKLSLDNTKDTLLPD
EVSTLSKKEKIPLQMEELSTAVYSNDDLFISKEAQIRETETFSDSSPIEIIDEFPTLISSKTDSFSKLAREY
TDLEVSHKSEIANAPDGAGSLPCTELPHDLSLKNIQPKVEEKISFSDDFS

SEQ ID NO: 35 HUMAN NOGO-A FRAGMENT 940-1127
KNGSATSKVLLLPPDVSALATQAEIESIVKPKVLVKEAEKKLPSDTEKEDRSPSAIFSAELSKTSVVDLL
YWRDIKKTGVVFGASLFLLLSLTVFSIVSVTAYIALALLSVTISFRIYKGVIQAIQKSDEGHPFRAYLESEV
AISEELVQKYSNSALGHVNCTIKELRRLFLVDDLVDSLKFAVLMWV

SEQ ID NO: 37 HUMAN NOGO-A FRAGMENT 342-357
NQQELPTALTKLVKED

SEQ ID NO: 38 HUMAN NOGO-A FRAGMENT 544-725
ANMPEGLTPDLVQEACESELNEVTGTKIAYETKMDLVQTSEVMQESLYPAAQLCPSFEESEATPSPV
LPDIVMEAPLNSAVPSAGASVIQPSSSPLEASSVNYESIKHEPENPPPYEEAMSVSLKKVSGIKEEIKEP
ENINAALQETEAPYISIACDLIKETKLSAEPAPDFSDYSEMAKVE

Figure 6I

SEQ ID NO: 36 HUMAN NOGO-A FRAGMENT 1-979
MEDLDQSPLVSSSDSPPRPQPAFKYQFVREPEDEEEEEEEEEEDEDEDLEELEVLERKPAAGLSAAP
VPTAPAAGAPLMDFGNDFVPPAPRGPLPAAPPVAPERQPSWDPSPVSSTVPAPSPLSAAAVSPSKLP
EDDEPPARPPPPPPASVSPQAEPVWTPPAPAPAAPPSTPAAPKRRGSSGSVDETLFALPAASEPVIR
SSAENMDLKEQPGNTISAGQEDFPSVLLETAASLPSLSPLSAASFKEHEYLGNLSTVLPTEGTLQENV
SEASKEVSEKAKTLLIDRDLTEFSELEYSEMGSSFSVSPKAESAVIVANPREEIIVKNKDEEEKLVSNNIL
HNQQELPTALTKLVKEDEVVSSEKAKDSFNEKRVAVEAPMREEYADFKPFERVWEVKDSKEDSDML
AAGGKIESNLESKVDKKCFADSLEQTNHEKDSESSNDDTSFPSTPEGIKDRSGAYITCAPFNPAATESI
ATNIFPLLGDPTSENKTDEKKIEEKKAQIVTEKNTSTKTSNPFLVAAQDSETDYVTTDNLTKVTEEVVA
NMPEGLTPDLVQEACESELNEVTGTKIAYETKMDLVQTSEVMQESLYPAAQLCPSFEESEATPSPVL
PDIVMEAPLNSAVPSAGASVIQPSSSPLEASSVNYESIKHEPENPPPYEEAMSVSLKKVSGIKEEIKEP
ENINAALQETEAPYISIACDLIKETKLSAEPAPDFSDYSEMAKVEQPVPDHSELVEDSSPDSEPVDLFS
DDSIPDVPQKQDETVMLVKESLTETSFESMIEYENKEKLSALPPEGGKPYLESFKLSLDNTKDTLLPDE
VSTLSKKEKIPLQMEELSTAVYSNDDLFISKEAQIRETETFSDSSPIEIIDEFPTLISSKTDSFSKLAREYT
DLEVSHKSEIANAPDGAGSLPCTELPHDLSLKNIQPKVEEKISFSDDFSKNGSATSKVLLLPPDVSALA
TQAEIESIVKPKVLVKEAEK

SEQ ID NO: 39 HUMAN NOGO-A FRAGMENT 567-748
TGTKIAYETKMDLVQTSEVMQESLYPAAQLCPSFEESEATPSPVLPDIVMEAPLNSAVPSAGASVIQP
SSSPLEASSVNYESIKHEPENPPPYEEAMSVSLKKVSGIKEEIKEPENINAALQETEAPYISIACDLIKET
KLSAEPAPDFSDYSEMAKVEQPVPDHSELVEDSSPDSEPVDLF

SEQ ID NO: 40 HUMAN NOGO-A FRAGMENT 610-621
VLPDIVMEAPLN

SEQ ID NO: 41 BOVINE NOGO-A FRAGMENT 101-118
NYESIKFEPENPPPYEEA

SEQ ID NO: 42 RAT NOGO-A FRAGMENT 623-640
SYDSIKLEPENPPPYEEA

Figure 6I (continued)

A
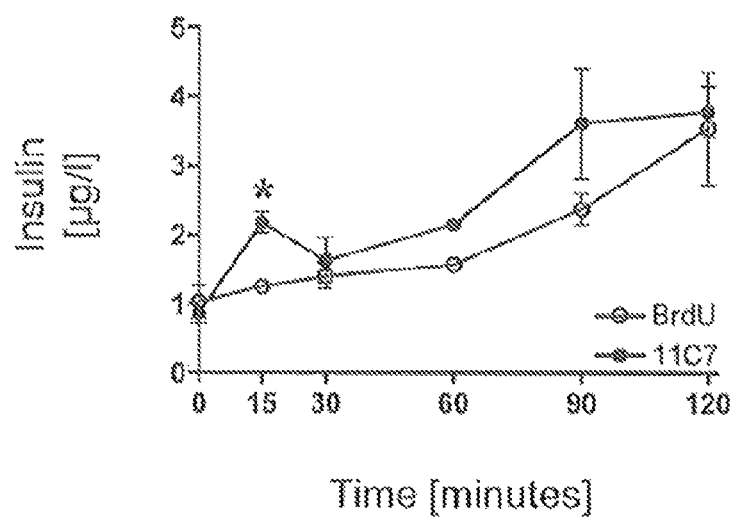
B
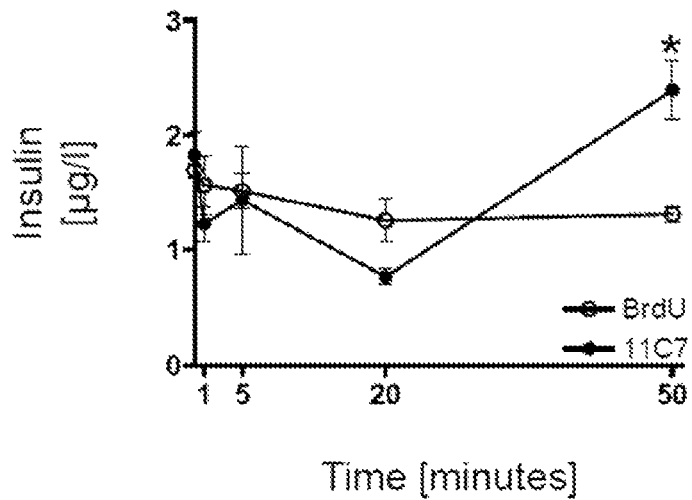
C
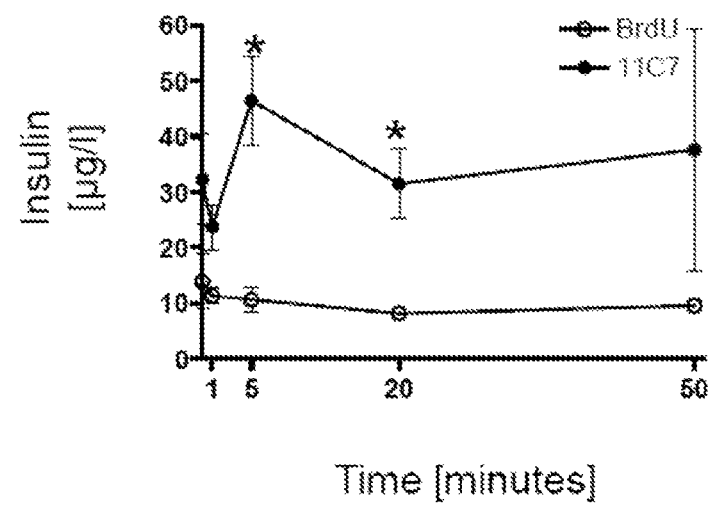
Figure 7

D
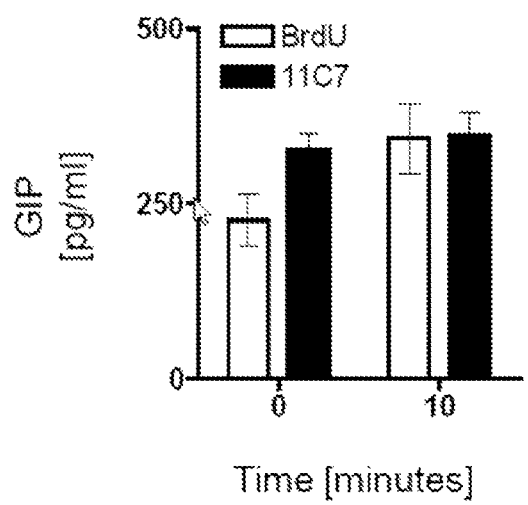
E
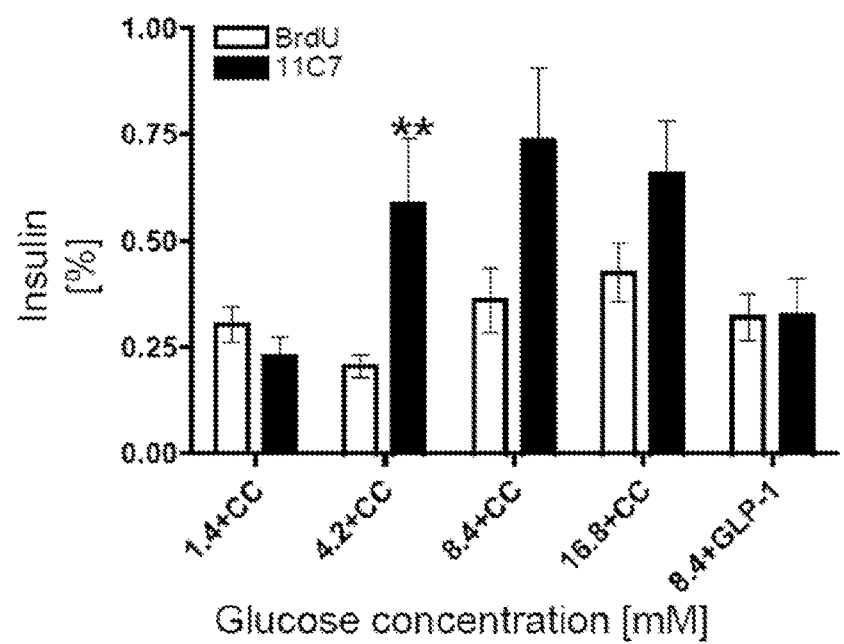
Figure 7 (continued)

USES OF NOGO-A INHIBITORS AND RELATED METHODS

CROSS-REFERENCE TO RELATED APPLICATIONS

This application is the U.S. national stage application of International Patent Application No. PCT/IB2011/053056, filed Jul. 8, 2011, which claims the benefit of U.S. Provisional Patent Application No. 61/362,876, filed Jul. 9, 2010.

The Sequence Listing for this application is labeled "SeqList.txt" which was created on Dec. 31, 2012 and is 105 KB. The entire contents of the sequence listing is incorporated herein by reference in its entirety.

FIELD OF THE INVENTION

The present invention relates to substances and compositions thereof useful in the stimulation of insulin secretion, in particular in the treatment of insulin secretion deficiency. In particular, the invention relates to substances and compositions useful in the treatment of diabetes mellitus, in particular type II diabetes.

BACKGROUND OF THE INVENTION

Insulin secretion from islet β-cells is initiated by the cholinergic parasympathetic stimulation of β-cells (the so-called "cephalic phase") and subsequently potentiated during the enteric "absorptive phase" (D'Alessio et al., 2001, *J. Clin. Endocrinol. Metab.*, 86:1253-1259). In response to mechanical and chemical sensor stimulation along the digestive tract, intestinal hormones like the incretins GLP-1 (glucagon-like peptide-1) and GIP (gastric inhibitory peptide) potentiate insulin secretion directly and indirectly, through neuronal stimulation (the "incretin effect") (Karlsson et al., 1992, *Eur. J. Pharmacol.*, 213:145-146; Balkan et al., 2000, *Am. J. Physiol. Regul. Integr. Comp. Physiol.*, 279:R1449-1454). Progressively, nutrient absorption and blood glucose rise stimulate insulin secretion directly ("post absorptive phase") (Straub et al., 2002, *Diabetes Metab. Res. Rev.*, 18:451-463). Altogether, different secretagogues act synergistically and trigger the adequate biphasic release of insulin from β-cells. These secretagogues reach islet endocrine cells through the vascular and neural networks. Pancreas innervation consists of parasympathetic and sympathetic efferent fibers, which are branches of the parasympathetic vagus nerve and the sympathetic splanchnic nerves. The vagal input stimulates insulin secretion via cholinergic (i.e. mediated by acetylcholine, Ach) or non-cholinergic mechanisms. Sympathetic postganglionic terminal nerves release noradrenaline or other peptides on endocrine cells repressing insulin and somatostatin secretion, and promoting glucagon release. The afferent sensory fibers innervate the periphery of islets and release peptides, like the calcitonin gene-related peptide (CGRP) repressing insulin secretion (Pettersson and Ahren, 1990, *Diabetes Res.*, 15:9-14).

Insulin secretion insufficiency is responsible for diabetes mellitus (DM). There are two major forms of diabetes mellitus: insulin-dependent (Type I) diabetes mellitus (IDDM) which accounts for about 5 to 10% of all cases, and non-insulin-dependent (Type II) diabetes mellitus (NIDDM or T2DM) which accounts for roughly 90% of all cases. In type I diabetes, β-cell loss is due to an autoimmune reaction. In type II diabetes, increased peripheral insulin resistance challenges the functional β-cell mass: after an initial attempt at overriding the increased insulin demand, β-cell function and number decline progressively, resulting in a large spectrum of conditions that require different prescriptions. Diabetes mellitus affects more than 150 million adults and is one of the leading causes of mortality in the world. Generally, when T2DM is diagnosed, global β-cell function is already reduced by about 50%.

Enhancement of insulin secretion in type II diabetic patients is promoted with drugs such as sulfonylureas, thiazolidinediones (TZD) or GLP-1 receptor agonists, but these treatments do not prevent β-cell exhaustion. Oral anti-diabetics (insulin sensitizers and secretagogues) are found useful during the first stages of the disease when insulin resistance predominates and an insulin pancreatic reserve is still available. However, as pancreatic impairment progresses, basal insulin level starts to be an essential parameter to control for achieving metabolic control in patients. At a later stage of T2DM progression, only a basal-bolus regimen of insulin is able to maintain homeostasis in most patients. Currently, no treatment can stably restore a physiological profile of insulin secretion, leading to diabetes progression and development of serious complications.

Therefore, there is huge heath and economical needs for the development of new treatments for managing insulin secretion insufficiency and in particular new treatment for diabetes mellitus, notably T2DM.

Nogo-A, also known as reticulon-4 or neurite outgrowth inhibitor, is a high molecular weight membrane synaptic protein mostly expressed in the central nervous system (CNS), notably in oligodendrocytes and in subsets of neurons (Chen et al., 2000, *Nature*, 403:434-439). Nogo-A expression is not restricted to the CNS, but is also found in human skeletal muscle cells (Jokic et al., 2005, *Ann. Neurol.*, 57:553-556). In the intact CNS, Nogo-A appears to have a stabilizing, growth controlling role (Montani et al., 2009, *J. Biol. Chem.*, 284: 10793-10807). Nogo-A regulates neurite growth and cell migration (Chen et al., 2000, above). In particular, Nogo-A was shown to restrict neuronal regeneration in the injured adult spinal cord and brain, and to limit plastic rearrangements and functional recovery after large CNS lesions (Schwab, 2004, *Curr. Opin. Neurobiol.*, 14:118-124; Cafferty et al., 2006, *J. Neurosci.*, 26:12242-12250). The growth inhibitory action of Nogo-A is mediated by cytoskeletal regulators, such as Rho GTPases or cofilin (Montani et al., 2009, above). Nogo-A and its receptor (NgR) are also found in synapses, where they may influence synapse stability and function (Aloy et al., 2006, *Brain Cell Biol.*, 35, 137-56).

Nogo-A antagonists have been developed to promote CNS axonal regeneration and functional recovery after spinal cord injury (EP1711530; WO2004/052932; Walmsley et al., 2007, *Current Pharmaceutical Design*, 13(24), pp. 2470-2484(15); Yang et al., 2009, *Annals of Neurology*, 999, 999A).

SUMMARY OF THE INVENTION

The present invention relates to the unexpected finding that Nogo-A knock-out mice (mice lacking 2 active Nogo-A alleles by the targeted deletion of Rtn4 exon 3) (Simonen et al., 2003, *Neuron*, 38, 201-211) challenged with different insulin secretagogues present an increased insulin secretion, resulting in a higher glucose clearance, compared with wild type controls. This effect was unexpectedly found to be associated with a stronger pancreatic parasympathetic input and with higher sensitivity of β-cells to cholinergic and GLP-1 stimulation.

A first aspect of the invention provides a Nogo-A antagonist for controlling blood glucose or blood insulin levels in a subject.

A second aspect of the invention relates a use of a Nogo-A antagonist for controlling blood glucose or blood insulin levels in a subject.

A third aspect of the invention relates a use of a Nogo-A antagonist for the preparation of a medicament for the treatment of insulin secretion deficiency, in particular insulin secretion insufficiency.

A fourth aspect according to the invention relates to a method of controlling blood glucose or blood insulin levels in a subject, said method comprising administering in a subject in need thereof an insulin secretory effective amount of a Nogo-A antagonist, or a pharmaceutical formulation thereof.

A fifth aspect of the invention relates to a method of preventing, repressing or treating insulin secretion deficiency, in particular insulin secretion insufficiency in a subject, said method comprising administering in a subject in need thereof a therapeutically effective amount of a Nogo-A antagonist, or a pharmaceutical formulation thereof.

A sixth aspect of the invention relates to a pharmaceutical formulation comprising a Nogo-A antagonist, combined with at least one co-agent useful in the stimulation of insulin secretion or the treatment of diabetes mellitus, and at least one pharmaceutically acceptable carrier.

A seventh aspect of the invention relates to a use of a Nogo-A polypeptide or a Nogo-A polypeptide fragment for the preparation of a pharmaceutical composition for controlling blood glucose levels and/or insulin blood levels in a subject, wherein said polypeptide or polypeptide fragment induces an antibody response sufficient to neutralize or antagonize endogenous Nogo-A in said subject.

An eighth aspect of the invention relates to a use of a Nogo-A polypeptide or a Nogo-A polypeptide fragment for the preparation of a pharmaceutical composition for the repression or treatment of insulin secretion deficiency in a subject, wherein said polypeptide or polypeptide fragment induces an antibody response sufficient to neutralize or antagonize endogenous Nogo-A in said subject.

A ninth aspect of the invention relates to a Nogo-A polypeptide or a Nogo-A polypeptide fragment or a pharmaceutical formulation thereof for the prevention, the repression or treatment of insulin secretion deficiency in a subject, wherein said polypeptide or polypeptide fragment induces an antibody response sufficient to neutralize or antagonize endogenous Nogo-A in said subject.

A tenth aspect of the invention provides a method for controlling blood glucose or blood insulin levels in a subject, said method comprising administering in a subject in need thereof an amount of a Nogo-A polypeptide or a Nogo-A polypeptide fragment, or a pharmaceutical formulation thereof sufficient to induce an antibody response sufficient to neutralize or antagonize endogenous Nogo-A in said subject.

An eleventh aspect of the invention provides a composition comprising a Nogo-A polypeptide or a Nogo-A polypeptide fragment, or a pharmaceutical formulation thereof that produces, when administered to a subject, an antibody response sufficient to neutralize or antagonize endogenous Nogo-A in said subject.

DESCRIPTION OF THE FIGURES

FIGS. 6A-6I show sequences disclosed in the application with their respective SEQ ID numbers.

FIGS. 7A-7E show improved insulin secretion after 2 weeks treatment with neutralizing 11C7 anti Nogo-A antibody in diabetic db/db mice as compared to db/db mice treated with anti-BrdU control antibody, as described in Example 4. A-C: Plasma insulin levels (µg/l) in different glucose tolerance tests in vivo. A: after i.p. injection of glucose (1g/kg). n=2-4, * P<0.005; B: after i.v. injection of glucose (1 g/kg) alone, n=3, * P<0.005; C: after injection of glucose (1g/kg) supplemented with the cholinergic analogue carbachol (CC) (0.53µM/kg), n=3, * P<0.05; D: Plasma gastric inhibitory polypeptide (GIP) (pg/ml) in random-fed 11C7 treated db/db mice compared to db/db mice treated with anti-BrdU control antibody. (n=5, P=NS); E:Sensitivity of (β-cells from isolated islets of 11C7 and anti-BrdU control-treated db/db mice in response to glucose supplemented with the cholinergic analogue carbachol (CC) (100µM) or glucagon-like peptide-1 (GLP-1) (100nM) ** P<0.005.

DETAILED DESCRIPTION

Figure 1:
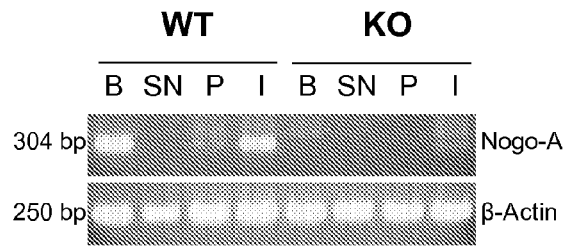
FIG. 1 shows the expression of Nogo-A in brain hemisphere (B), sciatic nerves (SN), pancreas (P) and islets (I) in 2-month-old wild-type controls (WT) and Nogo-A KO mice (KO), as assessed by RT-PCR compared to β-actin as internal control as described in Example 1. β-actin was used as internal control.

The term "insulin secretion deficiency" includes a disease or condition where pancreatic β-cells are unable to secrete sufficient insulin (insulin secretion insufficiency) and insulin secretion dysfunction such as in impaired glucose tolerance and diabetes mellitus, in particular type II diabetes. This term includes relative and absolute deficiency in response to lower insulin sensitivity.

The term "Nogo-A" or "Nogo-A polypeptide" refers to mammalian Nogo-A protein and iso forms and fragments thereof. Nogo-A is also known as reticulon-4 or neurite outgrowth inhibitor. It includes in particular human Nogo-A which can be described by an amino acid sequence as set forth in SEQ ID NO: 1. It further encompasses a protein encoded by a nucleic acid sequence as set forth in SEQ ID NO: 2. As used herein, the term Nogo-A also encompasses rat Nogo-A (SEQ ID NO: 8), bovine Nogo-A (SEQ ID NO: 9) and mouse Nogo-A (SEQ ID NO 10). As used herein, the terms Nogo-A or Nogo-A polypeptide encompass polypeptides having an amino acid sequence such as those described in Oertle et al., 2003, *The Journal of Neuroscience*, 23(13), 5393-5406, the contents of which is herein incorporated by reference in its entirety, in particular Nogo-A or Nogo-A polypeptide fragments comprising an amino acid sequence selected from the group consisting of amino acid residues 1-131 (SEQ ID NO: 3), 132-939 (SEQ ID NO: 4), 206-501 (SEQ ID NO: 5), 501-680 (SEQ ID NO: 6), 132-206 (SEQ ID NO: 7), 680-939 (SEQ ID NO: 35) and 940-1127 (SEQ ID NO: 36) of SEQ ID NO: 1. In addition, the terms Nogo-A or Nogo-A polypeptide encompass polypeptides that have a high degree of similarity or a high degree of identity with the amino acid sequence of SEQ ID NO: 1 and which polypeptides are biologically active. In particular, the terms Nogo-A or Nogo-A polypeptide encompass polypeptides substantially homologous to a protein of SEQ ID NO: 1 or an isoform or fragment thereof, e.g. which have an amino acid sequence different from that of native human Nogo-A or Nogo-A fragment because of one or more deletions, insertions or substitutions. Substantially homologous means a variant amino acid sequence that is at least 80%, at least 85%, at least 90%, at least 95%, at least 96%, at least 97%, at least 98% or at least 99% identical to the native amino acid sequences, as disclosed above. The percent identity of two amino acid or two nucleic acid sequences can be determined by visual inspection and/or mathematical calculation, or more easily by comparing sequence information using known computer program used for sequence comparison such as Clustal package version 1.83. It further encompasses polypeptides which may comprise a sequence having at least one conservatively substituted amino acid, meaning that a given amino acid residue is replaced by a residue having similar physiochemical characteristics.

The term "Nogo-A antagonist" as used herein refers to any substances that are able to totally or partially inhibit, block, attenuate, or interfere with any pathway elicited, either directly or indirectly, by Nogo-A. Thus, the term "antagonists" is intended to include, but is not limited to, molecules which neutralise the effect of Nogo-A. For example, Nogo-A antagonists include substances which interact with Nogo Receptor (NgR) and any other receptor expressed in β-cells and compete with its ligand Nogo-A. For example, Nogo-A antagonists include small molecules, peptidomimetics, chimaeric proteins, natural or unnatural proteins, nucleic acid derived polymers (such as DNA and RNA aptamers, siRNAs, PNAs, or LNAs), fusion proteins with Nogo-A antagonizing activities, antibody antagonists such as neutralising anti-Nogo-A antibodies, or gene therapy vectors driving the expression of such Nogo-A antagonists.

The term "Nogo-A antibody" as used herein refers to any antibody or variant form thereof, including but not limited to, antibody fragment, domain antibody or single chain antibody capable of selectively binding to Nogo-A protein or fragment thereof. In particular, Nogo-A antibodies include Nogo-A antibody able to bind to the epitopes of mammalian, notably human Nogo-A, in particular, epitopes localized within regions consisting of amino acid residues 1-979 (SEQ ID NO: 37), 342-357 (SEQ ID NO: 38), 544-725 (SEQ ID NO: 39), 567-748 (SEQ ID NO:40), and 610-621 (SEQ ID NO: 41) of SEQ ID NO: 1 or amino acids 101-118 of SEQ ID NO: 9 (SEQ ID NO: 42), or amino acids 623-640 of SEQ ID NO: 8 (SEQ ID NO: 43). A Nogo-A antibody includes murine, chimeric, humanised, or fully human antibodies, genetically engineered or bispecific or multispecific antibodies as well as fragments thereof such as single chain antibodies (scFv) or domain antibodies against Nogo-A protein or fragment thereof and the like. Antibodies of this invention may be monoclonal or polyclonal antibodies, or fragments or derivative thereof having substantially the same antigen specificity. The term "selectively" indicates that the antibodies preferentially recognize and/or bind the target polypeptide or epitope, i.e., with a higher affinity than to any other antigen or epitope, i.e. the binding to the target polypeptide can be discriminated from non-specific binding to other antigens. The binding affinity of an antibody can be readily determined by one of ordinary skill in the art, for example, by Scatchard analysis (Scatchard et al., 1949, Ann. N.Y. Acad., 51, 660-672).

The term "antibody antagonists" as used herein refers to any antibody or variant form thereof, including but not limited to, antibody fragment, domain antibody or single chain antibody capable of reducing the activity of a given pathway, enzyme, receptor or ligand, such as a Nogo-A pathway. Antibody antagonists include antibodies in a conventional immunoglobulin format (IgA, IgD, IgE, IgG, IgM), and also fragments thereof or any other "antibody-like" format that binds to human Nogo-A (for example, a single chain Fv fragment, a fragment Fc, a Fd fragment, a Fab fragment, a Fab' fragment, a F(ab)$_2$ fragment, chimeric antibodies, diabodies, domain antibodies (dAbs) such as described in Holliger et al., 2005, *Nature Biotechnology*,23(9), 1126-1136 and polypeptides that contain at least a portion of an immunoglobulin that is sufficient to confer specific antigen-binding to the polypeptide (e.g., inmmunoadhesins). The terms Fv, Fc, Fd, Fab, or F(ab)$_2$ are used with their standard meanings (Harlow et al., 1988, *Antibodies: A Laboratory Manual Cold Spring Harbor Laboratory Press; Dec.* 1, 1988 ISBN 978-0879693145).

The term "monoclonal antibody" as used herein refers to an antibody obtained from a population of substantially homogeneous antibodies, i.e., the individual antibodies comprising the population are identical except for possible naturally occurring mutations that may be present in some minor amounts. Monoclonal antibodies are highly specific, as being directed against a single antigenic site. The modifier term "monoclonal" indicates the character of the antibody as being obtained from a substantially homogeneous population of antibodies, and is not to be construed as requiring production of the antibody by any particular method.

The term "humanised antibody" refers to a type of engineered antibody having its CDRs derived from a non-human donor immunoglobulin, the remaining immunoglobulin being derived from one or more human or non-immunogenic to humans immunoglobulin(s). In addition, framework support residues may be altered to preserve binding affinity of the donor immunoglobulin (Queen et al., 1989, *Proc. Natl. Acad. Sci. USA*, 86:1002910032).

The term "donor antibody" refers to a non-human antibody, which contributes the amino acid sequences of its variable regions, CDRs, or other functional fragments or analogues thereof to the humanised antibody, and thereby provide the humanised antibody with the antigenic specificity and neutralising activity characteristic of the donor antibody. A suitable donor antibody may be selected by methods as described in *Handbook of Therapeutic Antibodies*. Stefan Dübel (Ed:) January 2007. ISBN: 978-3-527-31453-9.

The term "acceptor antibody" refers to an antibody heterologous to the donor antibody, which provides the amino acid sequences of its heavy and/or light chain framework regions and/or its heavy and/or light chain constant regions to the humanised antibody. The acceptor antibody may be derived from any mammal provided that it is non-immunogenic in humans. Preferably, the acceptor antibody is a human antibody. A suitable human acceptor antibody may be selected for its homology to the nucleotide and amino acid sequences of the donor antibody. For example, suitable human acceptor antibody may be found by methods as described in *Handbook of Therapeutic Antibodies*. Stefan Dübel (Ed:) January 2007. ISBN: 978-3-527-31453-9. Antibodies according to the invention can be generated by immunization of a suitable host (e.g., vertebrates, including humans, mice, rats, sheep, goats, pigs, cattle, horses, reptiles, fishes, amphibians, and in eggs of birds, reptiles and fish). Determination of immunoreactivity with an immunogenic Nogo-A polypeptide may be made by any of several methods well known in the art, including, e.g., immunoblot assay and ELISA. Modification of such antibodies into therapeutically useful derivatives may be made by methods as described in *Handbook of Therapeutic Antibodies*. Stefan Dübel (Ed:) January 2007. ISBN: 978-3-527-31453-9.

The term "CDRs" refers to the complementarity determining region amino acid sequences of an antibody which are the hypervariable regions of immunoglobulin heavy and light chains. It refers to all three heavy chain CDRs, and/or all three light chain CDRs.

The term "anti-Nogo-A antibody" may be a neutralising anti-Nogo-A antibody or a fragment thereof, such as murine antibodies 2A10 and 2C4(described in WO 2005/016544, now also identified as U.S. Pat. No. 7,780,964, the content of which is incorporated herein by reference in its entirety). The anti-Nogo-A antibody may be a humanised antibody such as a humanised variant of 2A10, for example H20L16, H28L16, H28L13 and H27L16 (as described in WO 2007/068750, now also identified as U.S. Pat. No. 8,362,208 and WO 2010/004031, now also identified as USPGPUB 2011/0268729, the contents of which are incorporated herein by reference in their entirety), a human antibody, or a fragment thereof. Amino acid sequences of the humanised constructs of the heavy chain and light chain variable region of 2A10 are presented as SEQ ID NOs: 26 to 30 herein (FIG. 6G). Full length heavy and light chain humanised variants of 2A10 are presented as SEQ ID NOs: 20 to 25 (FIG. 6F).

The anti-Nogo-A antibody may also be any of the antibodies described in WO 2004/052932, now also identified as U.S. Pat. No. 8,535,666, the content of which is incorporated herein by reference in its entirety. Examples of antibodies disclosed in WO 2004/052932 are 11C7, including humanized variants thereof. The sequence of the variable regions of 11C7 is shown in SEQ ID NOs: 31 and 32 (FIG. 6H). Human anti-Nogo-A antibodies are also described in WO 2005/028508, now also identified as US PGPUB 2009/056509, and in WO 2009/056509, now also identified as U.S. Pat. No. 8,163,285, the contents of which are incorporated herein by reference in their entirety. Specific antibodies disclosed in WO 2009/056509, also identified as U.S. Pat. No. 8,163,285, include the human antibody 6A3, having variable regions as shown in SEQ ID NOs: 33 and FIG. 6H.

In a particular embodiment, an anti-Nogo-A antibody according to the invention is a humanised anti-Nogo-A antibody such as a humanised variant of antibodies described in WO 2004/052932, now also identified as U.S. Pat. No. 8,535,666, WO 2005/061544, now also identified as U.S. Pat. No. 7,780,964, WO 2005/028508, now also identified as U.S. Pat. No. 8,535,666, WO 2007/068750, now also identified as U.S. Pat. No. 8,362,208, WO 2009/056509, now also identified as U.S. Pat. No. 8,163,285, or WO 2010/004031, now also identified as USPGPUB 2011/0268729 or a human anti-Nogo-A antibody, or a fragment thereof. Anti-Nogo-A antibodies particularly useful in the frame or a use or a method according to the present invention include humanised variants of 11C7, 2A10 or 2C4, 6A3 as described in WO 2009/056509, now also identified as U.S. Pat. No. 8,163,285, and H20L16, H27L16, H28L13 and H28L16 as described in WO 2010/004031(USPGPUB 2011/0268729). Preparation of polyclonal and monoclonal "anti-Nogo-A antibody" may be prepared by known techniques in the art, in particular as described in US 2005/0260616 or Oertle et al., 2003, above.

The term "siRNA" refers to small interfering RNA which are double stranded RNA (about 19-23 nucleotides) able to knock down or silence a targeted mRNA from a target gene. Artificial siRNAs can be either chemically synthesized as oligonucleotides or cloned into a plasmid or a virus vector (adenovirus, retrovirus or lentivirus) as short hairpin RNAs to generate a transient or stable transfection in any type of cells (Martin et al., 2007, *Ann. Rev. Genomics Hum. Genet.*, 8:81-108; Kolfschoten et al., 2007, *Nat. Clin. Pract. Endocrinol. Metab.*, 3(12):827-34; Huang et al., 2008, *Expert. Opin. Ther. Targets*, 12(5), 637-645).

The term "peptidomimetic" is defined as a peptide analog containing non-peptidic structural elements, which peptide is capable of mimicking or antagonizing the biological action(s) of a natural parent peptide. A peptidomimetic lacks classical peptide characteristics such as enzymatically scissile peptide bonds.

A Nogo-A protein, as an isolated, purified or homogeneous protein according to the invention, may be produced by recombinant expression systems as described in Chen et al., 2000, *Nature*, 403:434-439, or purified from naturally occurring CNS or skeletal muscle cells.

Suitable systems of expression of Nogo-A or Nogo-A variants or fragments, Nogo-A antagonists include transfected Chinese hamster ovary (CHO) cell line.

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history, overweight status or age; (b) inhibiting the disease, i.e., arresting its development; or relieving the disease, i.e., causing regression of the disease and/or its symptoms or conditions such as improvement or remediation of damage.

In particular, treatment of insulin secretion deficiency comprises to normalize or improve an impairment of glucose clearance through the control of blood insulin levels or insulin production.

The term "subject" as used herein refers to mammals. For example, mammals contemplated by the present invention include human, primates, domesticated animals such as cattle, sheep, pigs, horses, laboratory rodents and the like.

The term "efficacy" of a treatment or method according to the invention can be measured based on changes in the course of disease or condition in response to a use or a method according to the invention. For example, the efficacy of a treatment or method according to the invention can be measured by an increase of blood levels of insulin by ELISA or a decrease in fasting glycaemia or post-prandial glycaemia by oral glucose tolerance test (OGTT) or fasting glucose test (FPG). For another example, the efficacy of a treatment or method of the invention encompasses a higher neutrally-stimulated insulin secretion in a subject assessed by measuring the plasma insulin levels by ELISA, or by measuring the plasma C-peptide levels by ELISA, and/or a higher parasympathetic input, assessed by measuring the plasma pancreatic polypeptide (PP) levels with the Luminex® xMAP® technology (Rossi et al., 2005, Diabetes 54:1324-1330).

The term "insulin secretory effective amount" as used herein refers to an amount of at least one Nogo-A antagonist or a pharmaceutical formulation thereof according to the invention that elicits a detectable insulin secretion response in a subject that that is being administered the said Nogo-A antagonist.

The term "an antibody response sufficient to neutralize or antagonize endogenous Nogo-A" refers to a protective immune response against Nogo-A activity, e.g., an induction in the production of circulating antibodies that neutralize endogenous Nogo-A and/or an antibody response that prevents, represses or treats insulin secretion deficiency in an individual. For example, individuals in which a protective immune response has been induced can exhibit reduced insulin secretion deficiency and/or reduced risk to develop Type II diabetes as compared to non-immunized control individuals.

Nogo-A Antagonists

Nogo-A antagonists include substances described in the detailed description.

In a particular embodiment, a Nogo-A antagonist according to the invention is a neutralising anti-Nogo-A antibody.

In a further embodiment, a Nogo-A antagonist is a neutralising anti-Nogo-A antibody selected from humanised variants of mAbs 11C7, 2A10 or 2C4; or mAbs 6A3, H20L16, H27L16, H28L13 and H28L16.

In a further embodiment, a Nogo-A antagonist is a humanised variant of mAb 11C7 neutralising anti-Nogo-A antibody.

In a particular embodiment, a Nogo-A antagonist according to the invention is a siRNA with Nogo-A antagonizing activities.

Alternatively, Nogo-A antagonists can be generated in-vivo in the form of autoantibodies, through the administration of a Nogo-A polypeptide or fragment thereof or a pharmaceutical composition thereof capable of inducing an antibody response sufficient to neutralize or antagonize endogenous Nogo-A in a subject. In this case, either intact Nogo-A, fragments thereof, or preferably synthetic peptides corresponding to epitopes of Nogo-A, could be used as immunogens to elicit an immune response and the production of neutralising autoantibodies against endogeneous Nogo-A in a subject suffering from insulin secretion deficiency. Therapeutic levels of circulating neutralising anti-NogoA autoantibodies could be maintained and controlled by appropriate immunization / booster protocols. A useful precedent is the use of immunization against certain endogenous fertility hormones such as LHRH (luteinizing hormone releasing hormone) and hCG (human chorionic gonadotropin) as methods of fertility regulation, contraception (Talwar, 1997,*Human Reproduction Update,* 3(4), 301-310; Talwar et al., 1994, *Proc. Natl. Acad. Sci. USA.,* 91, 8532-8536; Amato et al., 2002, J. Clin. *Endocr. & Metab.,* 87(3), 993-997) and treatment of hormone-dependant cancers (Conry et al., 2000, *Clinical Cancer Research,* 6, 34-41). These methods described in the above references hereby incorporated by reference in their entirety have been proven both effective and reversible in clinical trials. According to another aspect, is provide a composition comprising a Nogo-A polypeptide or fragment thereof capable to induce an antibody response sufficient to neutralize or antagonize endogenous Nogo-A in a subject.

Compositions

The invention provides Nogo-A antagonists, Nogo-A polypeptide or fragment thereof, pharmaceutical compositions thereof, and methods for treating a patient, preferably a mammalian patient, and most preferably a human patient who is suffering from a medical disorder selected from insulin secretion deficiency, in particular diabetes mellitus such as type II diabetes.

According to another aspect, the invention provides Nogo-A antagonists, pharmaceutical compositions thereof and methods for controlling the glucose and/or insulin blood levels in a subject.

In a particular embodiment, the invention provides a pharmaceutical formulation according to the invention for use as a medicament.

Pharmaceutical compositions of the invention can contain at least one Nogo-A antagonist according to the invention in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to a particular embodiment, compositions according to the invention are injectable.

Compositions of this invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Further materials as well as formulation processing techniques and the like are set out in *Part 5 of Remington's Pharmaceutical Sciences, 21$^{st}$ Edition,* 2005, University of the Sciences in Philadelphia, Lippincott Williams & Wilkins, the content of which is incorporated herein by reference.

Compositions of this invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions of this invention may also be formulated for inhalation, which may be in a form including, but not limited to, a solution, suspension, or emulsion that may be administered as a dry powder or in the form of an aerosol using a propellant.

The compounds of this invention can also be administered in sustained release forms or from sustained release drug delivery systems. A description of representative sustained release materials can also be found in the incorporated materials in *Remington's Pharmaceutical Sciences*. In a particular embodiment, when the Nogo-A antagonist according to the invention is a siRNA, it may be advantageously delivered in encapsulated form into nanoparticles or liposomes such as described in Fenske et al., 2008, *Expert Opin, Drug Deliv.,* 5(1), 25-44; de Fougerolles, 2008, *Hum. Gene Ther.,* 19(2), 125-32; Huang et al., 2008, above, the content of which is herein incorporated by reference in their entirety.

In a particular aspect, the composition to be administered to a subject in order to induce an antibody response sufficient to neutralize or antagonize endogeneous Nogo-A may, optionally, contain an adjuvant and may be delivered in any manner known in the art for the delivery of immunogen to a subject.

Mode of Administration

Compositions of this invention may be administered in any manner including intravenous injection, intraperitoneal injection, subcutaneous injection, oral route, cutaneous application or combinations thereof.

Combination

According to the invention, the Nogo-A antagonist, the Nogo-A polypeptide or fragment thereof used to generate Nogo-A auto-antibodies, and pharmaceutical formulations thereof can be administered alone or in combination with a co-agent useful in the stimulation of insulin secretion or in the treatment of insulin deficiency and/or diabetes mellitus, such as substances useful for treating, stabilizing, preventing, and/or delaying insulin deficiency e.g. for example a co-agent selected from sulfonylureas (for example those described in Campbell, 2009, *Diabetic Hypoglycemia,* 2(1), 3-10), thiazolidinediones (TZD) (for example those described in Koyama et al., 2003, *Bioorg. Med. Chem. Lett.,* 13, 1801-1804) or GLP-1 receptor agonists (for example exenatide, liraglutide or lixisenatide or those described in Knudsen et al., 2007, *PNAS,* 104(3), 937-942).

The invention encompasses the administration of a Nogo-A antagonist and pharmaceutical formulations thereof, or of a Nogo-A polypeptide or fragment thereof used to generate Nogo-A auto-antibodies, wherein the Nogo-A antagonist or pharmaceutical formulation thereof, or the Nogo-A polypeptide or fragment thereof used to generate Nogo-A auto-antibodies, is administered to an individual prior to, simultaneously or sequentially with other therapeutic regimens or co-agents useful in the stimulation of insulin secretion or in the treatment of insulin deficiency and/or diabetes mellitus (e.g. multiple drug regimens), in a therapeutically effective amount. A Nogo-A antagonist or the pharmaceutical formulation thereof or the Nogo-A polypeptide or fragment thereof used to generate Nogo-A auto-antibodies, that is administered simultaneously with said co-agents can be administered in the same or different composition(s) and by the same or different route(s) of administration.

According to one embodiment, is provided a pharmaceutical formulation comprising a Nogo-A antagonist, combined with at least one co-agent useful in the stimulation of insulin secretion or in the treatment of a disease or a disorder characterized by insulin deficiency, and at least one pharmaceutically acceptable carrier.

According to another embodiment, is provided a pharmaceutical formulation according to the invention wherein the Nogo-A antagonist is a neutralising anti-Nogo-A antibody.

In a further embodiment, is provided a pharmaceutical formulation according to the invention, wherein the Nogo-A antagonist is a neutralising anti-Nogo-A antibody selected from humanised variants of mAbs 11C7, 2A10 or 2C4; or mAbs 6A3, H20L16, H27L16, H28L13 and H28L16.

In a further embodiment, is provided a pharmaceutical formulation according to the invention, wherein the Nogo-A antagonist is a humanised variant of mAb 11C7 neutralising anti-Nogo-A antibody.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients

In an embodiment, patients according to the invention are patients suffering from a disorder selected from insulin secretion deficiency and insulin resistance.

In a further embodiment, patients according to the invention are patients suffering from insulin secretion deficiency.

In another further embodiment, patients according to the invention are suffering from diabetes mellitus.

In another further embodiment, patients according to the invention are suffering from type II diabetes.

Use According to the Invention

In one embodiment of the invention is provided a use of a Nogo-A antagonist for the preparation of a pharmaceutical composition for controlling blood glucose levels and/or insulin blood levels in a subject.

In another embodiment of the invention is provided a use of a Nogo-A antagonist for the preparation of a pharmaceutical composition for the repression or treatment of insulin secretion deficiency.

In a further embodiment, is provided a use of a Nogo-A antagonist for the preparation of a pharmaceutical composition for the prevention, the repression or treatment of diabetes mellitus.

In a further embodiment, is provided a use of a Nogo-A antagonist for the preparation of a pharmaceutical composition for the prevention, the repression or treatment of type II diabetes.

In another embodiment of the invention is provided a method for controlling blood glucose or blood insulin levels in a subject, said method comprising administering in a subject in need thereof an insulin secretory effective amount of a Nogo-A antagonist, or a pharmaceutical formulation thereof.

In another embodiment of the invention is provided a use of a Nogo-A polypeptide or a Nogo-A polypeptide fragment, typically a synthetic polypeptide corresponding to epitopes of Nogo-A, for the preparation of a pharmaceutical composition for controlling blood glucose levels and/or insulin blood levels in a subject, wherein said polypeptide or polypeptide fragment induces an antibody response sufficient to neutralize or antagonize endogeneous Nogo-A in said subject.

In another embodiment of the invention is provided a use of a Nogo-A polypeptide or a Nogo-A polypeptide fragment, typically a synthetic polypeptide corresponding to epitopes of Nogo-A, for the preparation of a pharmaceutical composition for the repression or treatment of insulin secretion deficiency in a subject, wherein said polypeptide or polypeptide fragment induces an antibody response sufficient to neutralize or antagonize endogeneous Nogo-A in said subject.

In a further embodiment, is provided a use of a Nogo-A polypeptide or a Nogo-A polypeptide fragment for the preparation of a pharmaceutical composition for the prevention, the repression or treatment of diabetes mellitus.

In a further embodiment, is provided a use of a Nogo-A polypeptide or a Nogo-A polypeptide fragment for the preparation of a pharmaceutical composition for the prevention, the repression or treatment of type II diabetes.

In another embodiment of the invention is provided a method for controlling blood glucose or blood insulin levels in a subject, said method comprising administering in a subject in need thereof an amount of a Nogo-A polypeptide or a Nogo-A polypeptide fragment, or a pharmaceutical formulation thereof sufficient to induce an antibody response sufficient to neutralize or antagonize endogeneous Nogo-A in said subject.

In a further embodiment of the invention is provided a use or a method according to the invention, wherein the subject is displaying signs or symptoms of a condition involving insulin secretion deficiency.

In another further embodiment of the invention is provided a use or a method according to the invention, wherein the subject is suffering from diabetes mellitus.

In another further embodiment of the invention is provided a use or a method according to the invention, wherein the subject is suffering from type II diabetes.

In a further embodiment of the invention is provided a use or a method according to the invention, wherein the subject is predispose to develop insulin secretion deficiency for example based on familial history, overweight status or age.

In another embodiment, is provided a use or a method according to the invention, wherein the Nogo-A antagonist is a neutralising anti-Nogo-A antibody.

In a further embodiment, is provided a use or a method according to the invention, wherein the Nogo-A antagonist is a neutralising anti-Nogo-A antibody selected from humanised variants of mAbs 11C7, 2A10 or 2C4; or mAbs 6A3, H20L16, H27L16, H28L13 and H28L16.

In a further embodiment, is provided a use or a method according to the invention according to the invention, wherein the Nogo-A antagonist is a humanised variant of mAb 11C7 neutralising anti-Nogo-A antibody.

Compounds and compositions according to the invention may be useful in the control of blood glucose or blood insulin levels in a subject. In a particular embodiment, compounds and compositions according to the invention may be useful in the repression or treatment of insulin secretion deficiency. In another particular embodiment, compounds and compositions according to the invention may be useful in the repression or prevention or treatment of diabetes mellitus such as type II diabetes.

Examples illustrating the invention will be described hereinafter in a more detailed manner and by reference to the embodiments represented in the Figures.

EXAMPLES

The following abbreviations refer respectively to the definitions below:
bp (base paired), h (hour), i.v. (intravenous), l (liter), kb (kilobase), µg (microgram), mmol (millimol), mg (milligram), µM (micromolar), ng (nanogram), pg (picogram), BrdU (5-bromo-2'-deoxyuridine), BSA (Bovine serum albumin), CC (carbachol), cDNA (complementary DNA), CGRP (Calcitonin Gene-Related Peptide), ELISA (Enzyme-linked immunosorbent assay), GFAP (Glial Fibrillary Acidic Protein), GIP (gastric inhibitory peptide), GLP-1 (Glucagon-like peptide 1), KO (knock-out), KRBH (Krebs-Ringer bicarbonate HEPES), PFA (Paraformaldehyde), PBS (Phosphate saline buffer), PCR (Polymerase Chain Reaction), PP (pancreatic polypeptide), PVA (Polyvinyl alcohol), RIA (Radioimmunoassay), RT (reverse transcriptase), VMAT2 (Vesicular Monoamine Transporter 2), WT (wild-type).

Example 1

Nogo-A Expression in the Endocrine and the Neural Components of the Pancreas

The expression pattern of Nogo-A was investigated in brain, sciatic nerves, pancreas and isolated islets, in Nogo-A −/− (KO mice) and control C57BL/6J mice, as follows.

In the adult mouse pancreas, the expression of Rtn4 (Nogo-A transcript) was detected by RT-PCR as described below (FIG. 1). Expression levels of Nogo-A in extracts from isolated islets of Langerhans were as high as in brain extracts (FIG. 1). Nogo-A expression in human and rat islets was also observed where Nogo-A protein was exclusively expressed in β-cells and in a subset of PP-cells, while it was absent from α-and δ-cells. Nogo-A was also detected in neurons and fibers of intra-pancreatic ganglia, more specifically, in the parasympathetic cell bodies but not in parasympathetic vesicular acetylcholine transporter (VAChT) fibers. Nogo-A was also found in afferent calcitonin gene-related peptide (CGRP) sensory fibers but not in sympathetic neurons positive for vesicular monoamine transporter (VMAT2), or in supporting glial fibrillary acidic protein (GFAP)-expressing Schwann cells.

These results support the unexpected finding that Nogo-A is expressed in β-cells and in neuronal cells influencing insulin secretion, namely, parasympathetic ganglia and sensory CGRP fibers.

Nogo-A −/− Knock-Out Mice

Nogo-A −/− knock out (KO) mice have been generated as described in Simonen et al., 2003, *Neuron*, 38:201-211.

Backcrossed in pure C57BL/6J background, male Nogo-A KO mice were compared with sex matched and age matched C57BL/6J animals. Genotyping was performed by PCR from genomic DNA isolated from tail biopsies using M58 of SEQ ID NO: 11: TGCTTTGAATTATTCCAAGTAGTCC and M101 of SEQ ID NO 12: AGTGAGTACCCAGCTGCAC primers for WT Nogo-A allele (1.4 kb band), M58 and M63 of SEQ ID NO 13: CCTACCCGGTAGAATATCGATAAGC primers for Nogo-A deleted allele (1.2 kb band).

RT-PCR

Total RNA from brain hemisphere (B), sciatic nerve (SN), pancreas (P) and isolated islets (I) of C57BL/6J control mice were extracted with the RNeasy mini kit (Qiagen) and RNeasy micro kit (Qiagen), respectively. cDNA were prepared using Superscript II RT kit (Invitrogen), and thereafter PCR was performed with the Red Taq kit (Sigma) and primers: Nogo-A CCTCTCTGGCAATTCTCTCTAGAAG (SEQ ID NO: 14) and AGGGGCTCGGGCTCAGTGG (SEQ ID NO: 15), Nogo-B CTGAACCAATTCCTCTGATATGGC (SEQ ID NO: 16) and AGGGGCTCGGGCTCAGTGG (SEQ ID NO: 17), Nogo-C TGCTGGAGGGCAGATCGTGGC (SEQ ID NO: 18) and CTGAACCAATTCCTCTGATATGGC (SEQ ID NO: 19).

Example 2

Increased Insulin Secretion and Decreased Glycemia in Nogo-A Knock-Out Mice

Insulin secretion profile was studied in adult Nogo-A KO males and sex- and age-matched C57BL/6J controls (WT) (described in Example 1) as described below.

Blood Glucose & Insulin Release

Figure 2:
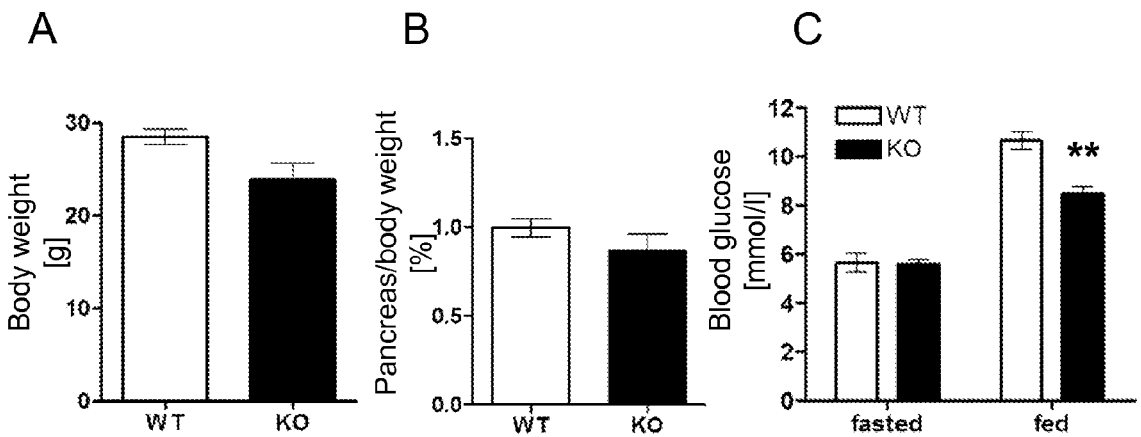
FIGS. 2A-2E show metabolic profile of Nogo-A KO mice (KO) compared to wild-type (WT) as described in Example 2. A: Body weight, n=10, P=NS; B: pancreatic weight, n=5, P=NS; C: Blood glucose in fasted and random fed conditions, n=5-6, P<0.001; D: Plasma insulin in fasted and random fed conditions, n=5-6, P<0.05; E: Plasma glucagon in fasted and random fed conditions, n=5-6, P=NS.

Two-month-old KO animals were slightly leaner than controls (body weight: WT 28.47±0.86 g, KO 23.82±1.89 g; n=10, P=0.07), despite a normal pancreas-to-body weight ratio (WT 0.99±0.05%, KO 0.86±0.09%; n=5, P=NS) (FIGS. 2A-B). Plasma glucose, insulin and glucagon levels in fasted and random fed conditions were measured as described below. After 16-hour fasting, glucose, insulin and glucagon values were normal in KO mice but in random fed condition (a period during which insulin secretion is stimulated by glucose, gluco-incretins and neurotransmitters), KO animals had significantly lower blood glucose levels (WT 10.66±0.35 mmol/l, KO 8.48±0.31 mmol/l; n=5, P<0.005), higher plasma insulin levels (WT 0.50±0.02 µg/l, KO 1.23±0.28 µg/l; n=6, P<0.05), and normal plasma glucagon levels (WT 60.79±4.62 pg/l, KO 66.54±13.29 pg/l; n=6, P<0.05) (FIG. 2C-E). These results show that Nogo-A KO mice exhibit a lower glycemia associated with a higher insulin secretion after feeding.

In Vivo Stimulation of β-Cell Secretion

Figure 3:
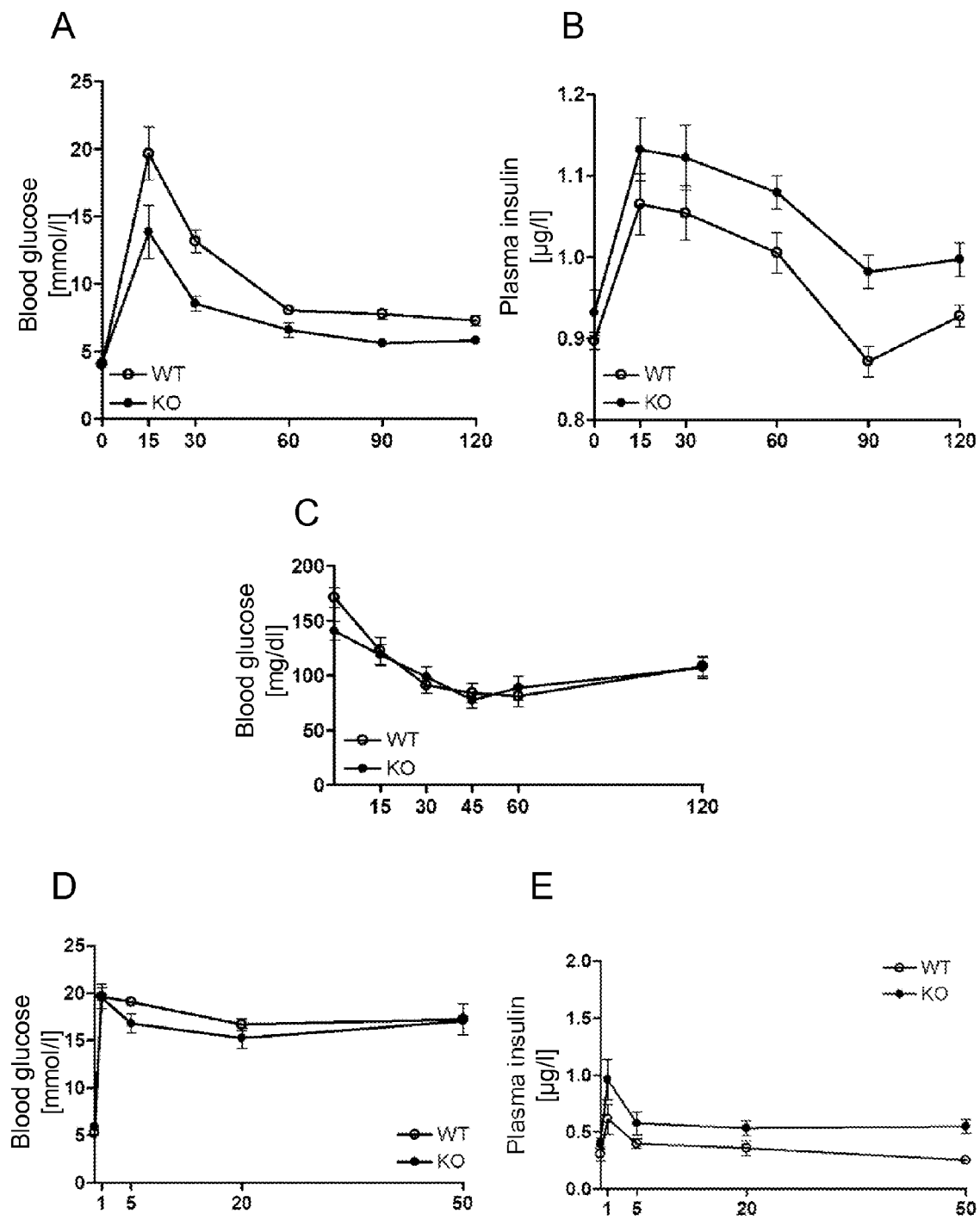
FIGS. 3A-3G show insulin secretion response to glucose alone or supplemented with the cholinergic analogue carbachol in Nogo-A KO mice compared to wild-type (WT) as described in Example 2. A: Blood glucose after i.p. injection of glucose (2g/kg); B: Plasma insulin during i.p. glucose tolerance test; C: Blood glucose after i.p. injection of insulin (0.5U/kg); D: Blood glucose and plasma insulin (E) after i.v. injection of glucose (1g/kg); F: Blood glucose and plasma insulin (G) after i.v. injection of glucose (1g/kg) supplemented with the cholinergic analogue carbachol (0.53µM/kg). n=5-6, * P<0.05, ** P<0.005.

Intraperitoneal glucose tolerance tests as described below (i.p.-GTT) showed that Nogo-A KO animals have an improved glucose clearance after glucose administration (2 g/kg) (WT 709.875±72.73 mmol/l/min, KO 378.95±31.17 mmol/1/min; n=4, P=0.006) (FIG. 3A). The stimulated insulin secretion was significantly higher 1 hour after glucose injection in Nogo-A KO animals (FIG. 3B). Insulin sensitivity assessed by measuring the blood glucose after i.p. injection of insulin (0.5 U/kg) being comparable in KO and WT mice (FIG. 3C), the faster glucose clearance in the former was due to a higher insulin secretion. Nogo-A KO mice were exposed to a bolus of glucose (intravenously, 1 g/kg) (FIG. 3D,E) after overnight fasting, while a vagal stimulation was mimicked with carbachol, a cholinergic analogue (FIG. 3F,G). While controls and KO mice corrected similarly the induced hyperglycemia by secreting comparable amounts of insulin (FIG. 3D-E), Nogo-A KO mice supplemented with carbachol (0.53 µM) corrected better the induced glycemia, in association with an improved insulin secretion (FIG. 3F,G).

All together, these results support that in a context of a down-regulation of Nogo-A activity, the cholinergic stimulation of β-cells has a more potent effect on insulin secretion.

Insulin Content Per β-Cell

Figure 5:
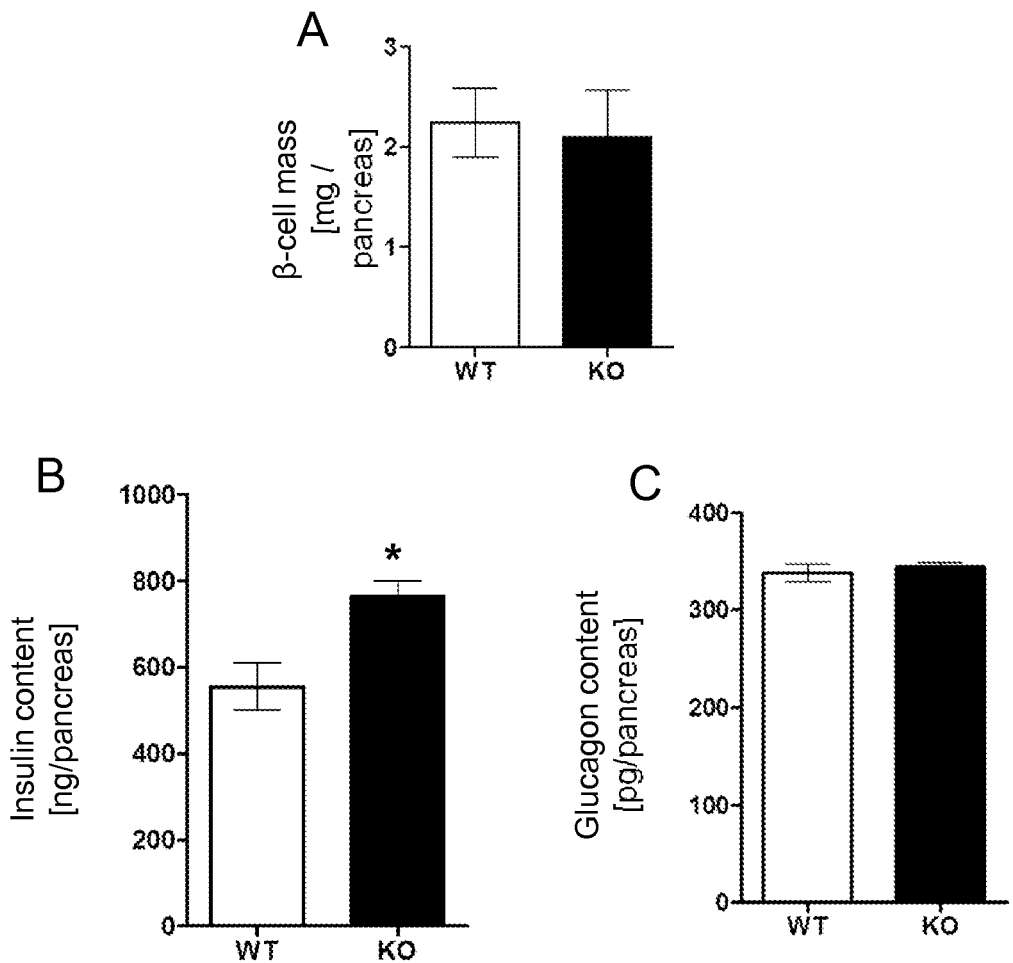
FIGS. 5A-5C show increased insulin content of Nogo-A KO pancreas exibiting normal β-cell mass as compared to wild-type (WT) as described in Example 2. A: β-cell mass, n=3, P=NS; B: Insulin content, n=4, P<0.05; C: Glucagon content, n=10, P=NS.

The morphology of the pancreatic endocrine compartment was studied as described below. The gross histology of Nogo-A KO pancreas, as well as the islet architecture was comparable to that of controls. The islet cell mass was not modified in Nogo-A KO animals. The β-cell mass was also comparable to that of controls (FIG. 5A). Nevertheless, even in absence of β-cell hypertrophy, the pancreatic insulin content assessed by ELISA as described below was 1.2 fold increased (WT 554.65±54.54 ng, KO 763.51±37.67 ng, n=5, P<0.05) (FIG. 5B), suggesting an augmented insulin content per β-cell. The total pancreatic glucagon content was unchanged (WT 338.07±8.92 pg, KO 344.02±4.96 pg; n=9-11, P=NS) (FIG. 5C).

Parasympathetic Input & β-Cell Sensitivity

Along the food ingestion and digestion process, β-cells secrete insulin in response to different secretagogues. These initiate and then potentiate insulin release. Additionally, during the enteric phase, insulin secretion is promoted by the gluco-incretins GIP and GLP-1 released from enteroendocrine cells at stimulatory glucose concentrations.

In order to challenge simultaneously the parasympathetic input as well as the β-cell sensitivity in vivo, the vagally-stimulated insulin secretion was investigated after intravenous injection of 2-deoxy-D-glucose (2DG) (984 mg/kg), a non-metabolizable glucose analogue that blocks intracellular glucose utilization. Competing with D-glucose, 2DG activates the autonomic nervous system through central neuroglycopenia.

In order to assess indirectly the parasympathetic input on islets of Langerhans, the plasma pancreatic polypeptide (PP) levels that are known to be strictly controlled by parasympathetic stimulus, were measured after overnight (ON) fasting, prior and after 2DG i.v. injection as described below. Whereas the plasma PP levels were not different between the two groups before 2DG injection, 30-minutes later, the plasma PP levels of Nogo-A KO animals were higher than those of WT controls (30': WT 101.08±11.45, KO 187.09±15.33, n=4, P=0.006), indicating that the parasympathetic input was increased (FIG. 4A).

In order to assess the gluco-incretin input, the plasma levels of GIP and GLP-1, were measured in fed conditions, prior and after 2DG injection. GLP-1 levels were undetectable in normal random fed conditions as previously reported (Althage et al., 2008, *J. Biol. Chem.*, 283:18365-18376). Therefore, GIP plasma levels were considered representative of the gluco-incretin input. In fed condition, Nogo-A KO plasma GIP values were lower in Nogo-A KO mice, irrespective of 2DG treatment (0': WT 58.05±4.90 pg/ml, KO 34.86±3.03 pg/ml, P=0.007; 15':WT 51.90±4.65 pg/ml, KO 36.55±4.19 pg/ml, P=0.04; n=5) (FIG. 4B), which correlates with lower glycemia observed in random fed Nogo-A KO animals (FIG. 2C).

Figure 4:
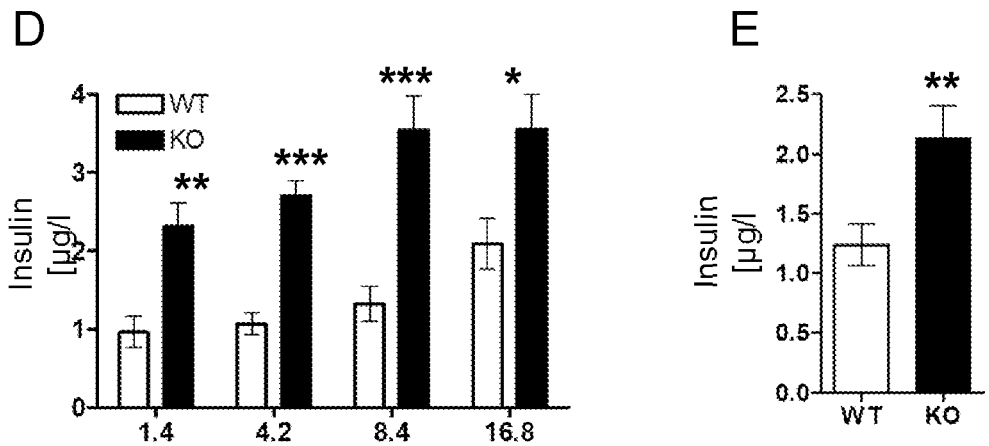
FIGS. 4A-4E show higher parasympathetic input in Nogo-A KO mice after 2-deoxy-D-glucose (2DG) (984 mg/kg)-induced neuroglycopenia compared to wild-type (WT) as described in Example 2 and sensitivity of β-cells from isolated WT and Nogo-A KO islets, as described in Example 3. A: plasma PP levels in fasted state, n=5, P<0.006; B: plasma GIP in random fed state, n=5, * P<0.05, ** P<0.008; C-E Sensitivity of β-cells from isolated WT and Nogo-A KO islets, in response to glucose only (C), n=16 batches of 10 islets, 4 mice, P=NS, in response to glucose supplemented with CC (10 µM) (D), n=15 batches of 10 islets, 4 mice, * P<0.05,  P<0.005, *P<0.001, in response to glucose 8.4 mM supplemented with GLP-1(100 nM), n=15 batches of 10 islets, 3 mice, P=0.009 (E).

Sidestepping the incretin effect, the i.v. injection of 2DG did not affect GIP plasma levels of both groups (FIG. 4B).

Together, these results show that i) the incretin effect is unaltered in Nogo-A KO mice, and ii) the pancreatic parasympathetic input is higher, which suggests that the vagal stimulation of insulin secretion is promoted in absence of Nogo-A.

In Vivo Insulin Secretion Assays

For intraperitoneal (i.p.) glucose tolerance tests, overnight fasted animals (n=10) received an i.p. glucose injection (2 g/kg) (Sigma) and blood was collected from the tail vein at 0, 15, 30, 60, 90 and 120 min into centrifuge tubes treated with lithium heparin. For intravenous glucose tolerance test, overnight fasted animals (n=7) were injected in the retro-orbital, intra-bulbar capillary plexus a glucose injection (1 g/kg), optionally supplemented with carbachol (0.53 µM) (Sigma). After isoflurane-induced brief anesthesia, mice blood samples were collected from the retroorbital plexus at 0, 1, 5, 20 and 50 min into centrifuge tubes treated with lithium heparin. Blood glucose was assessed with Glucometer Dex2 (Bayer Corporation). Glycemic areas under the curves (AUCs) were measured from time 0 to 120 min, after subtraction of basal glycaemia. After immediate centrifugation, plasma was separated and insulin levels assessed with Ultrasensitive Rat Insulin ELISA kit (Mercodia). After distribution of 25 µl of assay buffer in all wells, 5 µl of standards or samples were added, followed by the further addition of 50 µl of peroxydase-conjugated monoclonal anti-insulin antibody. After a 2-hour incubation at room temperature, wells were washed 6 times with 350 µl of Wash buffer. Then, 200 µl of TMB substrate buffer were added, followed by a 30 min incubation time, stopped by 50 µl of Stop solution and absorbance was measured at 450 nm.

Insulin Tolerance Tests

Animals fasted for 6 hours were intraperitoneally injected with recombinant human insulin (0.5 unit/kg) (Actrapid, Novo Nordisk) and blood glucose was measured from the tail vein at 15, 30 45, 60 and 120 min.

Vagally Stimulated Islet Hormone Secretion

For vagal stimulation of islet hormone secretion, 2-deoxy-D-glucose (2DG) (Sigma) was injected intravenously (984 mg/kg) in 2-month-old adult WT and Nogo-A KO mice (n=5). For PP, mice were fasted overnight and blood samples were collected at 0, 15 and 30 min (Rossi et al., 2005, Diabetes, 54, 1324-1330). For GLP-1 and GIP, mice were kept fed and blood samples were collected at 0 and 10 min (Rossi et al., 2005, above). Blood samples were collected from the retro-bulbar intra-bulbar capillary plexus, into chilled tubes treated with EDTA. For plasma GLP-1 and GIP measurements, according to the manufacturer's protocol, DPP IV inhibitor (Millipore) was added in tubes and blood samples were immediately processed. Plasma was assayed for total GIP, GLP-1 and PP using a MILLIPLEX mouse gut hormone kit (#MGT-78K) (Millipore) and the Bioplex (Bio-Rad) at the Mouse Metabolic Evaluation Facility (MEF, Center for Integrative Genomics, University of Lausanne, Switzerland.

Immunofluorescence and Immunohistochemistry

Collected pancreata were weighted and then rinsed in cold PBS and fixed O/N at 4° C. in PAF 4%. Tissues were dehydrated, embedded in paraffin and sectioned at 5 µm using a microtome. The primary antibodies used for immunostainings were: mouse anti-glucagon (Sigma Cat. No. G2654; 1/1000), guinea pig anti-insulin (Dako Cat. No. IR002; 1/400), rabbit anti-PP (Bachem Cat. No. T-4088; 1/200), rabbit anti-somatostatin (DakoCat. No. A0566; 1/200), rabbit anti-GFAP (Dako Cat. No. IR524; 1/1000), rabbit anti-CGRP (Sigma Cat. No. C8198; 1/1000), rabbit anti-VMAT2 (Phoenix Pharmaceuticals Cat. No. H-V004; 1/100) and rabbit anti-VAChT (Phoenix Pharmaceuticals Cat. No. H-V006; 1/100).

For immunohistochemistry, dewaxed and rehydrated sections were permeabilized in 0.1% TritonX-100, washed and blocked in 3% BSA, 0.1% Tween in PBS. The primary antibodies were incubated overnight. After washing in PBS, sections were incubated with specific secondary antibodies coupled to either Alexa 488 (Molecular Probes) or Cy3 (Jackson Immunoresearch). Both islet cell mass and β-cell mass were assessed by measuring the endocrine synaptophysin-positive area, or the insulin-positive area, on 4 different sections, separated by 200 µm each (n=3), multiplied by the pancreas weight. Specimens were mounted in PVA and examined with a Leica confocal microscope (DM 5500). Tissue surface and cell numbers were measured with NIH Image J 1.60 software.

Protein Extraction and Hormone Content Measurements

Pancreas collected for hormone measurement were homogenized in 5 ml (n=5-11) of acid-ethanol solution (74% ethanol, 1.4% HCl). Samples were sonicated and centrifuged. The supernatants were submitted to immunoassay experiments using either Glucagon RIA kit (Linco) or Ultrasensitive Rat Insulin ELISA kit (Mercodia) for glucagon and insulin content measurements, respectively.

Example 3

In Vitro Sensitivity of β-Cells to Insulin Secretagogues

The responsiveness of β-cells to various secretagogues (namely carbachol and GLP-1) was assayed in vitro on isolated islets as described below.

Insulin secretion was increased in isolated Nogo-A KO islets in response to glucose supplemented with carbachol (CC; 100 nM), as compared with control islets (FIG. 4D). Islets were incubated with glucose (8.4 mM) supplemented with GLP-1. Again, insulin secretion was higher when Nogo-A was absent (WT 1.23±0.17, KO 2.13±0.27; n=11-14, $P<0.01$; FIG. 4E).

In conclusion, the constitutive inactivation of Nogo-A conferred to metabolically healthy Nogo-A KO animals the ability to correct faster and more efficiently an induced hyperglycemia thanks to an improved insulin secretion. The higher insulin secretion of Nogo-A KO β-cells resulted from a higher parasympathetic input on β-cells and a higher sensitivity of β-cells to the cholinergic agonist carbachol and the glucoincretin GLP-1.

Together, these findings suggest that selective inhibition of Nogo-A could be a novel therapeutic approach to promote stimulated insulin secretion, notably in the treatment of conditions or disorders that can be alleviated by an enhanced pancreatic β-cell insulin secretion such for example the treatment of diabetes mellitus such as in type II diabetic patients.

In Vitro Insulin Secretion Assays

After mice sacrifice, the abdomen was opened and the pancreas exposed. After clamping at the porta hepatis, the main pancreatic duct was cannulated with a butterfly-27G needle and retrogradually injected with 2 ml of collagenase XI (2 mg/ml in HBSS) (Sigma). After dissection, the pancreas was digested in 3 ml of collagenase XI solution for 15 min at 37° C., and finally disrupted upon vigorous tube shaking Islets were then purified on a Histopaque 1119 (Sigma) gradient, washed thrice with Hanks 1×BSA 0.1%, and finally fished twice. Batches of 10 islets were pre-incubated for 30 min in 1 ml KRBH supplemented with BSA 0.1% and 1.4 mM glucose at 37° C. Then, the supernatant was replaced by 0.5 ml KRBH supplemented with BSA 0.1% and glucose 1.4 mM, 2.8 mM, 4.2 mM, 8.4 mM and 16.8 mM was added for another 30 min at 37° C. (n=3-4). Additionally, islets incubated for 30 min in 0.5 ml KRBH containing glucose, BSA 0.1% and another secretagogue, carbachol 10 µM (Sigma) or GLP-1 100 nM (Bachem) (n=3-4). Secreted insulin (µg/l) in the supernatant was measured with Ultrasensitive Rat Insulin ELISA kit (Mercodia). Similar insulin contents between islet batches were assessed after removal of the supernatant and acid-ethanol extraction.

Example 4

Nogo-A Neutralization by a Nogo-A Antagonist

The beneficial effects of an acute neutralization of Nogo-A by intraperitoneal or intravenous administration of a Nogo-A antagonist to promote insulin secretion is assayed in the following in early type II diabetic animals, homozygous mutants for the leptin receptor gene (db/db).

Young 5-week-old diabetic db/db animals in a C57BL/Ks background are treated with Nogo-A antagonist (anti-Nogo-A antibody 11C7 as described above) by intraperitoneal injection (4'900 ng antibody) or intravenously in the retro-orbital capillary plexus, twice over a two-week period and a control anti-BrdU antibody. This anti-Nogo-A antibody 11C7 was earlier described for its ability, when administered intrathecally to CNS, of inhibiting Nogo-A and allowing an enhanced sprouting and regrowth of lesioned axons after spinal cord injury and stroke in adult rats (Caroni et al., 1988, Neuron., 1:85-96). One week after the second injection, the insulinemia, the glucose levels and body weight of treated random fed db/db mice are compared to that of the control group: the insulinemia of db/db fed mice treated with 11C7 tended to be higher compared to the db/db mice treated with control antibody (BrdU 13.94±5.02, 11C7 32.28±8.14, n=3 mice per group, P=NS), but no effect was detected on glucose levels or body weight, most probably due to high insulin resistance of peripheral tissues (data not shown).

After the 2 weeks treatment, db/db animals are submitted to different challenges in vivo as previously described (namely i.p.-GTT, glucose-induced insulin secretion by intravenously a bolus of glucose (1 g/kg), optionally supplemented with carbachol CC)). Plasma insulin levels and total pancreatic insulin content in treated db/db mice are compared to that of the control group. Further, isolated islets from treated db/db are compared to those of the control group as described above. During the i.p. GTT, db/db mice treated with 11C7 anti-Nogo-A antibody presented higher plasma insulin levels at 15 (BrdU 1.25±0.08, 11C7 2.17±0.15, n=3-4, P<0.005) and 60 minutes (BrdU 1.57±0.04, 11C7 2.15±0.07, n=3-4, P<0.005), and 90 min, as compared with db/db mice treated with BrdU (FIG. 7A). Then, the glucose-induced insulin secretion was assessed in anesthesized db/db mice, i.v. injected with glucose (1 g/kg). Upon glucose injection, 11C7-treated db/db mice presented similar plasma insulin levels, compared with BrdU-treated db/db mice (FIG. 7B), similarly to the phenotype of Nogo-A KO, where the glucose-induced insulin secretion was not affected by the inactivation of Nogo-A (FIG. 4C). Also in accordance with the phenotype of Nogo-A KO mice, when the antibody-treated db/db mice were intravenously injected with glucose (1 g/kg) together with the cholinergic analogue carbachol (CC) (0.53 µM), 11C7-treated db/db mice showed an improved insulin secretion (4-fold on average) at 5 and 20 minutes (BrdU 10.65±2.14, 11C7 46.43±8.00, n=3, P<0.05) compared to BrdU-treated db/db mice (FIG. 7C).

In order to investigate the insulin secretion capacity of antibody-treated db/db mice, the pancreatic insulin content by immunoassay was assessed as described in Example 2. The inventors reasoned that the higher insulin secretion observed in db/db mice treated with Nogo-A neutralizing antibody could result from a higher parasympathetic input and/or from higher β-cell cholinergic sensitivity, such as in Nogo-A KO mice. Parasympathetic tone was therefore indirectly assessed by measuring the plasma level of pancreatic polypeptide (PP) after 2-Deoxy-D-glucose (2DG)-induced neuroglycopenia. After overnight fasting, before and after 2DG injection, PP levels were similar in both anti-Nogo-A treated and anti-BrdU treated control db/db mice (data not shown). Similarly, GIP levels were also measured in random-fed animals showing, as in Nogo_a KO mice, that before and after 2DG injection, GIP levels were similar in both anti-Nogo-A treated and anti-BrdU treated control db/db mice (FIG. 7D) (n=5, P=NS). Altogether, these results indicate that the antibody-mediated neutralization of Nogo-A does not affect the vagal and incretin input on β-cells. β-cell responsiveness to secretagogues was studied using isolated db/db islets cultured in the presence of glucose supplemented with CC (100 µM) or GLP-1 (100 nM). As observed with Nogo-A KO islets, islets from anti-Nogo-A treated db/db mice displayed higher insulin secretion in the presence of glucose supplemented with CC (n=7-15, P<0.005), yet their sensitivity to glucose supplemented with GLP-1 was not affected (FIG. 7E).

Altogether, these observations show that the intravenous administration of neutralizing Nogo-A antibody promotes the in vivo insulin secretion in 5-week-old diabetic db/db mice. Contrary to Nogo-A animals, the higher insulin secretion observed in 11C7-treated db/db mice probably resulted from a higher parasympathetic input only, as the parasympathetic input on islets was not altered. Therefore, those results support that reducing Nogo-A activity is of potential benefit for an anti-diabetic treatment, acting on the stimulatory input and the β-cells, by promoting insulin secretion in response to cholinergic stimuli, like after food intake, without hypoglycemic events.

db/db Homozygous Mice

Five weeks old male db/db homozygous mice, BKS.Cg-Dock7 m+/+Leprdb/J mice, are purchased from Charles River Laboratories, L'Arbresle, France for the treatment with a Nogo-A antagonist. All mice are maintained in a temperature-controlled room, on a 12-h light-dark cycle, and fed standard rodent chow ad libitum.

Statistical Analysis.

All results are reported as mean±standard error of the mean (SEM). Groups are compared with independent t tests (unpaired and two-tailed), reported as P values. All tests are performed using the GraphPad Prism software.

The invention claimed is:

1. A method of controlling blood glucose or blood insulin levels in a subject, said method comprising administering to a subject in need thereof an insulin secretory effective amount of a neutralising monoclonal anti-Nogo-A antibody, or a pharmaceutical formulation thereof.

2. The method according to claim 1, wherein the subject is suffering from insulin resistance.

3. The method according to claim 1, wherein the subject is suffering from diabetes mellitus.

4. The method according to claim 3, wherein diabetes mellitus is type II diabetes.

5. The method according claim 1, wherein the neutralising monoclonal anti-Nogo-A antibody is a neutralising monoclonal anti-Nogo-A antibody selected from humanised variants of mAbs 11C7, 2A10 or 2C4; and mAbs 6A3, H20L16, H27L16, H28L13 and H28L16.

6. The method according to claim 1, wherein the neutralising monoclonal anti-Nogo-A antibody is a humanised variant of mAb 11C7.

7. A method of repressing or treating insulin secretion deficiency in a subject, said method comprising administering in a subject in need thereof a therapeutically effective amount of a neutralising monoclonal anti-Nogo-A antibody, or a pharmaceutical formulation thereof.

8. The method according to claim 7, wherein the neutralising monoclonal anti-Nogo-A antibody is a neutralising anti-Nogo-A antibody selected from humanised variants of mAbs 11C7, 2A10 or 2C4; and mAbs 6A3, H20L16, H27L16, H28L13 and H28L16.

9. The method according to claim 7, wherein the neutralising monoclonal anti-Nogo-A antibody is a humanised variant of mAb 11C7 neutralising anti-Nogo-A antibody.

10. A pharmaceutical formulation comprising a neutralizing monoclonal anti-Nogo-A antibody, combined with at least one co-agent useful in the stimulation of insulin secretion or in the treatment of diabetes mellitus, and at least one pharmaceutically acceptable carrier.

11. The pharmaceutical formulation according to claim 10, wherein the neutralising monoclonal anti-Nogo-A antibody is a neutralising monoclonal anti-Nogo-A antibody selected from humanised variants of mAbs 11C7, 2A10 or 2C4; and mAbs 6A3, H20L16, H27L16, H28L13 and H28L16.

12. The pharmaceutical formulation according to claim 10, wherein the neutralising monoclonal anti-Nogo-A antibody is a humanised variant of mAb 11C7 neutralising monoclonal anti-Nogo-A antibody.

* * * * *

SEQUENCE LISTING

<160> NUMBER OF SEQ ID NOS: 43

<210> SEQ ID NO 1
<211> LENGTH: 1192
<212> TYPE: PRT
<213> ORGANISM: Homo sapiens

<400> SEQUENCE: 1

```
Met Glu Asp Leu Asp Gln Ser Pro Leu Val Ser Ser Asp Ser Pro
  1               5                  10                  15

Pro Arg Pro Gln Pro Ala Phe Lys Tyr Gln Phe Val Arg Glu Pro Glu
             20                  25                  30

Asp Glu Glu Glu Glu Glu Glu Glu Glu Asp Glu Asp Glu Asp
             35                  40                  45

Leu Glu Glu Leu Glu Val Leu Glu Arg Lys Pro Ala Ala Gly Leu Ser
     50                  55                      60

Ala Ala Pro Val Pro Thr Ala Pro Ala Gly Ala Pro Leu Met Asp
 65              70                  75                  80

Phe Gly Asn Asp Phe Val Pro Pro Ala Pro Arg Gly Pro Leu Pro Ala
             85                  90                  95

Ala Pro Pro Val Ala Pro Glu Arg Gln Pro Ser Trp Asp Pro Ser Pro
                 100                 105                 110

Val Ser Ser Thr Val Pro Ala Pro Ser Pro Leu Ser Ala Ala Ala Val
                 115                 120                 125

Ser Pro Ser Lys Leu Pro Glu Asp Asp Glu Pro Pro Ala Arg Pro Pro
 130                 135                 140

Pro Pro Pro Pro Ala Ser Val Ser Pro Gln Ala Glu Pro Val Trp Thr
 145                 150                 155                 160

Pro Pro Ala Pro Ala Pro Ala Ala Pro Pro Ser Thr Pro Ala Ala Pro
                 165                 170                 175

Lys Arg Arg Gly Ser Ser Gly Ser Val Asp Glu Thr Leu Phe Ala Leu
                 180                 185                 190

Pro Ala Ala Ser Glu Pro Val Ile Arg Ser Ser Ala Glu Asn Met Asp
                 195                 200                 205

Leu Lys Glu Gln Pro Gly Asn Thr Ile Ser Ala Gly Gln Glu Asp Phe
 210                 215                 220

Pro Ser Val Leu Leu Glu Thr Ala Ala Ser Leu Pro Ser Leu Ser Pro
 225                 230                 235                 240

Leu Ser Ala Ala Ser Phe Lys Glu His Glu Tyr Leu Gly Asn Leu Ser
                 245                 250                 255

Thr Val Leu Pro Thr Glu Gly Thr Leu Gln Glu Asn Val Ser Glu Ala
                 260                 265                 270

Ser Lys Glu Val Ser Glu Lys Ala Lys Thr Leu Leu Ile Asp Arg Asp
 275                 280                 285

Leu Thr Glu Phe Ser Glu Leu Glu Tyr Ser Glu Met Gly Ser Ser Phe
     290                 295                 300

Ser Val Ser Pro Lys Ala Glu Ser Ala Val Ile Val Ala Asn Pro Arg
 305                 310                 315                 320

Glu Glu Ile Ile Val Lys Asn Lys Asp Glu Glu Lys Leu Val Ser
                 325                 330                 335

Asn Asn Ile Leu His Asn Gln Gln Glu Leu Pro Thr Ala Leu Thr Lys
                 340                 345                 350

Leu Val Lys Glu Asp Glu Val Val Ser Ser Glu Lys Ala Lys Asp Ser
                 355                 360                 365

Phe Asn Glu Lys Arg Val Ala Val Glu Ala Pro Met Arg Glu Glu Tyr
                 370                 375                 380

Ala Asp Phe Lys Pro Phe Glu Arg Val Trp Glu Val Lys Asp Ser Lys
 385                 390                 395                 400

Glu Asp Ser Asp Met Leu Ala Ala Gly Gly Lys Ile Glu Ser Asn Leu
```

-continued

```
                405                 410                 415
Glu Ser Lys Val Asp Lys Lys Cys Phe Ala Asp Ser Leu Glu Gln Thr
            420                 425                 430
Asn His Glu Lys Asp Ser Glu Ser Ser Asn Asp Thr Ser Phe Pro
            435                 440                 445
Ser Thr Pro Glu Gly Ile Lys Asp Arg Ser Gly Ala Tyr Ile Thr Cys
450                 455                 460
Ala Pro Phe Asn Pro Ala Ala Thr Glu Ser Ile Ala Thr Asn Ile Phe
465                 470                 475                 480
Pro Leu Leu Gly Asp Pro Thr Ser Glu Asn Lys Thr Asp Glu Lys Lys
                485                 490                 495
Ile Glu Glu Lys Lys Ala Gln Ile Val Thr Glu Lys Asn Thr Ser Thr
            500                 505                 510
Lys Thr Ser Asn Pro Phe Leu Val Ala Ala Gln Asp Ser Glu Thr Asp
            515                 520                 525
Tyr Val Thr Thr Asp Asn Leu Thr Lys Val Thr Glu Glu Val Val Ala
        530                 535                 540
Asn Met Pro Glu Gly Leu Thr Pro Asp Leu Val Gln Glu Ala Cys Glu
545                 550                 555                 560
Ser Glu Leu Asn Glu Val Thr Gly Thr Lys Ile Ala Tyr Glu Thr Lys
                565                 570                 575
Met Asp Leu Val Gln Thr Ser Glu Val Met Gln Glu Ser Leu Tyr Pro
            580                 585                 590
Ala Ala Gln Leu Cys Pro Ser Phe Glu Glu Ser Glu Ala Thr Pro Ser
            595                 600                 605
Pro Val Leu Pro Asp Ile Val Met Glu Ala Pro Leu Asn Ser Ala Val
610                 615                 620
Pro Ser Ala Gly Ala Ser Val Ile Gln Pro Ser Ser Pro Leu Glu
625                 630                 635                 640
Ala Ser Ser Val Asn Tyr Glu Ser Ile Lys His Glu Pro Glu Asn Pro
                645                 650                 655
Pro Pro Tyr Glu Glu Ala Met Ser Val Ser Leu Lys Lys Val Ser Gly
            660                 665                 670
Ile Lys Glu Glu Ile Lys Glu Pro Glu Asn Ile Asn Ala Ala Leu Gln
            675                 680                 685
Glu Thr Glu Ala Pro Tyr Ile Ser Ile Ala Cys Asp Leu Ile Lys Glu
        690                 695                 700
Thr Lys Leu Ser Ala Glu Pro Ala Pro Asp Phe Ser Asp Tyr Ser Glu
705                 710                 715                 720
Met Ala Lys Val Glu Gln Pro Val Pro Asp His Ser Glu Leu Val Glu
                725                 730                 735
Asp Ser Ser Pro Asp Ser Glu Pro Val Asp Leu Phe Ser Asp Ser
            740                 745                 750
Ile Pro Asp Val Pro Gln Lys Gln Asp Glu Thr Val Met Leu Val Lys
            755                 760                 765
Glu Ser Leu Thr Glu Thr Ser Phe Glu Ser Met Ile Glu Tyr Glu Asn
        770                 775                 780
Lys Glu Lys Leu Ser Ala Leu Pro Pro Glu Gly Gly Lys Pro Tyr Leu
785                 790                 795                 800
Glu Ser Phe Lys Leu Ser Leu Asp Asn Thr Lys Asp Thr Leu Leu Pro
                805                 810                 815
Asp Glu Val Ser Thr Leu Ser Lys Lys Glu Lys Ile Pro Leu Gln Met
            820                 825                 830
```

Glu Glu Leu Ser Thr Ala Val Tyr Ser Asn Asp Asp Leu Phe Ile Ser
       835                 840                 845

Lys Glu Ala Gln Ile Arg Glu Thr Glu Thr Phe Ser Asp Ser Ser Pro
850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
            885                 890                 895

Lys Ser Glu Ile Ala Asn Ala Pro Asp Gly Ala Gly Ser Leu Pro Cys
        900                 905                 910

Thr Glu Leu Pro His Asp Leu Ser Leu Lys Asn Ile Gln Pro Lys Val
            915                 920                 925

Glu Glu Lys Ile Ser Phe Ser Asp Asp Phe Ser Lys Asn Gly Ser Ala
930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
            965                 970                 975

Ala Glu Lys Lys Leu Pro Ser Asp Thr Glu Lys Glu Asp Arg Ser Pro
        980                 985                 990

Ser Ala Ile Phe Ser Ala Glu Leu Ser Lys Thr Ser Val Val Asp Leu
            995                 1000                1005

Leu Tyr Trp Arg Asp Ile Lys Lys Thr Gly Val Val Phe Gly Ala
    1010                1015                1020

Ser Leu Phe Leu Leu Leu Ser Leu Thr Val Phe Ser Ile Val Ser
    1025                1030                1035

Val Thr Ala Tyr Ile Ala Leu Ala Leu Leu Ser Val Thr Ile Ser
    1040                1045                1050

Phe Arg Ile Tyr Lys Gly Val Ile Gln Ala Ile Gln Lys Ser Asp
    1055                1060                1065

Glu Gly His Pro Phe Arg Ala Tyr Leu Glu Ser Glu Val Ala Ile
    1070                1075                1080

Ser Glu Glu Leu Val Gln Lys Tyr Ser Asn Ser Ala Leu Gly His
    1085                1090                1095

Val Asn Cys Thr Ile Lys Glu Leu Arg Arg Leu Phe Leu Val Asp
    1100                1105                1110

Asp Leu Val Asp Ser Leu Lys Phe Ala Val Leu Met Trp Val Phe
    1115                1120                1125

Thr Tyr Val Gly Ala Leu Phe Asn Gly Leu Thr Leu Leu Ile Leu
    1130                1135                1140

Ala Leu Ile Ser Leu Phe Ser Val Pro Val Ile Tyr Glu Arg His
    1145                1150                1155

Gln Ala Gln Ile Asp His Tyr Leu Gly Leu Ala Asn Lys Asn Val
    1160                1165                1170

Lys Asp Ala Met Ala Lys Ile Gln Ala Lys Ile Pro Gly Leu Lys
    1175                1180                1185

Arg Lys Ala Glu
    1190

<210> SEQ ID NO 2
<211> LENGTH: 3579
<212> TYPE: DNA
<213> ORGANISM: Homo sapiens

<400> SEQUENCE: 2

```
atggaagacc tggaccagtc tcctctggtc tcgtcctcgg acagcccacc ccggccgcag    60
cccgcgttca gtaccagtt cgtgagggag cccgaggacg aggaggaaga agaggaggag   120
gaagaggagg acgaggacga agacctggag gagctggagg tgctggagag gaagcccgcc   180
gccgggctgt ccgcggcccc agtgcccacc gcccctgccg ccggcgcgcc cctgatggac   240
ttcggaaatg acttcgtgcc gccggcgccc cggggacccc tgccggccgc tcccccgtc    300
gccccggagc ggcagccgtc ttgggacccg agccggtgt cgtcgaccgt gcccgcgcca   360
tccccgctgt ctgctgccgc agtctcgccc tccaagctcc ctgaggacga cgagcctccg   420
gcccggcctc ccctcctcc cccggccagc gtgagccccc aggcagagcc cgtgtggacc   480
ccgccagccc cggctcccgc cgcgccccc tccaccccgg ccgcgcccaa gcgcaggggc   540
tcctcgggct cagtggatga gacccttttt gctcttcctg ctgcatctga gcctgtgata   600
cgctcctctg cagaaaatat ggacttgaag gagcagccag gtaacactat ttcggctggt   660
caagaggatt tcccatctgt cctgcttgaa actgctgctt ctcttccttc tctgtctcct   720
ctctcagccg cttcttttcaa agaacatgaa taccttggta atttgtcaac agtattaccc   780
actgaaggaa cacttcaaga aaatgtcagt gaagcttcta agaggtctc agagaaggca   840
aaaactctac tcatagatag agatttaaca gagttttcag aattagaata ctcagaaatg   900
ggatcatcgt tcagtgtctc tccaaaagca gaatctgccg taatagtagc aaatcctagg   960
gaagaaataa tcgtgaaaaa taaagatgaa gaagagaagt tagttagtaa taacatcctt  1020
cataatcaac aagagttacc tacagctctt actaaattgg ttaaagagga tgaagttgtg  1080
tcttcagaaa aagcaaaaga cagttttaat gaaagagag ttgcagtgga agctcctatg  1140
agggaggaat atgcagactt caaaccattt gagcgagtat gggaagtgaa agatagtaag  1200
gaagatagtg atatgttggc tgctggaggt aaaatcgaga gcaacttgga agtaaagtg   1260
gataaaaaat gttttgcaga tagccttgag caaactaatc acgaaaaaga tagtgagagt  1320
agtaatgatg atacttcttt ccccagtacg ccagaaggta taaaggatcg tccaggagca  1380
tatatcacat gtgctccctt taacccagca gcaactgaga gcattgcaac aaacattttt  1440
cctttgttag gagatcctac ttcagaaaat aagaccgatg aaaaaaaat agaagaaaag  1500
aaggcccaaa tagtaacaga gaagaatact agcaccaaaa catcaaaccc ttttcttgta  1560
gcagcacagg attctgagac agattatgtc acaacagata atttaacaaa ggtgactgag  1620
gaagtcgtgg caaacatgcc tgaaggcctg actccagatt tagtacagga agcatgtgaa  1680
agtgaattga atgaagttac tggtacaaag attgcttatg aaacaaaaat ggacttggtt  1740
caaacatcag aagttatgca agagtcactc tatcctgcag cacagctttg cccatcattt  1800
gaagagtcag aagctactcc ttcaccagtt ttgcctgaca ttgttatgga agcaccattg  1860
aattctgcag ttcctagtgc tggtgcttcc gtgatacagc ccagctcatc accattagaa  1920
gcttcttcag ttaattatga aagcataaaa catgagcctg aaaccccccc accatatgaa  1980
gaggccatga gtgtatcact aaaaaaagta tcaggaataa aggaagaaat taaagagcct  2040
gaaaatatta tgcagctct tcaagaaaca gaagctcctt atatatctat tgcatgtgat  2100
ttaattaaag aaacaaagct ttctgctgaa ccagctccgg atttctctga ttattcagaa  2160
atggcaaaag ttgaacagcc agtgcctgat cattctgagc tagttgaaga ttcctcacct  2220
gattctgaac cagttgactt atttagtgat gattcaatac ctgacgttcc acaaaaacaa  2280
gatgaaactg tgatgcttgt gaaagaaagt ctcactgaga cttcatttga gtcaatgata  2340
```

```
gaatatgaaa ataaggaaaa actcagtgct tgccacctg agggaggaaa gccatatttg    2400 gaatcttta agctcagttt agataacaca aaagataccc tgttacctga tgaagtttca    2460
acattgagca aaaggagaa aattcctttg cagatggagg agctcagtac tgcagtttat    2520
tcaaatgatg acttatttat ttctaaggaa gcacagataa gagaaactga aacgttttca    2580
gattcatctc caattgaaat tatagatgag ttccctacat tgatcagttc taaaactgat    2640
tcattttcta aattagccag ggaatatact gacctagaag tatcccacaa aagtgaaatt    2700
gctaatgccc cggatggagc tgggtcattg ccttgcacag aattgcccca tgacctttct    2760
ttgaagaaca tacaacccaa agttgaagag aaaatcagtt tctcagatga cttttctaaa    2820
aatgggtctg ctacatcaaa ggtgctctta ttgcctccag atgtttctgc tttggccact    2880
caagcagaga tagagagcat agttaaaccc aaagttcttg tgaaagaagc tgagaaaaaa    2940
cttccttccg atacagaaaa agaggacaga tcaccatctg ctatattttc agcagagctg    3000
agtaaaactt cagttgttga cctcctgtac tggagagaca ttaagaagac tggagtggtg    3060
tttggtgcca gcctattcct gctgctttca ttgacagtat tcagcattgt gagcgtaaca    3120
gcctacattg ccttggccct gctctctgtg accatcagct ttaggatata caagggtgtg    3180
atccaagcta tccagaaatc agatgaaggc cacccattca gggcatatct ggaatctgaa    3240
gttgctatat ctgaggagtt ggttcagaag tacagtaatt ctgctcttgg tcatgtgaac    3300
tgcacgataa aggaactcag gcgcctcttc ttagttgatg atttagttga ttctctgaag    3360
tttgcagtgt tgatgtgggt atttacctat gttggtgcct tgtttaatgg tctgacacta    3420
ctgattttgg ctctcatttc actcttcagt gttcctgtta tttatgaacg gcatcaggcg    3480
cagatagatc attatctagg acttgcaaat aagaatgtta agatgctat ggctaaaatc    3540 caagcaaaaa tccctggatt gaagcgcaaa gctgaatga                          3579
```

<210> SEQ ID NO 3
<211> LENGTH: 131
<212> TYPE: PRT
<213> ORGANISM: artificial sequence
<220> FEATURE:
<223> OTHER INFORMATION: Fragment 1-131 Human Nogo-A

<400> SEQUENCE: 3

```
Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro Glu
                20                  25                  30

Asp Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
        50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
        115                 120                 125

Ser Pro Ser
    130
```

```
<210> SEQ ID NO 4
<211> LENGTH: 808
<212> TYPE: PRT
<213> ORGANISM: artificial sequence
<220> FEATURE:
<223> OTHER INFORMATION: Fragment 132-939 Human Nogo-A

<400> SEQUENCE: 4

Lys Leu Pro Glu Asp Glu Pro Ala Arg Pro Pro Pro Pro
1               5                   10                  15

Pro Ala Ser Val Ser Pro Gln Ala Glu Pro Val Trp Thr Pro Pro Ala
            20                  25                  30

Pro Ala Pro Ala Ala Pro Pro Ser Thr Pro Ala Ala Pro Lys Arg Arg
        35                  40                  45

Gly Ser Ser Gly Ser Val Asp Glu Thr Leu Phe Ala Leu Pro Ala Ala
    50                  55                  60

Ser Glu Pro Val Ile Arg Ser Ser Ala Glu Asn Met Asp Leu Lys Glu
65                  70                  75                  80

Gln Pro Gly Asn Thr Ile Ser Ala Gly Gln Glu Asp Phe Pro Ser Val
                85                  90                  95

Leu Leu Glu Thr Ala Ala Ser Leu Pro Ser Leu Ser Pro Leu Ser Ala
            100                 105                 110

Ala Ser Phe Lys Glu His Glu Tyr Leu Gly Asn Leu Ser Thr Val Leu
        115                 120                 125

Pro Thr Glu Gly Thr Leu Gln Glu Asn Val Ser Glu Ala Ser Lys Glu
    130                 135                 140

Val Ser Glu Lys Ala Lys Thr Leu Leu Ile Asp Arg Asp Leu Thr Glu
145                 150                 155                 160

Phe Ser Glu Leu Glu Tyr Ser Glu Met Gly Ser Ser Phe Ser Val Ser
                165                 170                 175

Pro Lys Ala Glu Ser Ala Val Ile Val Ala Asn Pro Arg Glu Glu Ile
            180                 185                 190

Ile Val Lys Asn Lys Asp Glu Glu Lys Leu Val Ser Asn Asn Ile
        195                 200                 205

Leu His Asn Gln Gln Glu Leu Pro Thr Ala Leu Thr Lys Leu Val Lys
    210                 215                 220

Glu Asp Glu Val Val Ser Ser Glu Lys Ala Lys Asp Ser Phe Asn Glu
225                 230                 235                 240

Lys Arg Val Ala Val Glu Ala Pro Met Arg Glu Glu Tyr Ala Asp Phe
                245                 250                 255

Lys Pro Phe Glu Arg Val Trp Glu Val Lys Asp Ser Lys Glu Asp Ser
            260                 265                 270

Asp Met Leu Ala Ala Gly Gly Lys Ile Glu Ser Asn Leu Glu Ser Lys
        275                 280                 285

Val Asp Lys Lys Cys Phe Ala Asp Ser Leu Glu Gln Thr Asn His Glu
    290                 295                 300

Lys Asp Ser Glu Ser Ser Asn Asp Asp Thr Ser Phe Pro Ser Thr Pro
305                 310                 315                 320

Glu Gly Ile Lys Asp Arg Ser Gly Ala Tyr Ile Thr Cys Ala Pro Phe
                325                 330                 335

Asn Pro Ala Ala Thr Glu Ser Ile Ala Thr Asn Ile Phe Pro Leu Leu
            340                 345                 350

Gly Asp Pro Thr Ser Glu Asn Lys Thr Asp Glu Lys Lys Ile Glu Glu
        355                 360                 365
```

```
Lys Lys Ala Gln Ile Val Thr Glu Lys Asn Thr Ser Thr Lys Thr Ser
        370                 375                 380

Asn Pro Phe Leu Val Ala Ala Gln Asp Ser Glu Thr Asp Tyr Val Thr
385                 390                 395                 400

Thr Asp Asn Leu Thr Lys Val Thr Glu Val Val Ala Asn Met Pro
                405                 410                 415

Glu Gly Leu Thr Pro Asp Leu Val Gln Glu Ala Cys Glu Ser Glu Leu
                420                 425                 430

Asn Glu Val Thr Gly Thr Lys Ile Ala Tyr Glu Thr Lys Met Asp Leu
            435                 440                 445

Val Gln Thr Ser Glu Val Met Gln Glu Ser Leu Tyr Pro Ala Ala Gln
    450                 455                 460

Leu Cys Pro Ser Phe Glu Glu Ser Glu Ala Thr Pro Ser Pro Val Leu
465                 470                 475                 480

Pro Asp Ile Val Met Glu Ala Pro Leu Asn Ser Ala Val Pro Ser Ala
                485                 490                 495

Gly Ala Ser Val Ile Gln Pro Ser Ser Ser Pro Leu Glu Ala Ser Ser
                500                 505                 510

Val Asn Tyr Glu Ser Ile Lys His Glu Pro Glu Asn Pro Pro Tyr
    515                 520                 525

Glu Glu Ala Met Ser Val Ser Leu Lys Lys Val Ser Gly Ile Lys Glu
530                 535                 540

Glu Ile Lys Glu Pro Glu Asn Ile Asn Ala Ala Leu Gln Glu Thr Glu
545                 550                 555                 560

Ala Pro Tyr Ile Ser Ile Ala Cys Asp Leu Ile Lys Glu Thr Lys Leu
                565                 570                 575

Ser Ala Glu Pro Ala Pro Asp Phe Ser Asp Tyr Ser Glu Met Ala Lys
            580                 585                 590

Val Glu Gln Pro Val Pro Asp His Ser Glu Leu Val Glu Asp Ser Ser
        595                 600                 605

Pro Asp Ser Glu Pro Val Asp Leu Phe Ser Asp Ser Ile Pro Asp
    610                 615                 620

Val Pro Gln Lys Gln Asp Glu Thr Val Met Leu Val Lys Glu Ser Leu
625                 630                 635                 640

Thr Glu Thr Ser Phe Glu Ser Met Ile Glu Tyr Glu Asn Lys Glu Lys
                645                 650                 655

Leu Ser Ala Leu Pro Pro Glu Gly Gly Lys Pro Tyr Leu Glu Ser Phe
                660                 665                 670

Lys Leu Ser Leu Asp Asn Thr Lys Asp Thr Leu Leu Pro Asp Glu Val
            675                 680                 685

Ser Thr Leu Ser Lys Lys Glu Lys Ile Pro Leu Gln Met Glu Glu Leu
    690                 695                 700

Ser Thr Ala Val Tyr Ser Asn Asp Asp Leu Phe Ile Ser Lys Glu Ala
705                 710                 715                 720

Gln Ile Arg Glu Thr Glu Thr Phe Ser Asp Ser Pro Ile Glu Ile
                725                 730                 735

Ile Asp Glu Phe Pro Thr Leu Ile Ser Ser Lys Thr Asp Ser Phe Ser
                740                 745                 750

Lys Leu Ala Arg Glu Tyr Thr Asp Leu Glu Val Ser His Lys Ser Glu
            755                 760                 765

Ile Ala Asn Ala Pro Asp Gly Ala Gly Ser Leu Pro Cys Thr Glu Leu
    770                 775                 780
```

Pro His Asp Leu Ser Leu Lys Asn Ile Gln Pro Lys Val Glu Glu Lys
785                 790                 795                 800

Ile Ser Phe Ser Asp Asp Phe Ser
                805

<210> SEQ ID NO 5
<211> LENGTH: 296
<212> TYPE: PRT
<213> ORGANISM: artificial sequence
<220> FEATURE:
<223> OTHER INFORMATION: Fragment 206-501 Human Nogo-A

<400> SEQUENCE: 5

Asn Met Asp Leu Lys Glu Gln Pro Gly Asn Thr Ile Ser Ala Gly Gln
1               5                   10                  15

Glu Asp Phe Pro Ser Val Leu Leu Glu Thr Ala Ala Ser Leu Pro Ser
            20                  25                  30

Leu Ser Pro Leu Ser Ala Ala Ser Phe Lys Glu His Glu Tyr Leu Gly
            35                  40                  45

Asn Leu Ser Thr Val Leu Pro Thr Glu Gly Thr Leu Gln Glu Asn Val
    50                  55                  60

Ser Glu Ala Ser Lys Glu Val Ser Glu Lys Ala Lys Thr Leu Leu Ile
65                  70                  75                  80

Asp Arg Asp Leu Thr Glu Phe Ser Glu Leu Glu Tyr Ser Glu Met Gly
            85                  90                  95

Ser Ser Phe Ser Val Ser Pro Lys Ala Glu Ser Ala Val Ile Val Ala
            100                 105                 110

Asn Pro Arg Glu Glu Ile Ile Val Lys Asn Lys Asp Glu Glu Glu Lys
            115                 120                 125

Leu Val Ser Asn Asn Ile Leu His Asn Gln Gln Glu Leu Pro Thr Ala
130                 135                 140

Leu Thr Lys Leu Val Lys Glu Asp Glu Val Val Ser Ser Glu Lys Ala
145                 150                 155                 160

Lys Asp Ser Phe Asn Glu Lys Arg Val Ala Val Glu Ala Pro Met Arg
            165                 170                 175

Glu Glu Tyr Ala Asp Phe Lys Pro Phe Glu Arg Val Trp Glu Val Lys
            180                 185                 190

Asp Ser Lys Glu Asp Ser Asp Met Leu Ala Ala Gly Gly Lys Ile Glu
            195                 200                 205

Ser Asn Leu Glu Ser Lys Val Asp Lys Lys Cys Phe Ala Asp Ser Leu
    210                 215                 220

Glu Gln Thr Asn His Glu Lys Asp Ser Glu Ser Ser Asn Asp Asp Thr
225                 230                 235                 240

Ser Phe Pro Ser Thr Pro Glu Gly Ile Lys Asp Arg Ser Gly Ala Tyr
            245                 250                 255

Ile Thr Cys Ala Pro Phe Asn Pro Ala Ala Thr Glu Ser Ile Ala Thr
            260                 265                 270

Asn Ile Phe Pro Leu Leu Gly Asp Pro Thr Ser Glu Asn Lys Thr Asp
            275                 280                 285

Glu Lys Lys Ile Glu Glu Lys Lys
    290                 295

<210> SEQ ID NO 6
<211> LENGTH: 180
<212> TYPE: PRT
<213> ORGANISM: artificial sequence
<220> FEATURE:

-continued

<223> OTHER INFORMATION: Fragment 501-680 Human Nogo-A

<400> SEQUENCE: 6

```
Lys Ala Gln Ile Val Thr Glu Lys Asn Thr Ser Lys Thr Ser Asn
1               5                   10                  15
Pro Phe Leu Val Ala Ala Gln Asp Ser Glu Thr Asp Tyr Val Thr Thr
                20                  25                  30
Asp Asn Leu Thr Lys Val Thr Glu Glu Val Val Ala Asn Met Pro Glu
            35                  40                  45
Gly Leu Thr Pro Asp Leu Val Gln Glu Ala Cys Glu Ser Glu Leu Asn
        50                  55                  60
Glu Val Thr Gly Thr Lys Ile Ala Tyr Glu Thr Lys Met Asp Leu Val
65                  70                  75                  80
Gln Thr Ser Glu Val Met Gln Glu Ser Leu Tyr Pro Ala Ala Gln Leu
                85                  90                  95
Cys Pro Ser Phe Glu Glu Ser Glu Ala Thr Pro Ser Pro Val Leu Pro
                100                 105                 110
Asp Ile Val Met Glu Ala Pro Leu Asn Ser Ala Val Pro Ser Ala Gly
            115                 120                 125
Ala Ser Val Ile Gln Pro Ser Ser Ser Pro Leu Glu Ala Ser Ser Val
        130                 135                 140
Asn Tyr Glu Ser Ile Lys His Glu Pro Glu Asn Pro Pro Pro Tyr Glu
145                 150                 155                 160
Glu Ala Met Ser Val Ser Leu Lys Lys Val Ser Gly Ile Lys Glu Glu
                165                 170                 175
Ile Lys Glu Pro
            180
```

<210> SEQ ID NO 7
<211> LENGTH: 75
<212> TYPE: PRT
<213> ORGANISM: artificial sequence
<220> FEATURE:
<223> OTHER INFORMATION: Fragment 132-206 Human Nogo-A

<400> SEQUENCE: 7

```
Lys Leu Pro Glu Asp Asp Glu Pro Pro Ala Arg Pro Pro Pro Pro Pro
1               5                   10                  15
Pro Ala Ser Val Ser Pro Gln Ala Glu Pro Val Trp Thr Pro Pro Ala
                20                  25                  30
Pro Ala Pro Ala Ala Pro Pro Ser Thr Pro Ala Ala Pro Lys Arg Arg
            35                  40                  45
Gly Ser Ser Gly Ser Val Asp Glu Thr Leu Phe Ala Leu Pro Ala Ala
        50                  55                  60
Ser Glu Pro Val Ile Arg Ser Ser Ala Glu Asn
65                  70                  75
```

<210> SEQ ID NO 8
<211> LENGTH: 1163
<212> TYPE: PRT
<213> ORGANISM: Rattus norvegicus

<400> SEQUENCE: 8

```
Met Glu Asp Ile Asp Gln Ser Ser Leu Val Ser Ser Ser Thr Asp Ser
1               5                   10                  15
Pro Pro Arg Pro Pro Pro Ala Phe Lys Tyr Gln Phe Val Thr Glu Pro
                20                  25                  30
```

-continued

```
Glu Asp Glu Glu Asp Glu Glu Glu Glu Asp Glu Glu Asp Asp
         35                  40                  45
Glu Asp Leu Glu Glu Leu Glu Val Leu Glu Arg Lys Pro Ala Ala Gly
 50                  55                  60
Leu Ser Ala Ala Ala Val Pro Pro Ala Ala Ala Pro Leu Leu Asp
 65                  70                  75                  80
Phe Ser Ser Asp Ser Val Pro Pro Ala Pro Arg Gly Pro Leu Pro Ala
                 85                  90                  95
Ala Pro Pro Ala Ala Pro Glu Arg Gln Pro Ser Trp Glu Arg Ser Pro
             100                 105                 110
Ala Ala Pro Ala Pro Ser Leu Pro Pro Ala Ala Val Leu Pro Ser
             115                 120                 125
Lys Leu Pro Glu Asp Asp Glu Pro Pro Ala Arg Pro Pro Pro Pro
 130                 135                 140
Pro Ala Gly Ala Ser Pro Leu Ala Glu Pro Ala Ala Pro Ser Thr
 145                 150                 155                 160
Pro Ala Ala Pro Lys Arg Arg Gly Ser Gly Ser Val Asp Glu Thr Leu
                 165                 170                 175
Phe Ala Leu Pro Ala Ala Ser Glu Pro Val Ile Pro Ser Ser Ala Glu
             180                 185                 190
Lys Ile Met Asp Leu Met Glu Gln Pro Gly Asn Thr Val Ser Ser Gly
             195                 200                 205
Gln Glu Asp Phe Pro Ser Val Leu Leu Glu Thr Ala Ala Ser Leu Pro
     210                 215                 220
Ser Leu Ser Pro Leu Ser Thr Val Ser Phe Lys Glu His Gly Tyr Leu
225                 230                 235                 240
Gly Asn Leu Ser Ala Val Ser Ser Ser Glu Gly Thr Ile Glu Glu Thr
                 245                 250                 255
Leu Asn Glu Ala Ser Lys Glu Leu Pro Glu Arg Ala Thr Asn Pro Phe
             260                 265                 270
Val Asn Arg Asp Leu Ala Glu Phe Ser Glu Leu Glu Tyr Ser Glu Met
             275                 280                 285
Gly Ser Ser Phe Lys Gly Ser Pro Lys Gly Glu Ser Ala Ile Leu Val
 290                 295                 300
Glu Asn Thr Lys Glu Glu Val Ile Val Arg Ser Lys Asp Lys Glu Asp
305                 310                 315                 320
Leu Val Cys Ser Ala Ala Leu His Ser Pro Gln Glu Ser Pro Val Gly
                 325                 330                 335
Lys Glu Asp Arg Val Val Ser Pro Glu Lys Thr Met Asp Ile Phe Asn
             340                 345                 350
Glu Met Gln Met Ser Val Val Ala Pro Val Arg Glu Glu Tyr Ala Asp
             355                 360                 365
Phe Lys Pro Phe Glu Gln Ala Trp Glu Val Lys Asp Thr Tyr Glu Gly
             370                 375                 380
Ser Arg Asp Val Leu Ala Ala Arg Ala Asn Val Glu Ser Lys Val Asp
385                 390                 395                 400
Arg Lys Cys Leu Glu Asp Ser Leu Glu Gln Lys Ser Leu Gly Lys Asp
                 405                 410                 415
Ser Glu Gly Arg Asn Glu Asp Ala Ser Phe Pro Ser Thr Pro Glu Pro
             420                 425                 430
Val Lys Asp Ser Ser Arg Ala Tyr Ile Thr Cys Ala Ser Phe Thr Ser
             435                 440                 445
Ala Thr Glu Ser Thr Thr Ala Asn Thr Phe Pro Leu Leu Glu Asp His
```

-continued

```
            450                 455                 460
Thr Ser Glu Asn Lys Thr Asp Glu Lys Ile Glu Arg Lys Ala
465                 470                 475                 480

Gln Ile Ile Thr Glu Lys Thr Ser Pro Lys Thr Ser Asn Pro Phe Leu
                485                 490                 495

Val Ala Val Gln Asp Ser Glu Ala Asp Tyr Val Thr Asp Thr Leu
                500                 505                 510

Ser Lys Val Thr Glu Ala Ala Val Ser Asn Met Pro Glu Gly Leu Thr
                515                 520                 525

Pro Asp Leu Val Gln Glu Ala Cys Glu Ser Glu Leu Asn Glu Ala Thr
530                 535                 540

Gly Thr Lys Ile Ala Tyr Glu Thr Lys Val Asp Leu Val Gln Thr Ser
545                 550                 555                 560

Glu Ala Ile Gln Glu Ser Leu Tyr Pro Thr Ala Gln Leu Cys Pro Ser
                565                 570                 575

Phe Glu Glu Ala Glu Ala Thr Pro Ser Pro Val Leu Pro Asp Ile Val
                580                 585                 590

Met Glu Ala Pro Leu Asn Ser Leu Pro Ser Ala Gly Ala Ser Val
                595                 600                 605

Val Gln Pro Ser Val Ser Pro Leu Glu Ala Pro Pro Val Ser Tyr
                610                 615                 620

Asp Ser Ile Lys Leu Glu Pro Glu Asn Pro Pro Tyr Glu Ala
625                 630                 635                 640

Met Asn Val Ala Leu Lys Ala Leu Gly Thr Lys Glu Gly Ile Lys Glu
                645                 650                 655

Pro Glu Ser Phe Asn Ala Ala Val Gln Glu Thr Glu Ala Pro Tyr Ile
                660                 665                 670

Ser Ile Ala Cys Asp Leu Ile Lys Glu Thr Lys Leu Ser Thr Glu Pro
                675                 680                 685

Ser Pro Asp Phe Ser Asn Tyr Ser Glu Ile Ala Lys Phe Glu Lys Ser
                690                 695                 700

Val Pro Glu His Ala Glu Leu Val Glu Asp Ser Ser Pro Glu Ser Glu
705                 710                 715                 720

Pro Val Asp Leu Phe Ser Asp Ser Ile Pro Glu Val Pro Gln Thr
                725                 730                 735

Gln Glu Glu Ala Val Met Leu Met Lys Glu Ser Leu Thr Glu Val Ser
                740                 745                 750

Glu Thr Val Ala Gln His Lys Glu Glu Arg Leu Ser Ala Ser Pro Gln
                755                 760                 765

Glu Leu Gly Lys Pro Tyr Leu Glu Ser Phe Gln Pro Asn Leu His Ser
                770                 775                 780

Thr Lys Asp Ala Ala Ser Asn Asp Ile Pro Thr Leu Thr Lys Lys Glu
785                 790                 795                 800

Lys Ile Ser Leu Gln Met Glu Glu Phe Asn Thr Ala Ile Tyr Ser Asn
                805                 810                 815

Asp Asp Leu Leu Ser Ser Lys Glu Asp Lys Ile Lys Glu Ser Glu Thr
                820                 825                 830

Phe Ser Asp Ser Ser Pro Ile Glu Ile Asp Glu Phe Pro Thr Phe
                835                 840                 845

Val Ser Ala Lys Asp Asp Ser Pro Lys Leu Ala Lys Glu Tyr Thr Asp
                850                 855                 860

Leu Glu Val Ser Asp Lys Ser Glu Ile Ala Asn Ile Gln Ser Gly Ala
865                 870                 875                 880
```

-continued

Asp Ser Leu Pro Cys Leu Glu Leu Pro Cys Asp Leu Ser Phe Lys Asn
            885                 890                 895

Ile Tyr Pro Lys Asp Glu Val His Val Ser Asp Glu Phe Ser Glu Asn
            900                 905                 910

Arg Ser Val Ser Lys Ala Ser Ile Ser Pro Ser Asn Val Ser Ala
            915                 920             925

Leu Glu Pro Gln Thr Glu Met Gly Ser Ile Val Lys Ser Lys Ser Leu
 930                 935                 940

Thr Lys Glu Ala Glu Lys Lys Leu Pro Ser Asp Thr Glu Lys Glu Asp
945                 950                 955                 960

Arg Ser Leu Ser Ala Val Leu Ser Ala Glu Leu Ser Lys Thr Ser Val
            965                 970                 975

Val Asp Leu Leu Tyr Trp Arg Asp Ile Lys Lys Thr Gly Val Val Phe
            980                 985                 990

Gly Ala Ser Leu Phe Leu Leu Leu Ser Leu Thr Val Phe Ser Ile Val
            995                1000                1005

Ser Val Thr Ala Tyr Ile Ala Leu Ala Leu Leu Ser Val Thr Ile
           1010                1015                1020

Ser Phe Arg Ile Tyr Lys Gly Val Ile Gln Ala Ile Gln Lys Ser
           1025                1030                1035

Asp Glu Gly His Pro Phe Arg Ala Tyr Leu Glu Ser Glu Val Ala
           1040                1045                1050

Ile Ser Glu Glu Leu Val Gln Lys Tyr Ser Asn Ser Ala Leu Gly
           1055                1060                1065

His Val Asn Ser Thr Ile Lys Glu Leu Arg Arg Leu Phe Leu Val
           1070                1075                1080

Asp Asp Leu Val Asp Ser Leu Lys Phe Ala Val Leu Met Trp Val
           1085                1090                1095

Phe Thr Tyr Val Gly Ala Leu Phe Asn Gly Leu Thr Leu Leu Ile
           1100                1105                1110

Leu Ala Leu Ile Ser Leu Phe Ser Ile Pro Val Ile Tyr Glu Arg
           1115                1120                1125

His Gln Val Gln Ile Asp His Tyr Leu Gly Leu Ala Asn Lys Ser
           1130                1135                1140

Val Lys Asp Ala Met Ala Lys Ile Gln Ala Lys Ile Pro Gly Leu
           1145                1150                1155

Lys Arg Lys Ala Asp
           1160

<210> SEQ ID NO 9
<211> LENGTH: 647
<212> TYPE: PRT
<213> ORGANISM: Bos taurus

<400> SEQUENCE: 9

Met Pro Glu Gly Leu Thr Pro Asp Leu Val Gln Glu Ala Cys Glu Ser
 1               5                  10                  15

Glu Leu Asn Glu Ala Thr Gly Thr Lys Ile Ala Phe Glu Thr Lys Met
                20                  25                  30

Asp Leu Val Gln Thr Ser Glu Ala Val Gln Glu Ser Leu Tyr Pro Val
            35                  40                  45

Thr Gln Leu Cys Pro Ser Phe Glu Glu Ser Glu Ala Thr Pro Ser Pro
        50                  55                  60

Val Leu Pro Asp Ile Val Met Glu Ala Pro Leu Asn Ser Val Val Pro

```
                65                  70                  75                  80
        Ser Ala Gly Ala Ser Ala Val Gln Leu Ser Ser Pro Leu Glu Thr
                        85                  90                  95

Pro Pro Ser Val Asn Tyr Glu Ser Ile Lys Phe Glu Pro Glu Asn Pro
                        100                 105                 110

Pro Pro Tyr Glu Glu Ala Met Asn Val Ser Leu Lys Lys Glu Ser Gly
                        115                 120                 125

Met Asn Glu Glu Ile Thr Glu Pro Gly Ile Ser Val Ala Val Gln
                130                 135                 140

Glu Thr Glu Ala Pro Tyr Ile Ser Ile Ala Cys Asp Leu Ile Lys Glu
        145                 150                 155                 160

Thr Lys Ile Ser Thr Glu Pro Thr Pro Asp Phe Ser Ser Tyr Ser Glu
                        165                 170                 175

Ile Ala Glu Val Ala Gln Pro Val Pro Glu His Ser Glu Leu Val Glu
                        180                 185                 190

Asp Ser Ser Pro Asp Ser Glu Pro Val Asp Leu Phe Ser Asp Asp Ser
                        195                 200                 205

Ile Pro Glu Val Pro Gln Lys Gln Asp Glu Ala Val Ile Leu Val Lys
                210                 215                 220

Glu Asn Leu Thr Glu Ile Ser Ser Glu Ser Met Thr Gly His Asp Asn
        225                 230                 235                 240

Lys Gly Lys Leu Ser Ala Ser Pro Ser Pro Glu Gly Gly Lys Pro Tyr
                        245                 250                 255

Leu Glu Ser Phe Gln Pro Ser Leu Gly Ile Thr Lys Asp Thr Leu Ala
                        260                 265                 270

Pro Asp Glu Val Ser Ala Leu Thr Gln Lys Glu Lys Ile Pro Leu Gln
                        275                 280                 285

Met Glu Glu Leu Asn Thr Ala Val Tyr Ser Ser Asp Gly Leu Phe Ile
                290                 295                 300

Ala Gln Glu Ala Asn Leu Arg Glu Ser Glu Thr Phe Ser Asp Ser Ser
        305                 310                 315                 320

Pro Ile Glu Ile Ile Asp Glu Phe Pro Thr Phe Val Ser Ser Lys Ala
                        325                 330                 335

Asp Ser Ser Pro Thr Leu Ala Arg Glu Tyr Thr Asp Leu Glu Val Ala
                        340                 345                 350

His Lys Ser Glu Ile Ala Asp Ile Gln Asp Gly Ala Gly Ser Leu Ala
                        355                 360                 365

Cys Ala Gly Leu Pro His Asp Leu Ser Phe Lys Ser Ile Gln Pro Lys
                370                 375                 380

Glu Glu Val His Val Pro Asp Glu Phe Ser Lys Asp Arg Gly Asp Val
        385                 390                 395                 400

Ser Lys Val Pro Ile Leu Pro Pro Asp Val Ser Ala Leu Asp Ala Gln
                        405                 410                 415

Ala Glu Ile Gly Ser Ile Glu Lys Pro Lys Val Leu Lys Glu Ala
                        420                 425                 430

Glu Arg Lys Leu Pro Ser Asp Thr Glu Lys Glu Arg Arg Ser Pro Ser
                        435                 440                 445

Ala Ile Phe Ser Ala Glu Leu Ser Lys Thr Ser Val Val Asp Leu Leu
                        450                 455                 460

Tyr Trp Arg Asp Ile Lys Lys Thr Gly Val Val Phe Gly Ala Ser Leu
        465                 470                 475                 480

Phe Leu Leu Leu Ser Leu Thr Val Phe Ser Ile Val Ser Val Thr Ala
                        485                 490                 495
```

```
Tyr Ile Ala Leu Ala Leu Leu Ser Val Thr Ile Ser Phe Arg Ile Tyr
            500                 505                 510

Lys Gly Val Ile Gln Ala Ile Gln Lys Ser Asp Glu Gly His Pro Phe
            515                 520                 525

Arg Ala Tyr Leu Glu Ser Glu Val Ala Ile Ser Glu Glu Leu Val Gln
            530                 535                 540

Lys Tyr Ser Asn Ser Ala Leu Gly His Val Asn Cys Thr Ile Lys Glu
545                 550                 555                 560

Leu Arg Arg Leu Phe Leu Val Asp Asp Leu Val Asp Ser Leu Lys Phe
                565                 570                 575

Ala Val Leu Met Trp Val Phe Thr Tyr Val Gly Ala Leu Phe Asn Gly
            580                 585                 590

Leu Thr Leu Leu Ile Leu Ala Leu Ile Ser Leu Phe Ser Val Pro Val
            595                 600                 605

Ile Tyr Glu Arg His Gln Ala Gln Ile Asp His Tyr Leu Gly Leu Ala
            610                 615                 620

Asn Lys Asn Val Lys Asp Ala Met Ala Lys Ile Gln Ala Lys Ile Pro
625                 630                 635                 640

Gly Leu Lys Arg Lys Ala Glu
            645

<210> SEQ ID NO 10
<211> LENGTH: 1162
<212> TYPE: PRT
<213> ORGANISM: Mus musculus

<400> SEQUENCE: 10

Met Glu Asp Ile Asp Gln Ser Ser Leu Val Ser Ser Ser Ala Asp Ser
1               5                   10                  15

Pro Pro Arg Pro Pro Ala Phe Lys Tyr Gln Phe Val Thr Glu Pro
            20                  25                  30

Glu Asp Glu Glu Asp Glu Asp Glu Glu Glu Glu Asp Asp Glu
            35                  40                  45

Asp Leu Glu Glu Leu Glu Val Leu Glu Arg Lys Pro Ala Ala Gly Leu
    50                  55                  60

Ser Ala Ala Pro Val Pro Pro Ala Ala Pro Leu Leu Asp Phe Ser
65                  70                  75                  80

Ser Asp Ser Val Pro Pro Ala Pro Arg Gly Pro Leu Pro Ala Ala Pro
                85                  90                  95

Pro Thr Ala Pro Glu Arg Gln Pro Ser Trp Glu Arg Ser Pro Ala Ala
            100                 105                 110

Ser Ala Pro Ser Leu Pro Pro Ala Ala Val Leu Pro Ser Lys Leu
            115                 120                 125

Pro Glu Asp Asp Glu Pro Pro Ala Arg Pro Pro Ala Pro Ala Gly Ala
            130                 135                 140

Ser Pro Leu Ala Glu Pro Ala Pro Pro Ser Thr Pro Ala Ala Pro
145                 150                 155                 160

Lys Arg Arg Gly Ser Gly Ser Val Asp Glu Thr Leu Phe Ala Leu Pro
                165                 170                 175

Ala Ala Ser Glu Pro Val Ile Pro Ser Ser Ala Glu Lys Ile Met Asp
            180                 185                 190

Leu Lys Glu Gln Pro Gly Asn Thr Val Ser Ser Gly Gln Glu Asp Phe
            195                 200                 205

Pro Ser Val Leu Phe Glu Thr Ala Ala Ser Leu Pro Ser Leu Ser Pro
```

```
            210                 215                 220
Leu Ser Thr Val Ser Phe Lys Glu His Gly Tyr Leu Gly Asn Leu Ser
225                 230                 235                 240

Ala Val Ala Ser Thr Glu Gly Thr Ile Glu Thr Leu Asn Glu Ala
                245                 250                 255

Ser Arg Glu Leu Pro Glu Arg Ala Thr Asn Pro Phe Val Asn Arg Glu
                260                 265                 270

Ser Ala Glu Phe Ser Val Leu Glu Tyr Ser Glu Met Gly Ser Ser Phe
            275                 280                 285

Asn Gly Ser Pro Lys Gly Glu Ser Ala Met Leu Val Glu Asn Thr Lys
            290                 295                 300

Glu Glu Val Ile Val Arg Ser Lys Asp Lys Glu Asp Leu Val Cys Ser
305                 310                 315                 320

Ala Ala Leu His Asn Pro Gln Glu Ser Pro Ala Thr Leu Thr Lys Val
                325                 330                 335

Val Lys Glu Asp Gly Val Met Ser Pro Glu Lys Thr Met Asp Ile Phe
                340                 345                 350

Asn Glu Met Lys Met Ser Val Val Ala Pro Val Arg Glu Glu Tyr Ala
                355                 360                 365

Asp Phe Lys Pro Phe Glu Gln Ala Trp Glu Val Lys Asp Thr Tyr Glu
            370                 375                 380

Gly Ser Arg Asp Val Leu Ala Ala Arg Ala Asn Met Glu Ser Lys Val
385                 390                 395                 400

Asp Lys Lys Cys Phe Glu Asp Ser Leu Glu Gln Lys Gly His Gly Lys
                405                 410                 415

Asp Ser Glu Ser Arg Asn Glu Asn Ala Ser Phe Pro Arg Thr Pro Glu
                420                 425                 430

Leu Val Lys Asp Gly Ser Arg Ala Tyr Ile Thr Cys Asp Ser Phe Ser
                435                 440                 445

Ser Ala Thr Glu Ser Thr Ala Ala Asn Ile Phe Pro Val Leu Glu Asp
            450                 455                 460

His Thr Ser Glu Asn Lys Thr Asp Glu Lys Lys Ile Glu Glu Arg Lys
465                 470                 475                 480

Ala Gln Ile Ile Thr Glu Lys Thr Ser Pro Lys Thr Ser Asn Pro Phe
                485                 490                 495

Leu Val Ala Ile His Asp Ser Glu Ala Asp Tyr Val Thr Thr Asp Asn
                500                 505                 510

Leu Ser Lys Val Thr Glu Ala Val Ala Thr Met Pro Glu Gly Leu
            515                 520                 525

Thr Pro Asp Leu Val Gln Glu Ala Cys Glu Ser Glu Leu Asn Glu Ala
530                 535                 540

Thr Gly Thr Lys Ile Ala Tyr Glu Thr Lys Val Asp Leu Val Gln Thr
545                 550                 555                 560

Ser Glu Ala Ile Gln Glu Ser Ile Tyr Pro Thr Ala Gln Leu Cys Pro
                565                 570                 575

Ser Phe Glu Glu Ala Glu Ala Thr Pro Ser Pro Val Leu Pro Asp Ile
            580                 585                 590

Val Met Glu Ala Pro Leu Asn Ser Leu Leu Pro Ser Thr Gly Ala Ser
            595                 600                 605

Val Ala Gln Pro Ser Ala Ser Pro Leu Glu Val Pro Ser Pro Val Ser
            610                 615                 620

Tyr Asp Gly Ile Lys Leu Glu Pro Glu Asn Pro Pro Tyr Glu Glu
625                 630                 635                 640
```

-continued

```
Ala Met Ser Val Ala Leu Lys Thr Ser Asp Ser Lys Glu Ile Lys
            645                 650                 655
Glu Pro Glu Ser Phe Asn Ala Ala Gln Glu Ala Glu Ala Pro Tyr
            660                 665                 670
Ile Ser Ile Ala Cys Asp Leu Ile Lys Glu Thr Lys Leu Ser Thr Glu
            675                 680                 685
Pro Ser Pro Glu Phe Ser Asn Tyr Ser Glu Ile Ala Lys Phe Glu Lys
690                     695                 700
Ser Val Pro Asp His Cys Glu Leu Val Asp Ser Ser Pro Glu Ser
705                 710                 715                 720
Glu Pro Val Asp Leu Phe Ser Asp Ser Ile Pro Glu Val Pro Gln
            725                 730                 735
Thr Gln Glu Glu Ala Val Met Leu Met Lys Glu Ser Leu Thr Glu Val
            740                 745                 750
Ser Glu Thr Val Thr Gln His Lys His Lys Glu Arg Leu Ser Ala Ser
            755                 760                 765
Pro Gln Glu Val Gly Lys Pro Tyr Leu Glu Ser Phe Gln Pro Asn Leu
            770                 775                 780
His Ile Thr Lys Asp Ala Ala Ser Asn Glu Ile Pro Thr Leu Thr Lys
785                 790                 795                 800
Lys Glu Thr Ile Ser Leu Gln Met Glu Glu Phe Asn Thr Ala Ile Tyr
                    805                 810                 815
Ser Asn Asp Asp Leu Leu Ser Ser Lys Glu Asp Lys Met Lys Glu Ser
                    820                 825                 830
Glu Thr Phe Ser Asp Ser Ser Pro Ile Glu Ile Ile Asp Glu Phe Pro
            835                 840                 845
Thr Phe Val Ser Ala Lys Asp Asp Ser Pro Lys Glu Tyr Thr Asp Leu
            850                 855                 860
Glu Val Ser Asn Lys Ser Glu Ile Ala Asn Val Gln Ser Gly Ala Asn
865                 870                 875                 880
Ser Leu Pro Cys Ser Glu Leu Pro Cys Asp Leu Ser Phe Lys Asn Thr
                    885                 890                 895
Tyr Pro Lys Asp Glu Ala His Val Ser Asp Glu Phe Ser Lys Ser Arg
            900                 905                 910
Ser Ser Val Ser Lys Val Pro Leu Leu Leu Pro Asn Val Ser Ala Leu
            915                 920                 925
Glu Ser Gln Ile Glu Met Gly Asn Ile Val Lys Pro Lys Val Leu Thr
930                 935                 940
Lys Glu Ala Glu Glu Lys Leu Pro Ser Asp Thr Glu Lys Glu Asp Arg
945                 950                 955                 960
Ser Leu Thr Ala Val Leu Ser Ala Glu Leu Asn Lys Thr Ser Val Val
                    965                 970                 975
Asp Leu Leu Tyr Trp Arg Asp Ile Lys Lys Thr Gly Val Val Phe Gly
                    980                 985                 990
Ala Ser Leu Phe Leu Leu Leu Ser  Leu Thr Val Phe Ser  Ile Val Ser
            995                 1000                1005
Val Thr  Ala Tyr Ile Ala Leu  Ala Leu Leu Ser Val  Thr Ile Ser
    1010                1015                1020
Phe Arg  Ile Tyr Lys Gly Val  Ile Gln Ala Ile Gln  Lys Ser Asp
    1025                1030                1035
Glu Gly  His Pro Phe Arg Ala  Tyr Leu Glu Ser Glu  Val Ala Ile
    1040                1045                1050
```

Ser Glu Glu Leu Val Gln Lys Tyr Ser Asn Ser Ala Leu Gly His
    1055                1060                1065

Val Asn Ser Thr Ile Lys Glu Leu Arg Arg Leu Phe Leu Val Asp
    1070                1075                1080

Asp Leu Val Asp Ser Leu Lys Phe Ala Val Leu Met Trp Val Phe
    1085                1090                1095

Thr Tyr Val Gly Ala Leu Phe Asn Gly Leu Thr Leu Leu Ile Leu
    1100                1105                1110

Ala Leu Ile Ser Leu Phe Ser Ile Pro Val Ile Tyr Glu Arg His
    1115                1120                1125

Gln Ala Gln Ile Asp His Tyr Leu Gly Leu Ala Asn Lys Ser Val
    1130                1135                1140

Lys Asp Ala Met Ala Lys Ile Gln Ala Lys Ile Pro Gly Leu Lys
    1145                1150                1155

Arg Lys Ala Glu
    1160

<210> SEQ ID NO 11
<211> LENGTH: 25
<212> TYPE: DNA
<213> ORGANISM: artificial sequence
<220> FEATURE:
<223> OTHER INFORMATION: 5'-Nogo-A-WT/KO locus primer

<400> SEQUENCE: 11
tgctttgaat tattccaagt agtcc                                         25

<210> SEQ ID NO 12
<211> LENGTH: 19
<212> TYPE: DNA
<213> ORGANISM: artificial sequence
<220> FEATURE:
<223> OTHER INFORMATION: 3'-Nogo-A-WT locus primer

<400> SEQUENCE: 12
agtgagtacc cagctgcac                                                19

<210> SEQ ID NO 13
<211> LENGTH: 25
<212> TYPE: DNA
<213> ORGANISM: artificial sequence
<220> FEATURE:
<223> OTHER INFORMATION: 3'-Nogo-A-KO locus primer

<400> SEQUENCE: 13
cctacccggt agaatatcga taagc                                         25

<210> SEQ ID NO 14
<211> LENGTH: 25
<212> TYPE: DNA
<213> ORGANISM: artificial sequence
<220> FEATURE:
<223> OTHER INFORMATION: Nogo-A Fwd primer

<400> SEQUENCE: 14
cctctctggc aattctctct agaag                                         25

<210> SEQ ID NO 15
<211> LENGTH: 19
<212> TYPE: DNA
<213> ORGANISM: artificial sequence
<220> FEATURE:
<223> OTHER INFORMATION: Nogo-A Rev primer

```
<400> SEQUENCE: 15
aggggctcgg gctcagtgg                                                    19

<210> SEQ ID NO 16
<211> LENGTH: 24
<212> TYPE: DNA
<213> ORGANISM: artificial sequence
<220> FEATURE:
<223> OTHER INFORMATION: Nogo-B Fwd primer

<400> SEQUENCE: 16
ctgaaccaat tcctctgata tggc                                              24

<210> SEQ ID NO 17
<211> LENGTH: 19
<212> TYPE: DNA
<213> ORGANISM: artificial sequence
<220> FEATURE:
<223> OTHER INFORMATION: Nogo-B Rev primer

<400> SEQUENCE: 17
aggggctcgg gctcagtgg                                                    19

<210> SEQ ID NO 18
<211> LENGTH: 21
<212> TYPE: DNA
<213> ORGANISM: artificial sequence
<220> FEATURE:
<223> OTHER INFORMATION: Nogo-C Fwd primer

<400> SEQUENCE: 18
tgctggaggg cagatcgtgg c                                                 21

<210> SEQ ID NO 19
<211> LENGTH: 23
<212> TYPE: DNA
<213> ORGANISM: artificial sequence
<220> FEATURE:
<223> OTHER INFORMATION: Nogo-C Rev primer

<400> SEQUENCE: 19
ctgaaccaat tcctctgata tgg                                               23

<210> SEQ ID NO 20
<211> LENGTH: 460
<212> TYPE: PRT
<213> ORGANISM: artificial sequence
<220> FEATURE:
<223> OTHER INFORMATION: 2A10 humanized Heavy chain H20

<400> SEQUENCE: 20

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Met Thr Arg Asp Thr Ser Thr Ser
```

```
                85                  90                  95
Thr Ala Tyr Met Glu Leu Ser Ser Leu Arg Ser Glu Asp Thr Ala Val
                100                 105                 110
Tyr Tyr Cys Glu Leu Gly Gln Gly Tyr Trp Gly Gln Gly Thr Leu Val
            115                 120                 125
Thr Val Ser Ser Ala Ser Thr Lys Gly Pro Ser Val Phe Pro Leu Ala
    130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
                180                 185                 190
Gly Leu Tyr Ser Leu Ser Ser Val Val Thr Val Pro Ser Ser Ser Leu Gly
            195                 200                 205
Thr Gln Thr Tyr Ile Cys Asn Val Asn His Lys Pro Ser Asn Thr Lys
    210                 215                 220
Val Asp Lys Lys Val Glu Pro Lys Ser Cys Asp Lys Thr His Thr Cys
225                 230                 235                 240
Pro Pro Cys Pro Ala Pro Glu Leu Ala Gly Ala Pro Ser Val Phe Leu
                245                 250                 255
Phe Pro Pro Lys Pro Lys Asp Thr Leu Met Ile Ser Arg Thr Pro Glu
                260                 265                 270
Val Thr Cys Val Val Trp Asp Val Ser His Glu Asp Pro Glu Val Lys Phe
            275                 280                 285
Asn Trp Tyr Val Asp Gly Val Glu Val His Asn Ala Lys Thr Lys Pro
    290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                325                 330                 335
Ser Asn Lys Ala Leu Pro Ala Pro Ile Glu Lys Thr Ile Ser Lys Ala
                340                 345                 350
Lys Gly Gln Pro Arg Glu Pro Gln Val Tyr Thr Leu Pro Pro Ser Arg
            355                 360                 365
Asp Glu Leu Thr Lys Asn Gln Val Ser Leu Thr Cys Leu Val Lys Gly
    370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
                420                 425                 430
Gly Asn Val Phe Ser Cys Ser Val Met His Glu Ala Leu His Asn His
            435                 440                 445
Tyr Thr Gln Lys Ser Leu Ser Leu Ser Pro Gly Lys
    450                 455                 460

<210> SEQ ID NO 21
<211> LENGTH: 462
<212> TYPE: PRT
<213> ORGANISM: artificial sequence
<220> FEATURE:
<223> OTHER INFORMATION: 2A10 humanized heavy chain H26
```

<400> SEQUENCE: 21

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Arg Ala Thr Met Thr Arg Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Glu Leu Met Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

```
Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 22
<211> LENGTH: 462
<212> TYPE: PRT
<213> ORGANISM: artificial sequence
<220> FEATURE:
<223> OTHER INFORMATION: 2A10 humanized heavy chain H27

<400> SEQUENCE: 22

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Glu Leu Met Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320
```

-continued

```
Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 23
<211> LENGTH: 462
<212> TYPE: PRT
<213> ORGANISM: artificial sequence
<220> FEATURE:
<223> OTHER INFORMATION: 2A10 humanized heavy chain H28

<400> SEQUENCE: 23

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Met Thr Arg Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Glu Leu Met Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220
```

```
Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Lys
450                 455                 460

<210> SEQ ID NO 24
<211> LENGTH: 237
<212> TYPE: PRT
<213> ORGANISM: artificial sequence
<220> FEATURE:
<223> OTHER INFORMATION: 2A10 Light chain L16

<400> SEQUENCE: 24

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Asn Pro Val
            20                  25                  30

Thr Leu Gly Gln Pro Val Ser Ile Ser Cys Arg Ser Ser Lys Ser Leu
        35                  40                  45

Leu Tyr Lys Asp Gly Lys Thr Tyr Leu Asn Trp Phe Leu Gln Arg Pro
    50                  55                  60

Gly Gln Ser Pro Gln Leu Leu Ile Tyr Leu Met Ser Thr Arg Ala Ser
65                  70                  75                  80

Gly Val Pro Asp Arg Phe Ser Gly Gly Ser Gly Thr Asp Phe Thr
            85                  90                  95

Leu Lys Ile Ser Arg Val Glu Ala Glu Asp Val Gly Val Tyr Tyr Cys
        100                 105                 110

Gln Gln Leu Val Glu Tyr Pro Leu Thr Phe Gly Gln Gly Thr Lys Leu
    115                 120                 125
```

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Trp Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 25
<211> LENGTH: 237
<212> TYPE: PRT
<213> ORGANISM: artificial sequence
<220> FEATURE:
<223> OTHER INFORMATION: 2A10 light chain L13

<400> SEQUENCE: 25

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Leu Gly Gln Pro Ala Ser Ile Ser Cys Arg Ser Ser Lys Ser Leu
        35                  40                  45

Leu Tyr Lys Asp Gly Lys Thr Tyr Leu Asn Trp Phe Gln Gln Arg Pro
    50                  55                  60

Gly Gln Ser Pro Gln Leu Leu Ile Tyr Leu Met Ser Thr Arg Ala Ser
65                  70                  75                  80

Gly Val Pro Asp Arg Phe Ser Gly Gly Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gln Gly Thr Lys Leu
        115                 120                 125

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Trp Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 26

```
<211> LENGTH: 113
<212> TYPE: PRT
<213> ORGANISM: artificial sequence
<220> FEATURE:
<223> OTHER INFORMATION: 2A10 VH domain H20

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Asn Ile Asn Pro Ser Asn Gly Gly Thr Asn Tyr Asn Glu Lys Phe
    50                  55                  60

Lys Ser Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 27
<211> LENGTH: 113
<212> TYPE: PRT
<213> ORGANISM: artificial sequence
<220> FEATURE:
<223> OTHER INFORMATION: 2A10 VH domain H27

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Met Gln Gly Tyr Trp Gly Gln Gly Thr Leu Val Thr Val Ser
            100                 105                 110

Ser

<210> SEQ ID NO 28
<211> LENGTH: 113
<212> TYPE: PRT
<213> ORGANISM: artificial sequence
<220> FEATURE:
<223> OTHER INFORMATION: 2A10 VH domain H28

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30
```

```
Trp Met His Trp Val Arg Gln Ala Pro Gly Gln Gly Leu Glu Trp Ile
            35                  40                  45

Gly Asn Ile Asn Pro Ser Asn Gly Gly Thr Asn Tyr Asn Glu Lys Phe
 50                  55                  60

Lys Ser Lys Ala Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Glu Leu Met Gln Gly Tyr Trp Gly Gln Gly Thr Leu Val Thr Val Ser
                100                 105                 110

Ser

<210> SEQ ID NO 29
<211> LENGTH: 112
<212> TYPE: PRT
<213> ORGANISM: artificial sequence
<220> FEATURE:
<223> OTHER INFORMATION: 2A10 VL domain L13

<400> SEQUENCE: 29

Asp Ile Val Met Thr Gln Ser Pro Leu Ser Leu Pro Val Thr Leu Gly
 1               5                  10                  15

Gln Pro Ala Ser Ile Ser Cys Arg Ser Ser Lys Ser Leu Leu Tyr Lys
                20                  25                  30

Asp Gly Lys Thr Tyr Leu Asn Trp Phe Gln Gln Arg Pro Gly Gln Ser
             35                  40                  45

Pro Gln Leu Leu Ile Tyr Leu Met Ser Thr Arg Ala Ser Gly Val Pro
 50                  55                  60

Asp Arg Phe Ser Gly Gly Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Leu Thr Phe Gly Gln Gly Thr Lys Leu Glu Ile Lys
                100                 105                 110

<210> SEQ ID NO 30
<211> LENGTH: 112
<212> TYPE: PRT
<213> ORGANISM: artificial sequence
<220> FEATURE:
<223> OTHER INFORMATION: 2A10 VL domain L16

<400> SEQUENCE: 30

Asp Ile Val Met Thr Gln Ser Pro Leu Ser Asn Pro Val Thr Leu Gly
 1               5                  10                  15

Gln Pro Val Ser Ile Ser Cys Arg Ser Ser Lys Ser Leu Leu Tyr Lys
                20                  25                  30

Asp Gly Lys Thr Tyr Leu Asn Trp Phe Leu Gln Arg Pro Gly Gln Ser
             35                  40                  45

Pro Gln Leu Leu Ile Tyr Leu Met Ser Thr Arg Ala Ser Gly Val Pro
 50                  55                  60

Asp Arg Phe Ser Gly Gly Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Leu Thr Phe Gly Gln Gly Thr Lys Leu Glu Ile Lys
                100                 105                 110
```

<210> SEQ ID NO 31
<211> LENGTH: 220
<212> TYPE: PRT
<213> ORGANISM: artificial sequence
<220> FEATURE:
<223> OTHER INFORMATION: Mouse 11C7 VH domain

<400> SEQUENCE: 31

Met Asp Phe Gly Leu Ile Phe Phe Ile Val Gly Leu Leu Lys Gly Val
1               5                   10                  15

Gln Cys Glu Val Lys Leu Leu Glu Ser Gly Gly Leu Val Gln Pro Gly
            20                  25                  30

Gly Ser Leu Lys Leu Ser Cys Val Val Ser Gly Phe Asp Phe Arg Arg
        35                  40                  45

Asn Trp Met Ser Trp Val Arg Gln Ala Pro Gly Lys Gly Leu Glu Trp
    50                  55                  60

Ile Gly Glu Ile Asn Pro Asp Ser Ser Lys Ile Asn Tyr Thr Pro Ser
65                  70                  75                  80

Leu Lys Asp Lys Phe Ile Ile Ser Arg Asp Asn Ala Lys Asn Thr Leu
                85                  90                  95

Tyr Leu Gln Val Ser Thr Val Arg Ser Glu Asp Thr Ala Leu Tyr Thr
            100                 105                 110

Cys Val Arg Pro Val Trp Met Tyr Ala Met Asp Tyr Trp Gly Gln Gly
        115                 120                 125

Thr Ser Val Thr Val Ser Ser Ala Lys Thr Thr Pro Pro Ser Val Tyr
    130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Pro Ser Ser
        195                 200                 205

Thr Trp Pro Ser Glu Thr Val Thr Cys Asn Val Ala
    210                 215                 220

<210> SEQ ID NO 32
<211> LENGTH: 237
<212> TYPE: PRT
<213> ORGANISM: artificial sequence
<220> FEATURE:
<223> OTHER INFORMATION: Mouse 11C7 light chain

<400> SEQUENCE: 32

Met Ser Pro Ala Gln Phe Leu Phe Leu Leu Val Leu Trp Ile Arg Glu
1               5                   10                  15

Thr Ser Gly Asp Val Leu Leu Thr Gln Thr Pro Leu Thr Leu Ser Ile
            20                  25                  30

Thr Ile Gly Gln Pro Ala Ser Ile Ser Cys Lys Ser Ser Gln Ser Leu
        35                  40                  45

Leu His Ser Asp Gly Lys Thr Tyr Leu Asn Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Glu Phe Thr Gly Ser Gly Ser Gly Thr Asp Phe Thr

```
                    85                  90                  95
Leu Lys Ile Ser Arg Val Glu Ala Gly Asp Leu Gly Leu Tyr Tyr Cys
                100                 105                 110

Trp Gln Gly Thr His Phe Pro Gln Thr Phe Gly Gly Gly Thr Lys Leu
                115                 120                 125

Glu Ile Lys Arg Ala Asp Ala Ala Pro Thr Val Ser Ile Phe Pro Pro
130                 135                 140

Ser Ser Gly Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Gln Asp Ser Lys
                180                 185                 190

Asp Ser Thr Tyr Ser Met Ser Ser Thr Leu Thr Leu Thr Lys Asp Glu
                195                 200                 205

Tyr Glu Arg His Asn Ser Tyr Thr Cys Glu Ala Thr His Lys Thr Ser
                210                 215                 220

Thr Ser Pro Ile Val Lys Ser Phe Asn Arg Gly Glu Cys
225                 230                 235

<210> SEQ ID NO 33
<211> LENGTH: 246
<212> TYPE: PRT
<213> ORGANISM: artificial sequence
<220> FEATURE:
<223> OTHER INFORMATION: Human 6A3 VH domain

<400> SEQUENCE: 33

Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Tyr Trp Met Ser Trp Val Arg Gln Ala Pro Gly Lys Gly Leu
50                  55                  60

Glu Trp Val Ala Thr Ile Lys Gln Asp Gly Ser Gln Lys Asn Tyr Val
65                  70                  75                  80

Asp Ser Val Lys Gly Arg Phe Thr Ile Ser Arg Asp Asn Ala Lys Asn
                85                  90                  95

Ser Leu Tyr Leu Arg Leu Asn Ser Leu Arg Ala Glu Asp Thr Ala Val
                100                 105                 110

Tyr Tyr Cys Ala Thr Glu Leu Phe Asp Leu Trp Gly Arg Gly Ser Leu
                115                 120                 125

Val Thr Val Ser Ser Ala Ser Thr Lys Gly Pro Ser Val Phe Pro Leu
                130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
                180                 185                 190

Ser Gly Leu Tyr Ser Leu Ser Ser Val Val Thr Val Pro Ser Ser Ser
                195                 200                 205

Leu Gly Thr Gln Thr Tyr Ile Cys Asn Val Asn His Lys Pro Ser Asn
```

```
                210                 215                 220
Thr Lys Val Asp Lys Arg Val Glu Pro Lys Ser Cys Asp Lys Thr His
225                 230                 235                 240

Thr Cys Pro Pro Cys Pro
                245

<210> SEQ ID NO 34
<211> LENGTH: 234
<212> TYPE: PRT
<213> ORGANISM: artificial sequence
<220> FEATURE:
<223> OTHER INFORMATION: Human 6A3 VL domain

<400> SEQUENCE: 34

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 35
<211> LENGTH: 260
<212> TYPE: PRT
<213> ORGANISM: artificial sequence
<220> FEATURE:
<223> OTHER INFORMATION: Fragment 680-939 human Nogo-A

<400> SEQUENCE: 35

Pro Glu Asn Ile Asn Ala Ala Leu Gln Glu Thr Glu Ala Pro Tyr Ile
1               5                   10                  15

Ser Ile Ala Cys Asp Leu Ile Lys Glu Thr Lys Leu Ser Ala Glu Pro
                20                  25                  30
```

```
Ala Pro Asp Phe Ser Asp Tyr Ser Glu Met Ala Lys Val Glu Gln Pro
            35                  40                  45

Val Pro Asp His Ser Glu Leu Val Glu Asp Ser Pro Asp Ser Glu
 50                  55                  60

Pro Val Asp Leu Phe Ser Asp Ser Ile Pro Asp Val Pro Gln Lys
 65                  70                  75                  80

Gln Asp Glu Thr Val Met Leu Val Lys Glu Ser Leu Thr Glu Thr Ser
                 85                  90                  95

Phe Glu Ser Met Ile Glu Tyr Glu Asn Lys Lys Leu Ser Ala Leu
            100                 105                 110

Pro Pro Glu Gly Gly Lys Pro Tyr Leu Glu Ser Phe Lys Leu Ser Leu
            115                 120                 125

Asp Asn Thr Lys Asp Thr Leu Leu Pro Asp Glu Val Ser Thr Leu Ser
 130                 135                 140

Lys Lys Glu Lys Ile Pro Leu Gln Met Glu Glu Leu Ser Thr Ala Val
 145                 150                 155                 160

Tyr Ser Asn Asp Asp Leu Phe Ile Ser Lys Glu Ala Gln Ile Arg Glu
                 165                 170                 175

Thr Glu Thr Phe Ser Asp Ser Ser Pro Ile Glu Ile Ile Asp Glu Phe
            180                 185                 190

Pro Thr Leu Ile Ser Ser Lys Thr Asp Ser Phe Ser Lys Leu Ala Arg
            195                 200                 205

Glu Tyr Thr Asp Leu Glu Val Ser His Lys Ser Glu Ile Ala Asn Ala
 210                 215                 220

Pro Asp Gly Ala Gly Ser Leu Pro Cys Thr Glu Leu Pro His Asp Leu
225                 230                 235                 240

Ser Leu Lys Asn Ile Gln Pro Lys Val Glu Glu Lys Ile Ser Phe Ser
                245                 250                 255

Asp Asp Phe Ser
            260

<210> SEQ ID NO 36
<211> LENGTH: 188
<212> TYPE: PRT
<213> ORGANISM: artificial sequence
<220> FEATURE:
<223> OTHER INFORMATION: Fragment 940-1127 Human Nogo-A

<400> SEQUENCE: 36

Lys Asn Gly Ser Ala Thr Ser Lys Val Leu Leu Leu Pro Pro Asp Val
 1               5                  10                  15

Ser Ala Leu Ala Thr Gln Ala Glu Ile Glu Ser Ile Val Lys Pro Lys
                 20                  25                  30

Val Leu Val Lys Glu Ala Glu Lys Lys Leu Pro Ser Asp Thr Glu Lys
             35                  40                  45

Glu Asp Arg Ser Pro Ser Ala Ile Phe Ser Ala Glu Leu Ser Lys Thr
 50                  55                  60

Ser Val Val Asp Leu Leu Tyr Trp Arg Asp Ile Lys Lys Thr Gly Val
 65                  70                  75                  80

Val Phe Gly Ala Ser Leu Phe Leu Leu Leu Ser Leu Thr Val Phe Ser
                 85                  90                  95

Ile Val Ser Val Thr Ala Tyr Ile Ala Leu Ala Leu Leu Ser Val Thr
            100                 105                 110

Ile Ser Phe Arg Ile Tyr Lys Gly Val Ile Gln Ala Ile Gln Lys Ser
            115                 120                 125
```

-continued

```
Asp Glu Gly His Pro Phe Arg Ala Tyr Leu Glu Ser Glu Val Ala Ile
130                 135                 140

Ser Glu Glu Leu Val Gln Lys Tyr Ser Asn Ser Ala Leu Gly His Val
145                 150                 155                 160

Asn Cys Thr Ile Lys Glu Leu Arg Arg Leu Phe Leu Val Asp Asp Leu
                165                 170                 175

Val Asp Ser Leu Lys Phe Ala Val Leu Met Trp Val
                180                 185

<210> SEQ ID NO 37
<211> LENGTH: 979
<212> TYPE: PRT
<213> ORGANISM: artificial sequence
<220> FEATURE:
<223> OTHER INFORMATION: Fragment 1-979 Human Nogo-A

<400> SEQUENCE: 37

Met Glu Asp Leu Asp Gln Ser Pro Leu Val Ser Ser Ser Asp Ser Pro
1               5                   10                  15

Pro Arg Pro Gln Pro Ala Phe Lys Tyr Gln Phe Val Arg Glu Pro Glu
                20                  25                  30

Asp Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
                100                 105                 110

Val Ser Ser Thr Val Pro Ala Pro Ser Pro Leu Ser Ala Ala Ala Val
            115                 120                 125

Ser Pro Ser Lys Leu Pro Glu Asp Asp Glu Pro Pro Ala Arg Pro Pro
    130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
                180                 185                 190

Pro Ala Ala Ser Glu Pro Val Ile Arg Ser Ser Ala Glu Asn Met Asp
            195                 200                 205

Leu Lys Glu Gln Pro Gly Asn Thr Ile Ser Ala Gly Gln Glu Asp Phe
    210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
                260                 265                 270

Ser Lys Glu Val Ser Glu Lys Ala Lys Thr Leu Leu Ile Asp Arg Asp
            275                 280                 285

Leu Thr Glu Phe Ser Glu Leu Glu Tyr Ser Glu Met Gly Ser Ser Phe
    290                 295                 300
```

-continued

```
Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
            325                 330                 335

Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
            355                 360                 365

Phe Asn Glu Lys Arg Val Ala Val Glu Ala Pro Met Arg Glu Glu Tyr
    370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
            405                 410                 415

Glu Ser Lys Val Asp Lys Lys Cys Phe Ala Asp Ser Leu Glu Gln Thr
            420                 425                 430

Asn His Glu Lys Asp Ser Glu Ser Ser Asn Asp Asp Thr Ser Phe Pro
            435                 440                 445

Ser Thr Pro Glu Gly Ile Lys Asp Arg Ser Gly Ala Tyr Ile Thr Cys
450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
            485                 490                 495

Ile Glu Glu Lys Lys Ala Gln Ile Val Thr Glu Lys Asn Thr Ser Thr
            500                 505                 510

Lys Thr Ser Asn Pro Phe Leu Val Ala Ala Gln Asp Ser Glu Thr Asp
            515                 520                 525

Tyr Val Thr Thr Asp Asn Leu Thr Lys Val Thr Glu Glu Val Val Ala
            530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
            565                 570                 575

Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
            595                 600                 605

Pro Val Leu Pro Asp Ile Val Met Glu Ala Pro Leu Asn Ser Ala Val
    610                 615                 620

Pro Ser Ala Gly Ala Ser Val Ile Gln Pro Ser Ser Pro Leu Glu
625                 630                 635                 640

Ala Ser Ser Val Asn Tyr Glu Ser Ile Lys His Glu Pro Glu Asn Pro
            645                 650                 655

Pro Pro Tyr Glu Glu Ala Met Ser Val Ser Leu Lys Lys Val Ser Gly
            660                 665                 670

Ile Lys Glu Glu Ile Lys Glu Pro Glu Asn Ile Asn Ala Ala Leu Gln
            675                 680                 685

Glu Thr Glu Ala Pro Tyr Ile Ser Ile Ala Cys Asp Leu Ile Lys Glu
            690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
```

```
                    725                 730                 735
Asp Ser Ser Pro Asp Ser Glu Pro Val Asp Leu Phe Ser Asp Asp Ser
                    740                 745                 750
Ile Pro Asp Val Pro Gln Lys Gln Asp Glu Thr Val Met Leu Val Lys
                    755                 760                 765
Glu Ser Leu Thr Glu Thr Ser Phe Glu Ser Met Ile Glu Tyr Glu Asn
                    770                 775                 780
Lys Glu Lys Leu Ser Ala Leu Pro Pro Glu Gly Gly Lys Pro Tyr Leu
785                 790                 795                 800
Glu Ser Phe Lys Leu Ser Leu Asp Asn Thr Lys Asp Thr Leu Leu Pro
                    805                 810                 815
Asp Glu Val Ser Thr Leu Ser Lys Lys Glu Lys Ile Pro Leu Gln Met
                    820                 825                 830
Glu Glu Leu Ser Thr Ala Val Tyr Ser Asn Asp Asp Leu Phe Ile Ser
                    835                 840                 845
Lys Glu Ala Gln Ile Arg Glu Thr Glu Thr Phe Ser Asp Ser Ser Pro
850                 855                 860
Ile Glu Ile Ile Asp Glu Phe Pro Thr Leu Ile Ser Ser Lys Thr Asp
865                 870                 875                 880
Ser Phe Ser Lys Leu Ala Arg Glu Tyr Thr Asp Leu Glu Val Ser His
                    885                 890                 895
Lys Ser Glu Ile Ala Asn Ala Pro Asp Gly Ala Gly Ser Leu Pro Cys
                    900                 905                 910
Thr Glu Leu Pro His Asp Leu Ser Leu Lys Asn Ile Gln Pro Lys Val
                    915                 920                 925
Glu Glu Lys Ile Ser Phe Ser Asp Asp Phe Ser Lys Asn Gly Ser Ala
                    930                 935                 940
Thr Ser Lys Val Leu Leu Leu Pro Pro Asp Val Ser Ala Leu Ala Thr
945                 950                 955                 960
Gln Ala Glu Ile Glu Ser Ile Val Lys Pro Lys Val Leu Val Lys Glu
                    965                 970                 975
Ala Glu Lys

<210> SEQ ID NO 38
<211> LENGTH: 16
<212> TYPE: PRT
<213> ORGANISM: artificial sequence
<220> FEATURE:
<223> OTHER INFORMATION: Fragment 342-357 Human Nogo-A

<400> SEQUENCE: 38

Asn Gln Gln Glu Leu Pro Thr Ala Leu Thr Lys Leu Val Lys Glu Asp
1               5                   10                  15

<210> SEQ ID NO 39
<211> LENGTH: 182
<212> TYPE: PRT
<213> ORGANISM: artificial
<220> FEATURE:
<223> OTHER INFORMATION: Fragment 544-725 Human Nogo-A

<400> SEQUENCE: 39

Ala Asn Met Pro Glu Gly Leu Thr Pro Asp Leu Val Gln Glu Ala Cys
1               5                   10                  15

Glu Ser Glu Leu Asn Glu Val Thr Gly Thr Lys Ile Ala Tyr Glu Thr
                20                  25                  30

Lys Met Asp Leu Val Gln Thr Ser Glu Val Met Gln Glu Ser Leu Tyr
```

```
                35                  40                  45
Pro Ala Gln Leu Cys Pro Ser Phe Glu Glu Ser Glu Ala Thr Pro
 50                  55                  60

Ser Pro Val Leu Pro Asp Ile Val Met Glu Ala Pro Leu Asn Ser Ala
 65                  70                  75                  80

Val Pro Ser Ala Gly Ala Ser Val Ile Gln Pro Ser Ser Ser Pro Leu
                 85                  90                  95

Glu Ala Ser Ser Val Asn Tyr Glu Ser Ile Lys His Glu Pro Glu Asn
                100                 105                 110

Pro Pro Pro Tyr Glu Glu Ala Met Ser Val Ser Leu Lys Lys Val Ser
                115                 120                 125

Gly Ile Lys Glu Glu Ile Lys Glu Pro Glu Asn Ile Asn Ala Ala Leu
                130                 135                 140

Gln Glu Thr Glu Ala Pro Tyr Ile Ser Ile Ala Cys Asp Leu Ile Lys
145                 150                 155                 160

Glu Thr Lys Leu Ser Ala Glu Pro Ala Pro Asp Phe Ser Asp Tyr Ser
                165                 170                 175

Glu Met Ala Lys Val Glu
                180

<210> SEQ ID NO 40
<211> LENGTH: 182
<212> TYPE: PRT
<213> ORGANISM: artificial sequence
<220> FEATURE:
<223> OTHER INFORMATION: Fragment 567-748 Human Nogo-A

<400> SEQUENCE: 40

Thr Gly Thr Lys Ile Ala Tyr Glu Thr Lys Met Asp Leu Val Gln Thr
 1               5                  10                  15

Ser Glu Val Met Gln Glu Ser Leu Tyr Pro Ala Ala Gln Leu Cys Pro
                20                  25                  30

Ser Phe Glu Glu Ser Glu Ala Thr Pro Ser Pro Val Leu Pro Asp Ile
                35                  40                  45

Val Met Glu Ala Pro Leu Asn Ser Ala Val Pro Ser Ala Gly Ala Ser
 50                  55                  60

Val Ile Gln Pro Ser Ser Ser Pro Leu Glu Ala Ser Ser Val Asn Tyr
 65                  70                  75                  80

Glu Ser Ile Lys His Glu Pro Glu Asn Pro Pro Pro Tyr Glu Glu Ala
                 85                  90                  95

Met Ser Val Ser Leu Lys Lys Val Ser Gly Ile Lys Glu Glu Ile Lys
                100                 105                 110

Glu Pro Glu Asn Ile Asn Ala Ala Leu Gln Glu Thr Glu Ala Pro Tyr
                115                 120                 125

Ile Ser Ile Ala Cys Asp Leu Ile Lys Glu Thr Lys Leu Ser Ala Glu
                130                 135                 140

Pro Ala Pro Asp Phe Ser Asp Tyr Ser Glu Met Ala Lys Val Glu Gln
145                 150                 155                 160

Pro Val Pro Asp His Ser Glu Leu Val Glu Asp Ser Ser Pro Asp Ser
                165                 170                 175

Glu Pro Val Asp Leu Phe
                180

<210> SEQ ID NO 41
<211> LENGTH: 12
<212> TYPE: PRT
```

```
<213> ORGANISM: artificial sequence
<220> FEATURE:
<223> OTHER INFORMATION: Fragment 610-621 Human Nogo-A

<400> SEQUENCE: 41

Val Leu Pro Asp Ile Val Met Glu Ala Pro Leu Asn
1               5                   10

<210> SEQ ID NO 42
<211> LENGTH: 18
<212> TYPE: PRT
<213> ORGANISM: artificial sequence
<220> FEATURE:
<223> OTHER INFORMATION: Fragment 101-118 Bovine Nogo-A

<400> SEQUENCE: 42

Asn Tyr Glu Ser Ile Lys Phe Glu Pro Glu Asn Pro Pro Tyr Glu
1               5                   10                  15

Glu Ala

<210> SEQ ID NO 43
<211> LENGTH: 18
<212> TYPE: PRT
<213> ORGANISM: artificial sequence
<220> FEATURE:
<223> OTHER INFORMATION: Fragment 623-640 Rat Nogo-A

<400> SEQUENCE: 43

Ser Tyr Asp Ser Ile Lys Leu Glu Pro Glu Asn Pro Pro Tyr Glu
1               5                   10                  15

Glu Ala
```